US011589843B2

(12) United States Patent
Bullington et al.

(10) Patent No.: US 11,589,843 B2
(45) Date of Patent: *Feb. 28, 2023

(54) APPARATUS AND METHODS FOR DISINFECTION OF A SPECIMEN CONTAINER

(71) Applicant: Magnolia Medical Technologies, Inc., Seattle, WA (US)

(72) Inventors: Gregory J. Bullington, Seattle, WA (US); Richard G. Patton, Seattle, WA (US); Shan E. Gaw, Seattle, WA (US)

(73) Assignee: Magnolia Medical Technologies, Inc., Seattle, WA (US)

(*) Notice: Subject to any disclaimer, the term of this patent is extended or adjusted under 35 U.S.C. 154(b) by 862 days.

This patent is subject to a terminal disclaimer.

(21) Appl. No.: 16/146,251

(22) Filed: Sep. 28, 2018

(65) Prior Publication Data

US 2019/0125315 A1 May 2, 2019

Related U.S. Application Data

(63) Continuation of application No. 14/636,485, filed on Mar. 3, 2015, now Pat. No. 10,123,783.
(Continued)

(51) Int. Cl.
*A61B 10/00* (2006.01)
*A61B 5/15* (2006.01)
(Continued)

(52) U.S. Cl.
CPC .... *A61B 10/0045* (2013.01); *A61B 5/150351* (2013.01); *A61B 10/0096* (2013.01);
(Continued)

(58) Field of Classification Search
CPC ........ A61J 1/1406; A61J 1/1443; A61J 1/201; A61J 2001/1425; A61J 2001/2068; A61J 1/2096; A61B 5/150351; B01L 2300/06
See application file for complete search history.

(56) References Cited

U.S. PATENT DOCUMENTS 2,707,953 A 5/1955 Ryan
2,922,419 A 1/1960 Bednarz
(Continued)

FOREIGN PATENT DOCUMENTS

CN 102548524 A 7/2012
CN 102971040 A 3/2013
(Continued)

OTHER PUBLICATIONS

Office Action for U.S. Appl. No. 14/636,485, dated Feb. 9, 2017, 2017, 8 pages.
(Continued)

*Primary Examiner* — Leslie R Deak
(74) *Attorney, Agent, or Firm* — Cooley LLP

(57) ABSTRACT

An apparatus includes a transfer adapter, a puncture member, a disinfection member, and a fluid reservoir. The transfer adapter has a proximal end portion and a distal end portion, and defines an inner volume configured to receive the puncture member. The transfer adapter is coupled to the disinfection member. The distal end portion of the transfer adapter includes a port fluidically coupled to the puncture member and configured to be placed in fluid communication with a bodily-fluid of a patient. The proximal end portion is configured to receive a portion of the fluid reservoir to allow the fluid reservoir to be moved within the inner volume between a first position, in which a surface of the fluid reservoir is placed in contact with the disinfection member, and a second position, in which the puncture member punctures the surface to place the puncture member in fluid communication with the fluid reservoir.

19 Claims, 34 Drawing Sheets

Related U.S. Application Data

(60) Provisional application No. 61/947,076, filed on Mar. 3, 2014.

(51) Int. Cl.
  *A61J 1/20* (2006.01)
  *A61J 1/14* (2006.01)
(52) U.S. Cl.
  CPC ............ *A61J 1/2096* (2013.01); *A61J 1/1406* (2013.01); *A61J 1/201* (2015.05); *B01L 2200/026* (2013.01); *B01L 2300/06* (2013.01)

(56) References Cited

U.S. PATENT DOCUMENTS

| | | |
|---|---|---|
| 2,992,974 A | 7/1961 | Belcove et al. |
| 3,013,557 A | 12/1961 | Pallotta |
| 3,098,016 A | 7/1963 | Cooper et al. |
| 3,382,865 A | 5/1968 | Worral, Jr. |
| 3,405,706 A | 10/1968 | Cinqualbre |
| 3,494,351 A | 2/1970 | Horn |
| 3,577,980 A | 5/1971 | Cohen |
| 3,635,798 A | 1/1972 | Kirkham et al. |
| 3,648,684 A | 3/1972 | Barnwell et al. |
| 3,777,773 A | 12/1973 | Tolbert |
| 3,817,240 A | 6/1974 | Ayres |
| 3,834,372 A | 9/1974 | Turney |
| 3,848,579 A | 11/1974 | Villa-Real |
| 3,848,581 A | 11/1974 | Cinqualbre et al. |
| 3,874,367 A | 4/1975 | Ayres |
| 3,886,930 A | 6/1975 | Ryan |
| 3,890,203 A | 6/1975 | Mehl |
| 3,890,968 A | 6/1975 | Pierce et al. |
| 3,937,211 A | 2/1976 | Merten |
| 4,056,101 A | 11/1977 | Geissler et al. |
| 4,057,050 A | 11/1977 | Sarstedt |
| 4,063,460 A | 12/1977 | Svensson |
| 4,077,395 A | 3/1978 | Woolner |
| 4,106,497 A | 8/1978 | Percarpio |
| 4,133,863 A | 1/1979 | Koenig |
| 4,154,229 A | 5/1979 | Nugent |
| 4,166,450 A | 9/1979 | Abramson |
| 4,212,308 A | 7/1980 | Percarpio |
| 4,275,730 A | 6/1981 | Hussein |
| 4,340,067 A | 7/1982 | Rattenborg |
| 4,340,068 A | 7/1982 | Kaufman |
| 4,370,987 A | 2/1983 | Bazell et al. |
| 4,398,544 A | 8/1983 | Nugent et al. |
| 4,412,548 A | 11/1983 | Hoch |
| 4,416,290 A | 11/1983 | Lutkowski |
| 4,425,235 A | 1/1984 | Cornell et al. |
| 4,444,203 A | 4/1984 | Engelman |
| 4,459,997 A | 7/1984 | Sarstedt |
| 4,509,534 A | 4/1985 | Tassin, Jr. |
| 4,608,996 A | 9/1986 | Brown |
| 4,657,027 A | 4/1987 | Paulsen |
| 4,657,160 A | 4/1987 | Woods et al. |
| 4,673,386 A | 6/1987 | Gordon |
| 4,676,256 A | 6/1987 | Golden |
| 4,679,571 A | 7/1987 | Frankel et al. |
| 4,705,497 A | 10/1987 | Shitaokoshi et al. |
| 4,714,461 A | 12/1987 | Gabel |
| 4,772,273 A | 9/1988 | Alchas |
| 4,865,583 A | 9/1989 | Tu |
| 4,886,072 A | 12/1989 | Percarpio et al. |
| 4,890,627 A | 1/1990 | Haber et al. |
| 5,032,116 A | 7/1991 | Peterson et al. |
| 5,066,284 A | 11/1991 | Mersch et al. |
| 5,084,034 A | 1/1992 | Zanotti |
| 5,097,842 A | 3/1992 | Bonn |
| 5,108,927 A | 4/1992 | Dom |
| 5,116,323 A | 5/1992 | Kreuzer et al. |
| 5,122,129 A | 6/1992 | Olson et al. |
| 5,222,502 A | 6/1993 | Kurose |
| 5,269,317 A | 12/1993 | Bennett |
| 5,330,464 A | 7/1994 | Mathias et al. |
| 5,354,537 A | 10/1994 | Mathias |
| 5,450,856 A | 9/1995 | Norris |
| 5,485,854 A | 1/1996 | Hollister |
| 5,507,299 A | 4/1996 | Roland |
| 5,520,193 A | 5/1996 | Suzuki et al. |
| 5,575,777 A | 11/1996 | Cover et al. |
| 5,603,700 A | 2/1997 | Daneshvar |
| 5,649,912 A | 7/1997 | Peterson |
| 5,749,857 A | 5/1998 | Cuppy |
| 5,762,633 A | 6/1998 | Whisson |
| 5,824,001 A | 10/1998 | Erskine |
| 5,833,213 A | 11/1998 | Ryan |
| 5,865,812 A | 2/1999 | Correia |
| 5,871,699 A | 2/1999 | Ruggeri |
| 5,911,705 A | 6/1999 | Howell |
| 5,922,551 A | 7/1999 | Durbin et al. |
| 5,971,956 A | 10/1999 | Epstein |
| 6,210,909 B1 | 4/2001 | Guirguis |
| 6,299,131 B1 | 10/2001 | Ryan |
| 6,328,726 B1 | 12/2001 | Ishida et al. |
| 6,364,890 B1 | 4/2002 | Lum et al. |
| 6,387,086 B2 | 5/2002 | Mathias et al. |
| 6,403,381 B1 | 6/2002 | Mann et al. |
| 6,520,948 B1 | 2/2003 | Mathias et al. |
| 6,626,884 B1 | 9/2003 | Dillon et al. |
| 6,648,835 B1 | 11/2003 | Shemesh |
| 6,692,479 B2 | 2/2004 | Kraus et al. |
| 6,746,420 B1 | 6/2004 | Prestidge et al. |
| 6,905,483 B2 | 6/2005 | Newby et al. |
| 6,913,580 B2 | 7/2005 | Stone |
| 7,044,941 B2 | 5/2006 | Mathias et al. |
| 7,087,047 B2 | 8/2006 | Kraus et al. |
| 7,261,707 B2 * | 8/2007 | Frezza .................. A61J 1/065 604/416 |
| 7,335,188 B2 | 2/2008 | Graf |
| 7,384,416 B2 | 6/2008 | Goudaliez et al. |
| 7,615,033 B2 | 11/2009 | Leong |
| 7,648,491 B2 | 1/2010 | Rogers |
| 7,744,573 B2 | 6/2010 | Gordon et al. |
| 7,766,879 B2 | 8/2010 | Tan et al. |
| 7,780,794 B2 | 8/2010 | Rogers et al. |
| 8,070,725 B2 | 12/2011 | Christensen |
| 8,197,420 B2 | 6/2012 | Patton |
| 8,231,546 B2 | 7/2012 | Patton |
| 8,337,418 B2 | 12/2012 | Patton |
| 8,383,044 B2 | 2/2013 | Davis et al. |
| 8,412,300 B2 | 4/2013 | Sonderegger |
| 8,535,241 B2 | 9/2013 | Bullington et al. |
| 8,603,009 B2 | 12/2013 | Tan et al. |
| 8,647,286 B2 | 2/2014 | Patton |
| 8,795,198 B2 | 8/2014 | Tan et al. |
| 8,832,894 B2 | 9/2014 | Rogers et al. |
| 8,864,684 B2 | 10/2014 | Bullington et al. |
| 8,876,734 B2 | 11/2014 | Patton |
| 9,022,950 B2 | 5/2015 | Bullington et al. |
| 9,022,951 B2 | 5/2015 | Bullington et al. |
| 9,060,724 B2 | 6/2015 | Bullington et al. |
| 9,060,725 B2 | 6/2015 | Bullington et al. |
| 9,204,864 B2 | 12/2015 | Bullington et al. |
| 9,259,284 B2 | 2/2016 | Rogers et al. |
| 9,314,201 B2 | 4/2016 | Burkholz et al. |
| 9,636,278 B2 | 5/2017 | Sanders et al. |
| 9,743,874 B2 | 8/2017 | Kashmirian |
| 9,855,001 B2 | 1/2018 | Patton |
| 9,855,002 B2 | 1/2018 | Patton |
| 9,861,306 B2 | 1/2018 | Patton |
| 9,872,645 B2 | 1/2018 | Patton |
| 9,895,092 B2 | 2/2018 | Burkholz |
| 9,950,084 B2 | 4/2018 | Bullington et al. |
| 9,980,878 B2 | 5/2018 | Marici et al. |
| 10,022,530 B2 | 7/2018 | Tekeste |
| 10,028,687 B2 | 7/2018 | Patton |
| 10,028,688 B2 | 7/2018 | Patton |
| 10,028,689 B2 | 7/2018 | Patton |
| 10,039,483 B2 | 8/2018 | Bullington et al. |
| 10,045,724 B2 | 8/2018 | Patton |
| 10,052,053 B2 | 8/2018 | Patton |
| 10,086,142 B2 | 10/2018 | Tekeste |

(56) References Cited

U.S. PATENT DOCUMENTS

| | | |
|---|---|---|
| 10,123,783 B2 * | 11/2018 | Bullington ............ A61B 50/33 |
| 10,219,982 B2 | 3/2019 | Weir et al. |
| 10,220,139 B2 | 3/2019 | Bullington et al. |
| 10,251,590 B2 | 4/2019 | Bullington et al. |
| 10,265,007 B2 | 4/2019 | Bullington et al. |
| 10,391,031 B2 | 8/2019 | Yevmenenko et al. |
| 10,624,977 B2 | 4/2020 | Bullington et al. |
| 10,744,315 B2 | 8/2020 | Sanders |
| 10,772,548 B2 | 9/2020 | Bullington et al. |
| 2001/0039058 A1 | 11/2001 | Iheme et al. |
| 2002/0002349 A1 | 1/2002 | Flaherty et al. |
| 2002/0183651 A1 | 12/2002 | Hyun |
| 2002/0193751 A1 | 12/2002 | Theeuwes et al. |
| 2003/0055381 A1 | 3/2003 | Wilkinson |
| 2003/0069543 A1 | 4/2003 | Carpenter et al. |
| 2003/0208151 A1 | 11/2003 | Kraus et al. |
| 2004/0009542 A1 | 1/2004 | Dumont et al. |
| 2004/0010228 A1 | 1/2004 | Swenson et al. |
| 2004/0054283 A1 | 3/2004 | Corey et al. |
| 2004/0054333 A1 | 3/2004 | Theeuwes et al. |
| 2004/0073171 A1 | 4/2004 | Rogers et al. |
| 2004/0127816 A1 | 7/2004 | Galvao |
| 2004/0147855 A1 | 7/2004 | Marsden |
| 2005/0004524 A1 | 1/2005 | Newby et al. |
| 2005/0148992 A1 | 7/2005 | Simas et al. |
| 2005/0148993 A1 | 7/2005 | Mathias et al. |
| 2005/0240161 A1 | 10/2005 | Crawford |
| 2005/0245885 A1 | 11/2005 | Brown |
| 2005/0273019 A1 | 12/2005 | Conway et al. |
| 2005/0281713 A1 | 12/2005 | Hampsch et al. |
| 2006/0251622 A1 | 11/2006 | Suzuki et al. |
| 2006/0287639 A1 | 12/2006 | Sharp |
| 2007/0100250 A1 | 5/2007 | Kline |
| 2007/0119508 A1 | 5/2007 | West et al. |
| 2007/0287948 A1 | 12/2007 | Sakiewicz |
| 2008/0108954 A1 | 5/2008 | Mathias et al. |
| 2008/0185056 A1 | 8/2008 | Diodati et al. |
| 2008/0319346 A1 | 12/2008 | Crawford et al. |
| 2009/0050213 A1 | 2/2009 | Biddell et al. |
| 2010/0094171 A1 | 4/2010 | Conway et al. |
| 2010/0152681 A1 | 6/2010 | Mathias |
| 2010/0268118 A1 | 10/2010 | Schweiger |
| 2010/0306938 A1 | 12/2010 | Rogers et al. |
| 2011/0232020 A1 | 9/2011 | Rogers et al. |
| 2011/0306899 A1 | 12/2011 | Brown et al. |
| 2012/0035540 A1 | 2/2012 | Ferren et al. |
| 2012/0216359 A1 | 8/2012 | Rogers et al. |
| 2012/0265099 A1 | 10/2012 | Goodnow, II et al. |
| 2014/0066880 A1 | 3/2014 | Prince et al. |
| 2014/0150832 A1 | 6/2014 | Rogers et al. |
| 2014/0261558 A1 | 9/2014 | Rogers |
| 2014/0261581 A1 | 9/2014 | Rogers et al. |
| 2015/0018715 A1 | 1/2015 | Walterspiel |
| 2015/0094615 A1 | 4/2015 | Patton |
| 2015/0342510 A1 | 12/2015 | Bullington et al. |
| 2015/0351679 A1 | 12/2015 | Bullington et al. |
| 2016/0113560 A1 | 4/2016 | Bullington et al. |
| 2016/0213294 A1 | 7/2016 | Patton |
| 2017/0361019 A1 | 12/2017 | Hopkins |
| 2018/0116577 A1 | 5/2018 | Bullington et al. |
| 2018/0361003 A1 | 12/2018 | Dombrowski et al. |
| 2019/0159711 A1 | 5/2019 | Rogers et al. |
| 2019/0234540 A1 | 8/2019 | Marici et al. |

FOREIGN PATENT DOCUMENTS

| | | |
|---|---|---|
| CN | 103477201 A | 12/2013 |
| EP | 0 565 103 A1 | 10/1993 |
| EP | 1 219 283 B1 | 6/2005 |
| EP | 2 692 324 | 2/2014 |
| WO | WO 1986/005568 | 9/1986 |
| WO | WO 1991/018632 | 12/1991 |
| WO | WO 1997/018845 | 5/1997 |
| WO | WO 2000/041624 | 7/2000 |
| WO | WO 2003/047660 | 6/2003 |
| WO | WO 2005/068011 | 7/2005 |
| WO | WO 2006/031500 | 3/2006 |
| WO | WO 2012/012127 | 1/2012 |
| WO | WO 2015/134431 | 9/2015 |
| WO | WO 2017/041087 | 3/2017 |

OTHER PUBLICATIONS

Office Action for U.S. Appl. No. 14/636,485, dated Jul. 7, 2017, 8 pages.

International Search Report and Written Opinion for International Application No. PCT/US2015/018397, dated Aug. 11, 2015, 16 pages.

Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.

Calam, R. R., "Recommended 'Order of Draw' for Collecting Blood Specimens Into Additive-Containing Tubes," Letter to the Editor, Clinical Chemistry, 28(6):1399 (1982), 1 page.

Hall, K. K. et al., "Updated Review of Blood Culture Contamination," Clinical Microbiology Reviews, 19(4):788-802 (2006).

Kim, J. Y. et al., "The Sum of the Parts is Greater Than the Whole: Reducing Blood Culture Contamination," Annals of Internal Medicine, 154:202-203 (2011).

Levin, P. D. et al., "Use of the Nonwire Central Line Hub to Reduce Blood Culture Contamination," Chest, 143(3):640-645 (2013).

Order of Draw for Multiple Tube Collections, LabNotes, a newsletter from BD Diagnostics,—Preanalytical Systems, 17(1):3 (2007).

Patton, R. G. et al., "Innovation for Reducing Blood Culture Contamination: Initial Specimen Diversion Technique," Journal of Clinical Microbiology, 48(12):4501-4503 (2010).

Proehl, J. A. et al., "Clinical Practice Guideline: Prevention of Blood Culture Contamination, Full Version," 2012 ENA Emergency Nurses Resources Development Committee, Emergency Nurses Association (Dec. 2012), 14 pages.

Schuur, J., "Blood Cultures: When Do they Help and When Do They Harm?" Brigham & Women's Hospital, Department of Emergency Medicine, (Jun. 21-23, 2012), 42 pages.

Sibley, C. D. et al., "Molecular Methods for Pathogen and Microbial Community Detection and Characterization: Current and Potential Application in Diagnostic Microbiology," Infection, Genetics and Evolution 12:505-521 (2012).

Stohl, S. et al., "Blood Cultures at Central Line Insertion in the Intensive Care Unit: Comparison with Peripheral Venipuncture," Journal of Clinical Microbiology, 49(7):2398-2403 (2011).

Wagner et al., "Diversion of Initial Blood Flow to Prevent Whole-Blood Contamination by Skin Surface Bacteria: an in vitro model," Transfusion, 40:335-338 (2000).

International Search Report and Written Opinion for International Application No. PCT/US2016/050380, dated Dec. 1, 2016, 6 pages.

Extended European Search Report for EP Application No. 15714987.3, dated Oct. 14, 2016, 2 pages.

* cited by examiner

APPARATUS AND METHODS FOR DISINFECTION OF A SPECIMEN CONTAINER

CROSS-REFERENCE TO RELATED APPLICATIONS

This application is a continuation of U.S. patent application Ser. No. 14/636,485, entitled, "Apparatus and Methods for Disinfection of a Specimen Container," filed Mar. 3, 2015 (now U.S. Pat. No. 10,123,783), which claims priority to and the benefit of U.S. Provisional Application Ser. No. 61/947,076, entitled, "Apparatus and Methods for Disinfection of a Specimen Container," filed Mar. 3, 2014, the disclosures of which are incorporated herein by reference in their entireties.

BACKGROUND

Embodiments described herein relate generally to the parenteral procurement of bodily-fluid samples, and more particularly to systems and methods for parenterally-procuring bodily-fluid samples with reduced contamination from microbes or other contaminants exterior to the bodily-fluid source that can potentially distort the results of diagnostic testing in a healthcare setting.

Health care practitioners routinely perform various types of microbial as well as other broad diagnostic tests on patients using parenterally-obtained bodily-fluids. As advanced diagnostic technologies evolve and improve, the speed and value of information that can be provided to clinicians continues to improve. As such, ensuring that the bodily-fluid sample to be analyzed is collected in a fashion that maintains specimen integrity similarly ensures that analytical diagnostic results are representative of the in vivo conditions of a patient. Examples of diagnostic technologies that are reliant on high quality, non-contaminated bodily-fluid samples include but are not limited to molecular diagnostics, genetic sequencing (e.g., DNA, RNA), and the like. When biological matter, cells external to the intended source for sample procurement, and/or other external contaminants are inadvertently included in the bodily-fluid sample that is to be analyzed, the opportunity for an adulterated specimen driving a potentially inaccurate patient diagnosis may occur.

In some instances, patient samples (e.g., bodily-fluids) are tested for the presence of one or more potentially undesirable microbes, such as bacteria, fungi, or yeast (e.g., *Candida*). Microbial testing may include incubating patient samples in one or more sterile and/or non-sterile vessels containing culture media or other types of solutions that are conducive to microbial growth and/or other real-time diagnostics including molecular polymerase chain reaction-based (PCR-based) technologies used to rapidly identify organisms. Generally, when microbes tested for are present in the patient sample, the microbes flourish over time in the culture medium. These organisms may also be identified by other advanced diagnostic testing technologies (e.g., molecular testing/diagnosing, PCR, genetic testing/sequencing, etc.). In the case of employing a culture medium, after an amount of time (e.g., a few hours to several days—which can sometimes be a longer or shorter depending on the diagnostic technology employed), organism growth can be detected by automated, continuous monitoring. For example, in some instances, such automated monitoring can detect carbon dioxide produced by organism growth. The presence of microbes in the culture medium (as indicated by observation of carbon dioxide) and/or via other detection methods suggests the presence of the same microbes in the patient sample which, in turn, suggests the presence of the same microbes in the bodily-fluid of the patient from which the sample was obtained. Accordingly, when microbes are determined to be present in the culture medium (or more generally in the sample used for testing), the patient may be prescribed one or more antibiotics or other treatments specifically designed to treat or otherwise remove the undesired microbes from the patient.

Generally, patient bodily-fluid samples are collected in various settings and are then transported to a laboratory-type environment for processing and analysis. For example, the settings for collecting the patient sample(s) could include an outpatient clinic, a hospital (including emergency department, intensive care unit (ICU), medical/surgical floor, or the like) or a commercial setting (including a drugstore or any other commercial enterprise that assists with collection of bodily-fluid sample(s)). In all settings, typically, protocols are developed, implemented, and monitored to ensure the quality of the collection, handling, preparation, transportation, etc. of a patient's bodily-fluid sample(s). Generally, practitioners ensure the integrity of the patient specimen(s), understanding that if the sample is adulterated and/or contains matter that is not representative of the patient's in vivo condition, a diagnostic error and ensuing inaccurate treatment decision(s) may occur.

In some instances, patient samples, nonetheless, can become contaminated during procurement. For example, some equipment used in phlebotomy procedures can include multiple fluidic interfaces (e.g., patient to needle, peripheral IV to catheter, needle/tubing to sample vessels, etc.) that can each introduce points of potential contamination. Additionally, the equipment used to procure, transfer, transport, and/or otherwise contain a patient sample are typically connected and/or otherwise placed in fluid communication via manual intervention (e.g., a doctor, phlebotomist, nurse, etc. handles and/or manipulates the equipment). Since the interfaces of the equipment are not consistently preassembled and/or sterilized as a single fluidically coupled system, external contaminants (e.g., microbes, dermally-residing organisms, cells from the patient that are not from the intended source of bodily-fluid to be tested, etc.) can be introduced to the patient sample via multiple sources (e.g. ambient air, contaminants on surfaces of tables and/or counters in patient room, microbes transferred from linens or clothing, skin deposited on collection supplies from a healthcare worker during assembly and/or sample procurement or transfer, cells from another source within the patient, and/or the like). In some instances, the contaminants can lead to a positive microbial and/or other diagnostic test result, thereby falsely indicating the presence of such microbes or other cells and/or other biological matter in vivo. Such inaccurate results are a concern when attempting to diagnose or treat a suspected illness or condition. For example, false positive results from microbial tests may result in the patient being unnecessarily subjected to one or more anti-microbial therapies, which may cause serious side effects to the patient including, for example, death, as well as produce an unnecessary burden and expense to the healthcare system.

As such, a need exists for improved systems and methods for disinfection of specimen container(s) that reduce microbial and/or any other type of contamination associated with the collection of bodily-fluid test samples by, for example, disinfecting equipment interfaces to ensure the integrity of the patient sample(s) that are collected and analyzed in the diagnostic process, thereby minimizing and/or substantially eliminating false positive as well as false negative diagnostic results.

SUMMARY

Apparatus and methods for parenterally-procuring bodily-fluid samples with reduced contamination from microbes exterior to the bodily-fluid source and/or other undesirable external contaminants or biological matter are described herein. In some embodiments, an apparatus includes a transfer adapter, a puncture member, a disinfection member, and a fluid reservoir. The transfer adapter has a proximal end portion and a distal end portion, and defines an inner volume configured to receive the puncture member. The transfer adapter is coupled to the disinfection member. The distal end portion of the transfer adapter includes a port fluidically coupled to the puncture member and configured to be placed in fluid communication with a bodily-fluid from a patient. The proximal end portion is configured to receive a portion of the fluid reservoir to allow the fluid reservoir to be moved within the inner volume between a first position, in which a surface of the fluid reservoir is placed in contact with the disinfection member, and a second position, in which the puncture member punctures the surface to place the puncture member in fluid communication with the fluid reservoir.

DETAILED DESCRIPTION

Figure 1:
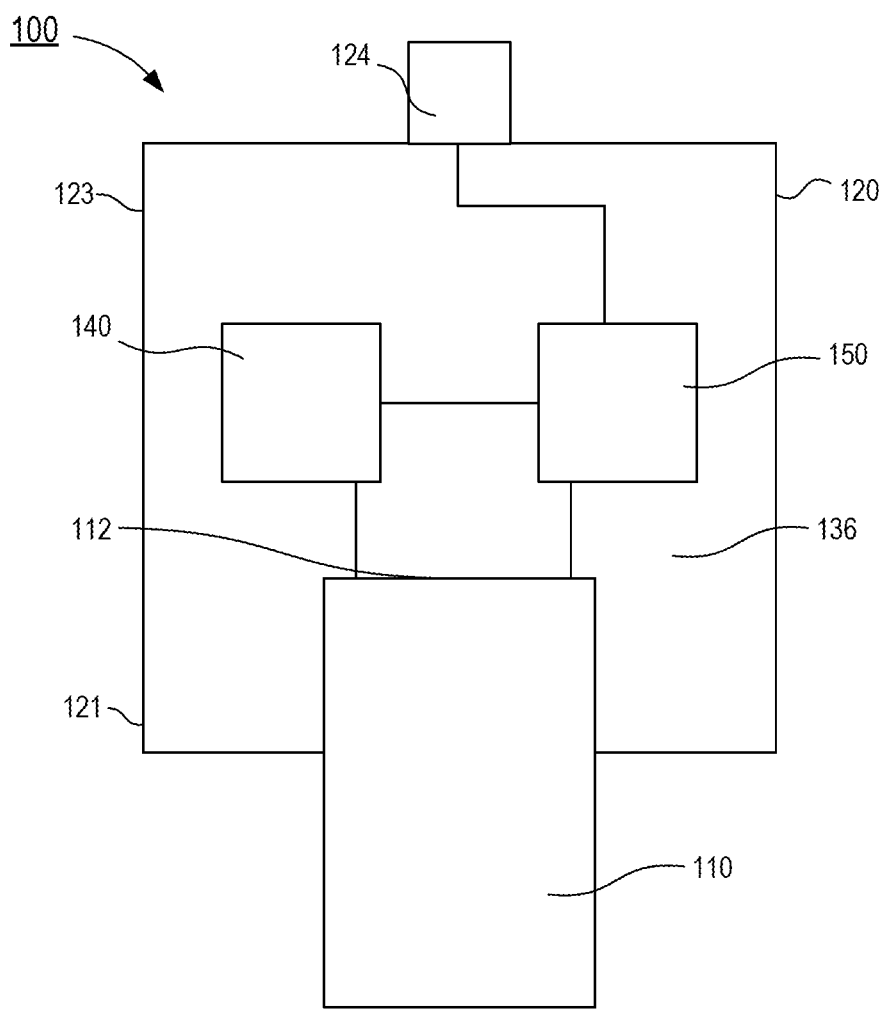
FIG. 1 is a schematic illustration of a bodily-fluid collection device, according to an embodiment.

In some embodiments, an apparatus includes a transfer adapter, a puncture member, and a disinfection member. The transfer adapter has a proximal end portion and a distal end portion, and defines an inner volume configured to receive the puncture member. The transfer adapter is coupled to the disinfection member. The distal end portion of the transfer adapter includes a port fluidically coupled to the puncture member and configured to be placed in fluid communication with a bodily-fluid of a patient. The proximal end portion is configured to receive a portion of a fluid reservoir to allow the fluid reservoir to be moved within the inner volume between a first position, in which a surface of the fluid reservoir is placed in contact with the disinfection member, and a second position, in which the puncture member punctures the surface to place the puncture member in fluid communication with the fluid reservoir.

In some embodiments, a method includes establishing fluid communication between a patient and a transfer adapter. The transfer adapter is coupled to a disinfection member. The transfer adapter defines an inner volume configured to house a puncture member. The puncture member is configured to be in fluid communication with the patient when the transfer adapter is placed in fluid communication with the patient. A portion of a fluid reservoir is inserted into the inner volume of the transfer adapter. The fluid reservoir is moved to a first position to place a contact surface of the fluid reservoir in contact with the disinfection member. The method includes moving the fluid reservoir to a second position. A portion of the fluid reservoir is moved within the inner volume when the fluid reservoir is moved to its second position such that the puncture member punctures the contact surface of the fluid reservoir to place the fluid reservoir in fluid communication with the patient. Optionally, in some embodiments, an intermediary device (e.g. a syringe) can be coupled to the transfer adapter to establish fluid communication and to collect a bodily-fluid sample. Following sample collection, the intermediary device can be, for example, coupled to the fluid reservoir to facilitate the transfer of the bodily-fluid. In some embodiments, the disinfection member can be placed in contact with one or more interfaces formed by the intermediary device and/or the transfer adapter to substantially sterilize the interfaces.

In some embodiments, a kit includes a package, a transfer adapter, a disinfection member, and a retainer. The package defines an inner volume and has an inner surface. The inner surface has a contour portion. The transfer adapter defines an inner volume configured to house a puncture member. The transfer adapter is configured to be moved from a first position, in which the transfer adapter is disposed within the package and in contact with the contour portion of the inner surface, to a second position, in which the transfer adapter is disposed substantially outside of the package. The transfer adapter and the contour portion form a friction fit when the transfer adapter is in its first position to at least temporarily retain the transfer adapter in a fixed position relative to the package. The disinfection member is configured to be moved from a first position, in which the disinfection member is disposed within the package and in contact with the inner surface, to a second position, in which the disinfection member is disposed substantially outside of the package. The retainer is configured to be disposed within the package and configured to be transitioned from a first configuration to a second configuration when the disinfection member is in its second position. The retainer substantially prevents the transfer adapter from being moved from its first position to its second position when the retainer is in the first configuration.

In some embodiments, the disinfection member is positioned during the manufacturing process in a position that prevents the clinician from collecting and/or transferring a bodily-fluid sample into a fluid reservoir(s) without engaging the disinfection member to at least substantially sterilize a connection therebetween, which in turn, facilitates fluid communication of a bodily-fluid sample between the patient and the collection vessel. By ensuring that substantially no external contaminants and/or biological matter (e.g., skin cells, tumor cells, organ tissue, etc.) external to the target bodily-fluid source are captured in the sample vessel, diagnostic results can improve with increased consistency. With accurate diagnostic results, clinicians can derive an accurate treatment/action plan, thereby reducing the likelihood of misdiagnosing a patient, prescribing unnecessary treatment, holding the patient in a clinical and/or hospital setting for an undue period of time, and/or the like, which in turn, can substantially reduce a risk of the patient developing a further ailment (e.g., antibiotic complications, adverse drug reactions, hospital-acquired infection, and/or the like) as well as substantially reduce costs to hospital and/or other healthcare institutions.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As referred to herein, "bodily-fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are in discontinuous from each other. A set of walls can also be fabricated from multiple items that are produced separately and are later joined together (e.g., via a weld, an adhesive or any suitable method).

As used herein, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the term "disinfecting agent" refers to a chemical or combination of chemicals used to disinfect and/or to substantially sterilize a surface. A disinfecting agent can be in any suitable form (e.g., gaseous, aqueous, or solid). In some embodiments, a disinfecting agent can be an antiseptic or the like that can be used to kill, destroy, and/or otherwise substantially neutralize negative effects from microbes such as, for example, germs, bacteria, viruses, and/or other target microorganisms. In some embodiments, a disinfecting agent can be in an aqueous form and substantially suspended by a porous substrate. In other embodiments, a surface of a substrate such as a wipe or diaphragm can be impregnated by and/or coated with a disinfecting agent. A non-limiting list of disinfecting agents can include, for example, alcohol (e.g., ethanol, 1-propanol, 2-proponal, isopropanol, and/or the like), quaternary ammonium compounds ((e.g., benzalkonium chloride (BAC), cetyl trimethylammonium bromide (CTMB), cetylpyridinium chloride (Cetrim (CPC)), benzethonium chloride (BZT) and/or the like), boric acid, chlorhexidine gluconate, hydrogen peroxide, iodine, octenidine dihydrochloride, phenol, polyhexanide (e.g., polyhexamethylene biguanide (PHMB)), sodium bicarbonate, silver compounds (e.g., silver nitrate, silver proteinate, chlorhexidine-silver-sulfadiazine, and/or the like), and/or any other suitable disinfectant or antiseptic, and/or a combination thereof. Moreover, any of the disinfecting agents can be used with, for example, a binding agent, a suspension agent, a surfactant, and/or the like.

FIG. 1 is a schematic illustration of a bodily-fluid collection device 100, according to an embodiment. Generally, the bodily-fluid collection device 100 (also referred to herein as "collection device") is configured to disinfect one or more interfaces prior to defining a fluidic coupling to reduce external contaminants residing on the interfaces. Once disinfected, the one or more interfaces can be fluidically coupled to allow a flow of bodily-fluid that is substantially free of external contaminants to flow from a patient to a fluid reservoir.

The collection device 100 includes a transfer adapter 120, a disinfection member 140, puncture member 150, and optionally, a fluid reservoir 110. The transfer adapter 120 has a proximal end portion 121 and a distal end portion 123, and defines an inner volume 136 therebetween. The transfer adapter 120 can be any suitable shape, size, or configuration. For example, the transfer adapter 120 can be substantially cylindrical, including a set of annular walls that define at least a portion of the inner volume 136. Moreover, as shown in FIG. 1, the transfer adapter 120 (and or the annular walls of the transfer adapter 120) can house at least a portion of the disinfection member 140 and the puncture member 150. In other words, the disinfection member 140 and the puncture member 150 are each disposed, at least partially, within the inner volume 136 defined by the transfer adapter 120, as described in further detail herein.

The proximal end portion 121 of the transfer adapter 120 can be substantially open to movably receive at least a portion of the fluid reservoir 110. More particularly, at least a portion of the fluid reservoir 110 can be inserted through the proximal end portion 121 of the transfer adapter 120 to dispose the portion of the fluid reservoir 110 within the inner volume 136. As described in further detail herein, the fluid reservoir 110 can be inserted through the proximal end portion 121 of the transfer adapter 120 and can be sequentially placed in a first position and a second position within the inner volume 136.

The distal end portion 123 of the transfer adapter 120 includes a port 124 that can be physically and fluidically coupled to any suitable lumen defining device such as a catheter, cannula, needle, trocar, or the like. For example, in some embodiments, the port 124 is a Luer Lok® that can be physically and fluidically coupled to a peripheral intravenous (IV) needle or a peripheral IV catheter, which can facilitate access to the bodily-fluid source. In addition, the port 124 can be in fluid communication with the puncture member 150 disposed within the inner volume 136. For example, in some embodiments, the port 124 and the puncture member 150 can be monolithically formed, defining a lumen that extends through a distal surface of the port 124 and a proximal surface of the puncture member 150. In other embodiments, the port 124 and the puncture member 150 can be operably coupled such that a lumen defined by the port 124 is in fluid communication with a lumen defined by the puncture member 150. Therefore, when the port 124 is fluidically coupled to the lumen defining device, the puncture member 150 is placed in fluid communication with the lumen defining device, as described in further detail herein.

Although not shown in FIG. 1, the transfer adapter 120 can include one or more seals that can be removably coupled to a surface of the transfer adapter 120 to fluidically isolate the inner volume 136 from a volume outside of the transfer adapter 120. For example, in some embodiments, the proximal end portion 121 of the transfer adapter 120 can include a seal and/or the like that can be removably coupled to a proximal surface of the transfer adapter 120 to substantially cover an opening defined by the proximal end portion 121 (described above). In this manner, the seal can fluidically isolate the inner volume 136 to substantially maintain the sterility of the inner volume 136. Moreover, by fluidically isolating the inner volume 136, in some embodiments, the seal can maintain a relative humidity within the inner volume 136, as described in further detail herein.

As described above, the disinfection member 140 is at least partially disposed within the inner volume 136 of the transfer adapter 120. The disinfection member 140 can be, for example, a pad, a swab, a diaphragm, a sponge, a wipe, and/or the like that can include a disinfecting agent. For example, in some embodiments, the disinfection member 140 can be a diaphragm or the like that can have at least one surface that is substantially impregnated with a disinfecting agent such as, those described above. In some embodiments, the disinfection member 140 can include and/or can define a portion that is substantially porous, for example, to act as a substrate for the disinfection agent. In other embodiments, the disinfection member 140 can include a surface that is substantially impregnated with the disinfection agent (e.g., coated with and/or the like). In still other embodiments, the disinfection member 140 can include a surface that is formed from a disinfecting material such as, for example, a silver compound. As described in further detail herein, when the fluid reservoir 110 is placed in its first position within the inner volume 136, the disinfection member 140 is placed in contact with a surface of the fluid reservoir 110 to substantially disinfect the surface.

As described above, in some embodiments, a seal can be removably coupled to the transfer adapter 120 to fluidically isolate the inner volume 136 from a volume outside of the transfer adapter 120. In some instances, by fluidically isolating the inner volume 136 a relative humidity can be maintained within the inner volume 136 that can, for example, substantially limit and/or prevent evaporation of the disinfection agent. For example, in some embodiments, the disinfection member 140 can be a porous substrate that can suspend, for example, an alcohol or chlorhexidine based disinfection agent that would otherwise evaporate, at least partially, in a relatively low humidity and/or non-sealed environment.

As described above, the puncture member 150 is at least partially disposed within the inner volume 136 of the transfer adapter 120. The puncture member 150 can be, for example, a lumen defining device that can include a sharpened end portion. For example, in some embodiments, the puncture member 150 can be a needle that can have a sharpened proximal end portion. As such, the puncture member 150 can be configured to puncture, pierce, and/or otherwise be inserted into the fluid reservoir 110 when the fluid reservoir 110 is placed in its second position within the inner volume 136, as described in further detail herein. Although not shown in FIG. 1, in some embodiments, the puncture member 150 can be disposed within a sheath or the like. In some instances, the sheath can be transitioned between a first configuration, in which the sheath substantially surrounds or encloses at least a portion of the puncture member 150, and a second configuration, in which at least a portion of the puncture member 150 extends beyond a distal surface of the sheath. Moreover, while in the first configuration, the sheath can fluidically isolate the puncture member 150 from a volume outside of the sheath to, for example, maintain sterility of the puncture member 150 prior to the sheath being transitioned to the second configuration, as described in further detail herein.

The fluid reservoir 110 can be any suitable shape, size, and/or configuration that can receive and/or store a volume of a bodily-fluid. For example, in some embodiments, the fluid reservoir 110 can be any suitable reservoir described in U.S. Pat. No. 8,197,420 ("the '420 patent"), entitled, "Systems and Methods for Parenterally Procuring Bodily-Fluid Samples with Reduced Contamination," filed on Dec. 13, 2007, the disclosure of which is incorporated herein by reference in its entirety. In some embodiments, the fluid reservoir 110 can define a negative pressure (e.g., can be substantially evacuated). In some embodiments, the fluid reservoir 110 can be, for example, a BacT/ALERT® SN or a BacT/ALERT® FA (manufactured by BIOMERIEUX, INC.), a BD Vacutainer® or a BD Microtainer® (manufactured Becton, Dickinson, and Company (BD)), a Nanotainer™ (manufactured by Theranos), and/or any suitable reservoir, vial, microvial, microliter vial, container, microcontainer, or the like. In some embodiments, the fluid reservoir 110 can be any suitable sample or culture bottle such as, for example, aerobic culture bottles, anaerobic culture bottles, and or the like that can include a culture medium or the like. In this manner, the culture bottle can receive a bodily-fluid sample, which can then be test for the presence of, for example, Gram-Positive bacteria, Gram-Negative bacteria, yeast, and/or any other organism and subsequently tested using, for example, a polymerase chain reaction (PCR)-based system to identify a specific organism. In some instances, the culture bottle can receive a bodily-fluid sample and the culture medium (disposed therein) can be tested for the presence of any suitable organism. If such a test of the culture medium yields a positive result, the culture medium can be subsequently tested using a PCR-based system to identify a specific organism. The fluid reservoir 110 includes a surface 112 that can be pierced to place an inner volume of the fluid reservoir 110 in fluid communication with a volume outside of the fluid reservoir 110. For example, in some embodiments, the surface 112 can include and/or can define a frangible portion and/or a port that can be pierced, for example, by the puncture member 150, as described in further detail herein.

In use, a user (e.g., a doctor, nurse, technician, physician, phlebotomist, etc.) can manipulate the collection device 100 to couple the port 124 to a lumen defining device such as, for example, a standard winged butterfly needle, a syringe, a peripheral IV catheter, and/or the like. In some instances, the lumen defining device can be placed in communication with a bodily-fluid in a patient prior to being coupled to the port 124. In other instances, the port 124 can be coupled to the lumen defining device prior the lumen defining device being inserted (e.g., percutaneously) into the patient. With the port 124 in fluid communication with the lumen defining device, the user can manipulate the collection device 100 to insert at least a portion of the fluid reservoir 110 to the proximal end portion 121 of the transfer adapter 120. In this manner, a fluid flow path can be defined between a flow of bodily-fluid within the patient and the lumen defined by the puncture member 150. In other words, the lumen defining device and the port 124 place the puncture member 150 in fluid communication with a flow of bodily-fluid in the patient. In some embodiments, prior to inserting the fluid reservoir 110, the user can manipulate the collection device 100 to remove, for example, a seal that substantially covers the proximal end, as described above.

The user can move the fluid reservoir 110 in a distal direction relative to the transfer adapter 120 to place the fluid reservoir 110 in the first position within the inner volume 136, thereby placing the collection device 100 in a first configuration. In this manner, the disinfection member 140 can be placed in contact with, for example, the surface 112 of the fluid reservoir 110 to substantially disinfect the surface 112. In some embodiments, the user can maintain the fluid reservoir 110 in the first position for a predetermined time period to allow the disinfection agent to disinfect the surface 112 of the fluid reservoir 110. Similarly stated, the user can place the fluid reservoir 110 in the first position and can hold the fluid reservoir 110 substantially in the first position to allow the disinfection member 140 to disinfect the surface 112 of the fluid reservoir 110. In other embodiments, the fluid reservoir 110 need not be held in the first position for the disinfection member 140 to disinfect the surface 112 of the fluid reservoir 110. For example, in some embodiments, the user can move the fluid reservoir 110 in the distal direction and in a substantially continuous manner to place the fluid reservoir 110 in the first position and then the second position.

While not shown in FIG. 1, in some embodiments, the collection device 100 can include one or more mechanical features that are configured to be manipulated by the user to place the surface 112 of the fluid reservoir 110 in contact with the disinfection member 140 in a predetermined and/or otherwise specific manner to ensure that proper time and technique are employed to substantially eliminate contaminants and/or microbes external to the patient's bodily-fluid source at the interface of the collection device 100 and fluid reservoir 110. For example, in some embodiments, the transfer adapter 120 can include and/or can define a set of threads incorporated into the annular walls (described above). In such embodiments, a user can twist the fluid reservoir 110 a predetermined number of times to place the fluid reservoir 110 in contact with the puncture member 150. In this manner, the twisting of the fluid reservoir 110 the predetermined number of times can assure that the surface 112 of the fluid reservoir 110 has been in contact with and/or has been scrubbed by the disinfection member 140 for a sufficient amount of time to achieve a desired sterility of the surface 112 of the fluid reservoir 110. Similarly, mechanical features can be integrated to ensure the surface 112 of the fluid reservoir 110 has sufficient time to dry (and hence opportunity for microbes and/or contaminants to die) following exposure to the disinfection agents contained on or in the disinfection member 140.

In some embodiments, the disinfection member 140 can be a diaphragm or the like that can be transitioned (e.g., opened or otherwise reconfigured) between a first configuration and a second configuration as the fluid reservoir 110 is moved from the first position toward the second position. In this manner, a surface of the disinfection member 140 can be placed in contact with the surface 112 of the fluid reservoir 110 when the fluid reservoir 110 is placed in the first position and can "wipe" the surface 112 of the fluid reservoir 110 as the fluid reservoir 110 is moved from the first position to the second position. In other embodiments, the disinfection member 140 can substantially remain in contact with the surface 112 of the fluid reservoir 110 when the fluid reservoir 110 is moved from the first position to the second position (e.g., the disinfection member 140 can compress or otherwise reconfigure to remain in contact with the surface 112).

The user can move the fluid reservoir 110 to the second position to place the puncture member 150 into contact with the surface 112, thereby placing the collection device in a second configuration. For example, as the fluid reservoir 110 is moved in the distal direction toward the second position, a proximal end portion of the puncture member 150 is placed in contact with a piercable portion of the surface 112 (e.g., a frangible seal). More particularly, the proximal end portion of the puncture member 150 can contact the surface 112 of the fluid reservoir 110 prior to the fluid reservoir 110 being placed in the second position such that further distal movement advances the surface 112 of the fluid reservoir 110 beyond the proximal portion of the puncture member 150. Thus, the puncture member 150 pierces the surface 112 to dispose a portion of the puncture member 150 in an inner volume defined by the fluid reservoir 110. Moreover, with the puncture member 150 defining a lumen and with the fluid reservoir 110 in the second position, the portion of the puncture member 150 can be disposed within the fluid reservoir 110 such that the lumen defined by the puncture member 150 is in fluid communication with the inner volume of the fluid reservoir 110.

As described above, in some embodiments, the fluid reservoir 110 can be configured to define a negative pressure that can exert a suction force in or on the lumen of the puncture member 150 when the puncture member 150 pierces surface 112 of the fluid reservoir 110. Thus, with the fluid flow path defined between the flow of bodily-fluid in the patient and the lumen defined by the puncture member 150 (e.g., via the lumen defining device and the port 124, as described above), the puncture member 150 can place the fluid reservoir 110 in fluid communication with the flow of bodily-fluid in the patient. As such, the negative pressure defined by the inner volume of the fluid reservoir 110 can exert a suction force within, for example, a vein of the patient to urge the bodily-fluid to flow within the fluid flow path to be disposed in the inner volume of the fluid reservoir 110. In some instances, the bodily-fluid can flow within the fluid flow path until a pressure within the inner volume of the fluid reservoir 110 is substantially equal to a pressure within, for example, the vein of the patient (or body of an intermediary collection device such as a syringe). In some instances, the bodily-fluid can flow within the fluid flow path until a predefined volume of the bodily-fluid is disposed within the fluid reservoir 110. With the desired amount of bodily-fluid disposed in the fluid reservoir 110, the fluid reservoir 110 can be moved in the proximal direction to, for example, remove the fluid reservoir 110 from the inner volume 136 of the transfer adapter 120. In some instances, a second fluid reservoir (not shown in FIG. 1) can be inserted into the transfer adapter 120 and placed in fluid communication with the flow of bodily-fluid in the patient in substantially the same manner as described above. Thus, any suitable number of fluid reservoirs can be inserted into the transfer adapter 120 such that a piercable surface of each fluid reservoir is disinfected prior to receiving a flow of bodily-fluid. As such, the amount of contaminants and/or microbes transferred to a bodily-fluid sample from, for example, a piercable surface of a fluid reservoir can be reduced and/or substantially eliminated.

In some embodiments, the collection device 100 can be included in and/or can form at least a portion of a preassenibled and/or all-in-one collection device. In such embodiments, the preassembled and/or all-in-one collection device can include, for example, any suitable number of fluid reservoirs (e.g., one fluid reservoir, two fluid reservoirs, three fluid reservoirs, four fluid reservoirs, or more) that can be preassembled with and/or incorporated in (e.g., unitarily formed with) a transfer device including a disinfection member such as those described herein. By way of example, in some embodiments, the collection device 100 (and/or any suitable portion thereof) can be included in and/or can otherwise form a portion of a preassembled and/or all-in-one collection device such as those described in U.S. patent application Ser. No. 14/096,826 entitled, "Sterile Bodily-Fluid Collection Device and Methods," filed Dec. 4, 2013 the disclosure of which is incorporated herein by reference in its entirety.

FIGS. 2-8 illustrate a bodily-fluid collection device 200, according to another embodiment. Generally, the bodily-fluid collection device 200 (also referred to herein as "collection device") is configured to disinfect one or more interfaces prior to defining a fluidic coupling to reduce external contaminants residing on the interfaces. Once disinfected, the one or more interfaces can be fluidically coupled to allow a flow of bodily-fluid that is substantially free of external contaminants to flow from a patient to a fluid reservoir.

Figure 2:
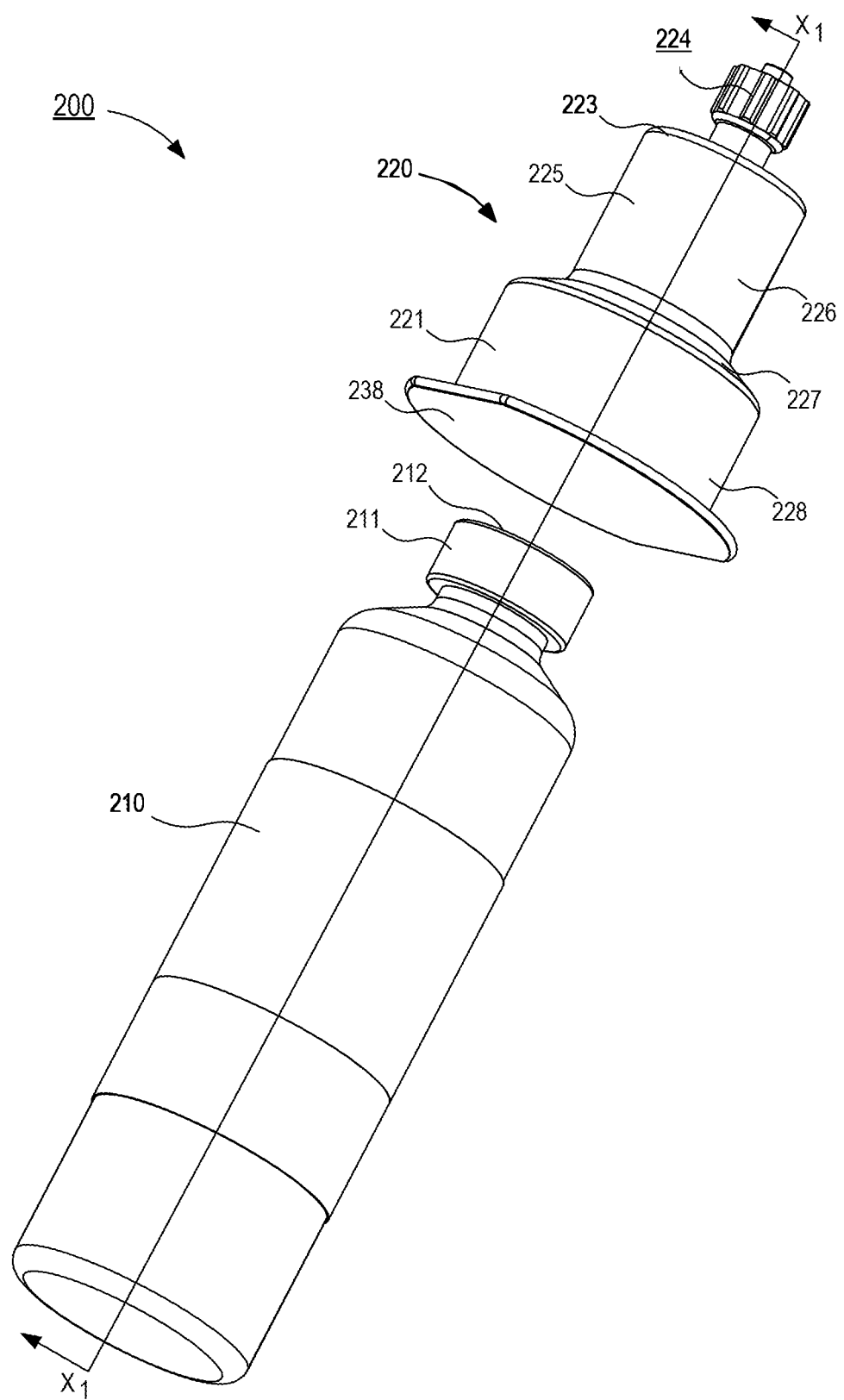
FIG. 2 is a perspective view of a bodily-fluid collection device, according to another embodiment.
Figure 3:
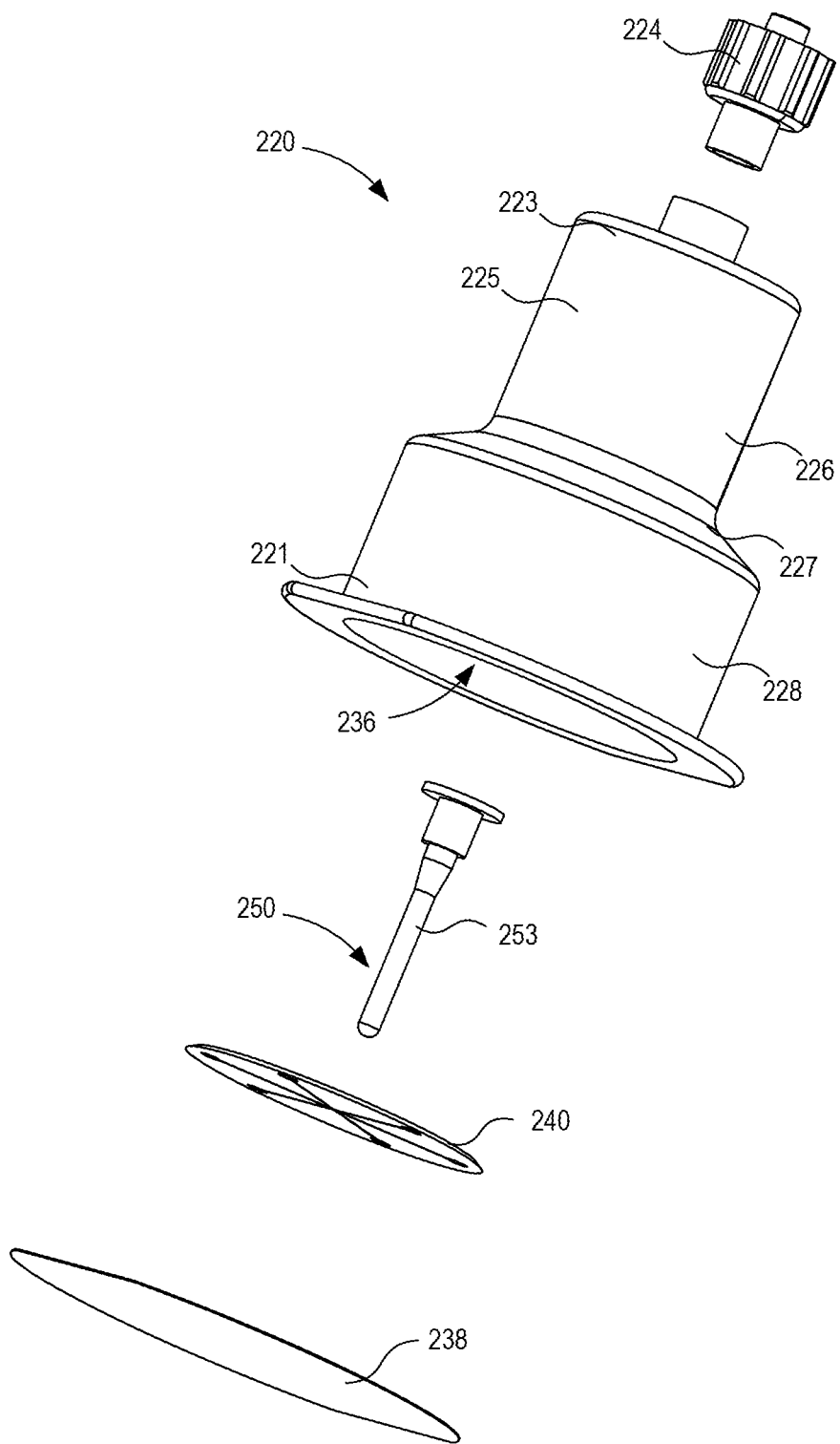
FIG. 3 is an exploded perspective view of a transfer adapter included in the bodily-fluid collection device of FIG. 2.

The collection device 200 includes a transfer adapter 220, a disinfection member 240 (see e.g., FIG. 3), a puncture member 250 (see e.g., FIG. 3), and a fluid reservoir 210. As shown in FIGS. 2 and 3, the transfer adapter 220 has a proximal end portion 221 and a distal end portion 223, and defines an inner volume 236 therebetween. The transfer adapter 220 can be any suitable shape, size, or configuration. For example, the transfer adapter 220 can have a set of annular walls 225 that define at least a portion of the inner volume 236. The annular walls 225 of the transfer adapter 220 house at least a portion of the disinfection member 240 and the puncture member 250. In other words, the disinfection member and the puncture member 250 are each at least partially disposed within the inner volume 236 defined by the transfer adapter 220. Moreover, at least a portion of the fluid reservoir 210 can be selectively disposed within the inner volume 236, as described in further detail herein.

The annular walls 225 can include a first cylindrical portion 226 (also referred to herein as "first portion"), a second cylindrical portion 228 (also referred to herein as "second portion"), and a tapered portion 227 disposed therebetween. More specifically, the arrangement of the annular walls 225 can be such that a diameter of the first portion 226 is smaller than a diameter of the second portion 228. Thus, a diameter of the tapered portion 227 decreases as the tapered portion 227 extends from the second portion 228 to the first portion 226. Said another way, the tapered portion 227 can have a diameter substantially equal to the diameter of the second portion 228 at a proximal end, and can have a diameter substantially equal to the diameter of the first portion 226 at a distal end. Accordingly, a diameter of a portion of the inner volume 236 (e.g., an inner diameter) can substantially correspond to the diameter of the portion of the annular walls 225 (e.g., an outer diameter), as described in further detail herein.

The proximal end portion 221 of the transfer adapter 220 can be substantially open (see e.g., FIG. 3) to movably receive at least a portion of the fluid reservoir 210. Said another way, at least a portion of the fluid reservoir 210 can be inserted through an opening defined by the proximal end portion 221 of the transfer adapter 220 to dispose the portion of the fluid reservoir 210 within the inner volume 236. As described in further detail herein, the fluid reservoir 210 can be inserted through the proximal end portion 221 of the transfer adapter 220 and can be placed in a first position (e.g., a proximal position) and a second position (e.g., a distal position) within the inner volume 236.

The distal end portion 223 of the transfer adapter 220 includes a port 224 that can be physically and fluidically coupled to any suitable lumen defining device such as a catheter, cannula, needle, trocar, or the like. For example, in some embodiments, the port 224 is a Luer Lok® that can be physically and fluidically coupled to a peripheral intravenous (IV) needle. In addition, the port 224 can be in fluid communication with the puncture member 250 disposed within the inner volume 236. For example, in some embodiments, the port 224 and the puncture member 250 can be monolithically formed, defining a lumen that extends through a distal surface of the port 224 and a proximal surface of the puncture member 250. In other embodiments, the port 224 and the puncture member 250 can be operably coupled such that a lumen defined by the port 224 is in fluid communication with a lumen defined by the puncture member 250. Therefore, when the port 224 is fluidically coupled to the lumen defining device, the puncture member 250 is placed in fluid communication with the lumen defining device, as described in further detail herein.

As shown in FIGS. 2 and 3, the transfer adapter 220 includes a seal 238 that can be removably coupled to, for example, a proximal surface of the transfer adapter 220 to fluidically isolate the inner volume 236 from a volume outside of the transfer adapter 220. The seal 238 can be any suitable configuration. For example, in some embodiments, the seal 238 is a substantially impermeable membrane that can include a portion configured to removably adhere to the proximal surface of the transfer adapter 220 (e.g., via an applied adhesive or via a self-adhesive property of the material forming the seal 238). In this manner, the seal 238 can fluidically isolate the inner volume 236 to substantially maintain the sterility of the inner volume 236 and/or the puncture member 250 and disinfection member 240 disposed therein. Moreover, by fluidically isolating the inner volume 236, the seal 238 can maintain a relative humidity within the inner volume 236 that is sufficient to substantially prevent evaporation of a disinfection agent disposed therein, as described in further detail herein.

Figure 4:
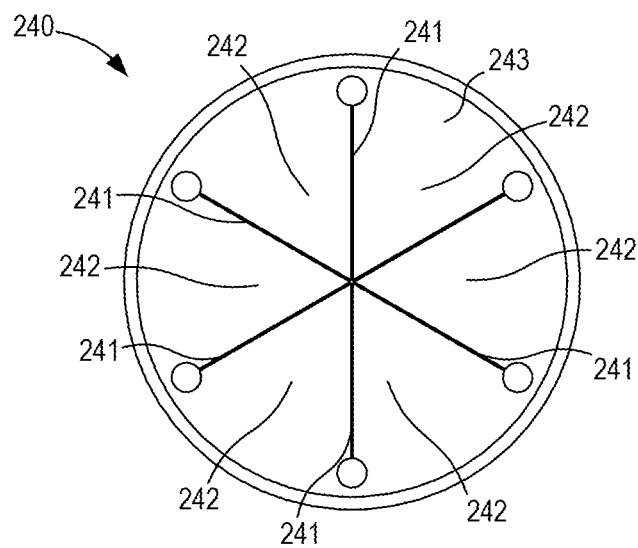
FIG. 4 is a top view of a disinfection member included in the transfer adapter of FIG. 3.

As described above, the disinfection member 240 is at least partially disposed within the inner volume 236 of the transfer adapter 220. The disinfection member 240 can be any suitable shape, size, or configuration. For example, as shown in FIGS. 3 and 4, the disinfection member 240 is a diaphragm or the like that can have a surface 243 that is substantially impregnated with a disinfecting agent such as, those described above. In other embodiments, the disinfection member 240 can include a surface 243 that is formed from and/or coated with a disinfecting material such as, for example, a silver compound. In some embodiments, substantially the entire disinfection member 240 can be formed from and/or coated with the disinfecting material.

As shown in FIG. 4, the disinfection member 240 defines a set of cuts 241 that at least partially form a set of fingers or flaps 242. The cuts 241 extend substantially through the disinfection member 240. In this manner, a force can be exerted on, for example, the surface 243 of the disinfection member 240 that is sufficient to move, separate, and/or otherwise reconfigure the fingers 241, as described in further detail herein. Furthermore, the cuts 241 each include an end portion that is configured to reduce tearing of the disinfection member 240 when the fingers 241 are moved relative to one another. For example, as shown in FIG. 4, the cuts 241 define an end portion with a substantially circular hole that can, for example, reduce stress concentration risers that could otherwise lead to tearing of the disinfection member 240 when the fingers 241 were moved relative to one another.

Although shown in FIG. 4 as defining six cuts 241 that form six fingers 242, in other embodiments, a disinfection member can include more than six cuts to form more than six fingers or less than six cuts to form less than six fingers. For example, a disinfection member can include four cuts that at least partially form four fingers. In other embodiments, a disinfection member can include eight cuts that at least partially form eight fingers. Moreover, although the disinfection member 240 in FIG. 4 is shown as being substantially symmetrical, in other embodiments, a disinfection member can include a set of cuts and fingers than are different shapes, sizes, lengths, position relative to the center as well as other fingers (e.g. not symmetrical), etc.

Figure 6:
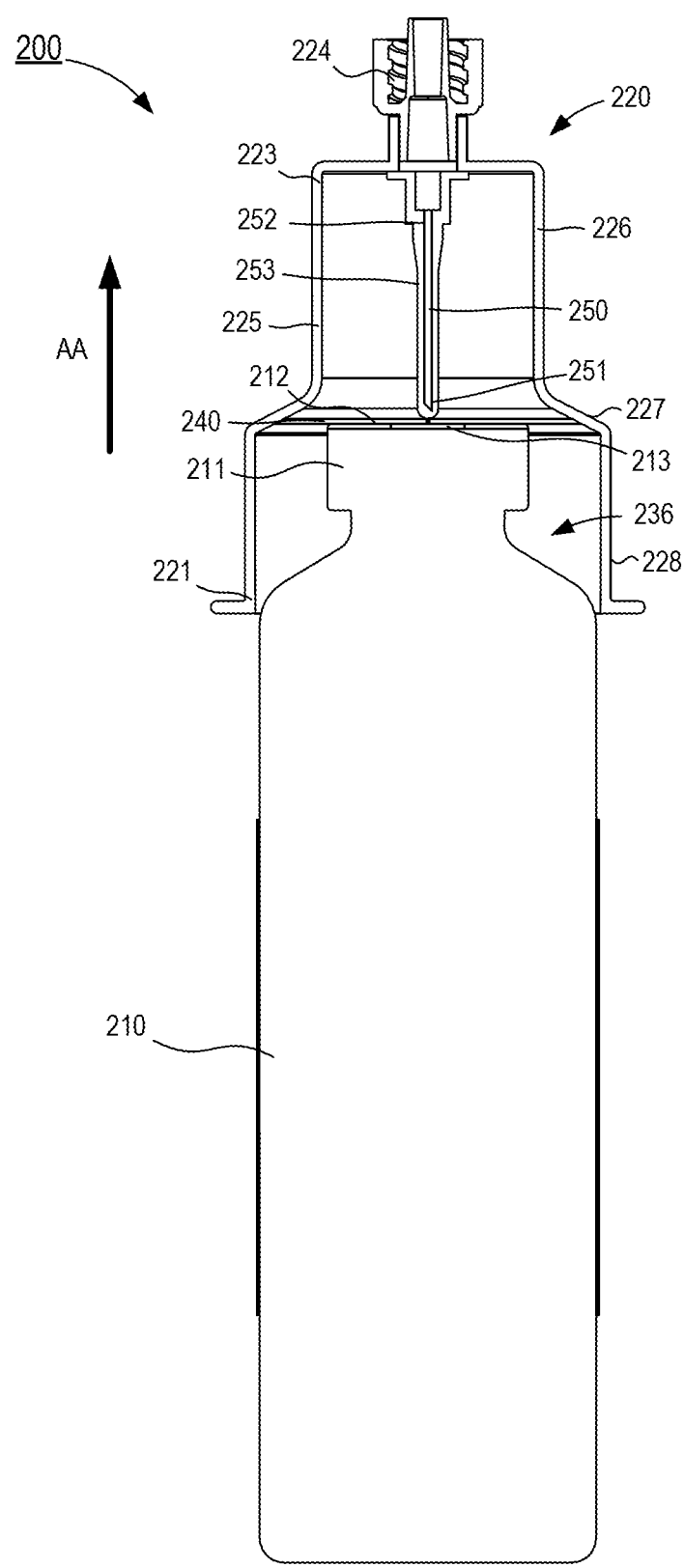
FIG. 6 is a cross-sectional side view of the bodily-fluid collection device of FIG. 2 taken along the line $X_1$-$X_1$, in a first configuration.

As shown, for example, in FIG. 6, the disinfection member 240 can be disposed within the inner volume 236 of the transfer adapter 220. More particularly, in some embodiments, the disinfection member 240 can be coupled to an inner surface of the annular walls 225. In some embodiments, the disinfection member 240 can define a friction fit with the inner surface of the annular walls 225 to substantially retain the disinfection member 240 in a substantially fixed position within the inner volume 236 (e.g., along the tapered portion 227 as shown in FIG. 6). In some embodiments, the disinfection member 240 can be coupled to the inner surface via an adhesive or the like. Although shown in FIG. 6 as being disposed at or along the tapered portion 227, in other embodiments, the disinfection member 240 can be disposed at or along the second portion 228 or at or along the third portion 226. As described in further detail herein, when the fluid reservoir 210 is placed in its first position within the inner volume 236, the surface 243 of the disinfection member 240 is placed in contact with a surface of the fluid reservoir 210 to substantially disinfect the surface.

As described above, in some embodiments, a seal 238 (FIGS. 2 and 3) can be removably coupled to the transfer adapter 220 to fluidically isolate the inner volume 236 from a volume outside of the transfer adapter 220. In some instances, by fluidically isolating the inner volume 236 a relative humidity can be maintained within the inner volume 236 that can, for example, substantially limit and/or prevent evaporation of the disinfection agent. For example, in some embodiments, the disinfection member 240 can be a diaphragm formed from a porous material that can be a substrate to suspend, for example, an alcohol and/or chlorhexidine based disinfection agent that would otherwise evaporate, at least partially, in a relatively low humidity and/or non-sealed environment.

As shown, for example, in FIG. 6, the puncture member 250 is at least partially disposed within the inner volume 236 of the transfer adapter 220. The puncture member 250 includes a proximal end portion 251 and a distal end portion 252. The puncture member 250 can be, for example, a lumen defining device such as a needle, catheter, cannula, and/or the like. The distal end portion 252 of the puncture member 250 can be physically and fluidically coupled to the port 224 of the transfer adapter 220. Moreover, as shown in FIG. 6, the puncture member 250 can extend in a proximal direction from the port 243 toward the disinfection member 240. The proximal end portion 251 of the puncture member 250 can include a sharpened tip or the like that can be configured to puncture, pierce, and/or otherwise be inserted into the fluid reservoir 210 when the fluid reservoir 210 is placed in its second position within the inner volume 236, as described in further detail herein.

As shown, the puncture member 250 is at least temporarily disposed within a sheath 253. The sheath 253 can be any suitable member that is configured to surround and/or enclose at least a portion of the puncture member 250. In some embodiments, the sheath 253 can be formed from a material that can be deformed, compressed, and/or otherwise reconfigured. For example, in some embodiments, the sheath 253 can be transitioned between a first configuration, in which the sheath 253 substantially surrounds or encloses at least a portion of the puncture member 250 (see e.g., FIG. 6), and a second configuration, in which at least a portion of the puncture member 250 extends beyond a distal surface of the sheath 253 (see e.g., FIG. 8). Moreover, the sheath 253 can be formed from a substantially impermeable material that can fluidically isolate a volume inside of the sheath 253 from a volume outside of the sheath 253. As such, the sheath 253 can fluidically isolate the puncture member 250 from a volume outside of the sheath 253 when in the first configuration to maintain sterility of the puncture member 250 prior to the sheath 253 being transitioned to the second configuration, as described in further detail herein. The sheath 253 can also be configured to function as a safety feature to prevent unintended needle-stick injuries to healthcare workers and/or patients during the preparation, execution, and/or post-procedure activities that involve handling the transfer adapter.

Figure 5:
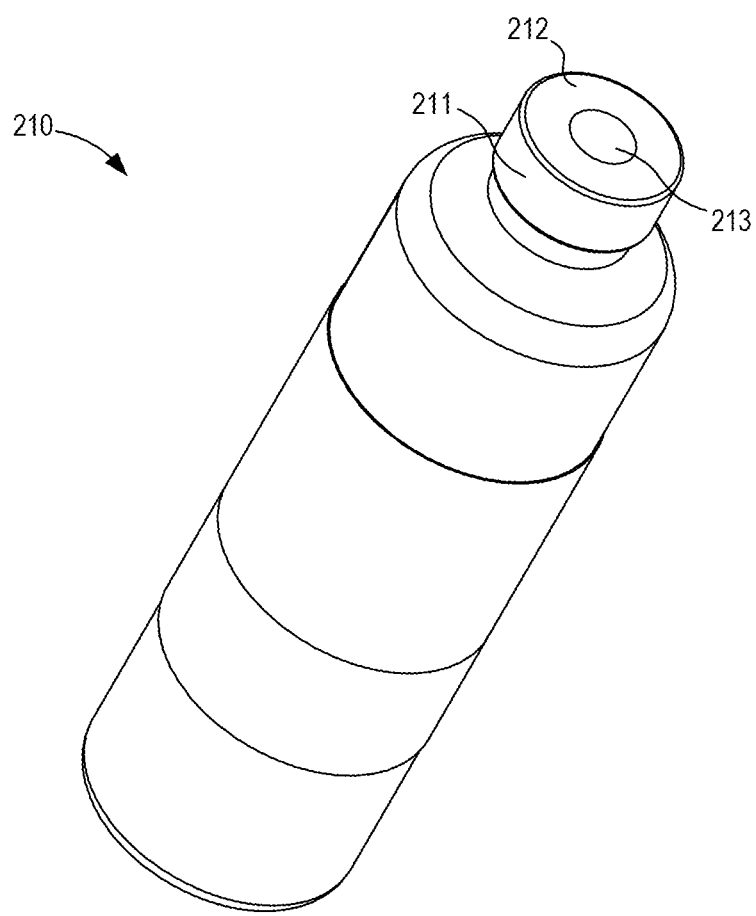
FIG. 5 is a top perspective view of a fluid reservoir included in the collection device of FIG. 2.

As shown in FIG. 5, the fluid reservoir 210 included in the collection device 200 can be substantially cylindrical and can be configured to receive and/or store a volume of a bodily-fluid. For example, in some embodiments, the fluid reservoir 210 can be any suitable reservoir described in the '420 patent incorporated by reference above. In some embodiments, the fluid reservoir 210 can define a negative pressure (e.g., can be substantially evacuated). In some embodiments, the fluid reservoir 210 can be, for example, a BacT/ALERT® SN or a BacT/ALERT® FA (manufactured by BIOMERIEUX, INC.), a BD Vacutainer® or a BD Microtainer® (manufactured Becton, Dickinson, and Company (BD)), a Nanotainer™ (manufactured by Thermos), and/or any suitable reservoir, vial, microvial, microliter vial, container, microcontainer, or the like. In some embodiments, the fluid reservoir 110 can be any suitable sample or culture bottle such as, for example, aerobic culture bottles, anaerobic culture bottles, and or the like that can include a culture medium or the like. In this manner, the culture bottle can receive a bodily-fluid sample, which can then be test for the presence of, for example, Gram-Positive bacteria, Gram-Negative bacteria, yeast, and/or any other organism and subsequently tested using, for example, a PCR-based system to identify a specific organism. In some instances, the culture bottle can receive a bodily-fluid sample and the culture medium (disposed therein) can be tested for the presence of any suitable organism. If such a test of the culture medium yields a positive result, the culture medium can be subsequently tested using a PCR-based system to identify a specific organism.

The fluid reservoir 210 includes a distal end portion 211 that can form, for example, a neck or the like. The distal end portion 211 includes a distal surface 212 that can include and/or the can form a port 213. For example, in some embodiments, the port 213 can be a self closing port or the like that can be transitioned between a substantially closed configuration, in which an inner volume defined by the fluid reservoir 210 is fluidically isolated from a volume outside of the fluid reservoir 210, and an open configuration, in which the inner volume of the fluid reservoir 210 is placed in fluid communication with a volume outside of the fluid reservoir 210. In some instances, the port 213 can be transitioned between the closed position and the open configuration by advancing the puncture member 250 through the port 213 (e.g., the proximal end portion 251 of the puncture member 250 pierces the port 213), and can be transitioned from the open configuration to the closed configuration by retracting the puncture member 250, as described in the further detail herein.

In use, a user (e.g., a doctor, nurse, technician, physician, phlebotomist, etc.) can manipulate the collection device 200 to couple the port 224 to a lumen defining device such as, for example, a peripheral IV and/or a standard winged butterfly needle, as described above. The lumen defining device can be placed in communication with a bodily-fluid in a patient to define a fluid flow path between a flow of the bodily-fluid within the patient and the lumen defined by the puncture member 250. In other words, the lumen defining device and the port 224 place the puncture member 250 in fluid communication with a flow of bodily-fluid in the patient. With the port 224 coupled to the lumen defining device, the user can manipulate the collection device 200 remove the seal 238 from the transfer adapter 220. For example, in some embodiments, the user can peel the seal 238 away from the proximal surface of the transfer adapter 220. Although described as removing the seal 238 after coupling the port 224 to the lumen defining device, in other instances, the user can manipulate the collection device 200 to remove the seal 238 prior coupling the port 224 to the lumen defining device.

The user can move the fluid reservoir 210 in a distal direction relative to the transfer adapter 220 to place the fluid reservoir 210 in the first position within the inner volume 236, thereby placing the collection device 200 in a first configuration, as indicated by the arrow AA in FIG. 6. In this manner, the disinfection member 240 can be placed in contact with the surface 212 of the fluid reservoir 210 to substantially disinfect the surface 212. In some embodiments, the user can maintain the fluid reservoir 210 in the first position for a predetermined time period to allow the disinfection agent to disinfect the surface 212 of the fluid reservoir 210. Similarly stated, the user can place the fluid reservoir 210 in the first position and can hold the fluid reservoir 210 substantially in the first position to allow the disinfection member 240 to disinfect the surface 212 of the fluid reservoir 210. In other embodiments, the fluid reservoir 210 need not be held in the first position for the disinfection member 240 to disinfect the surface 212 of the fluid reservoir 210. For example, in some embodiments, the user can move the fluid reservoir 210 in the distal direction and in a substantially continuous manner to place the fluid reservoir 210 in the first position and then the second position.

Figure 7:
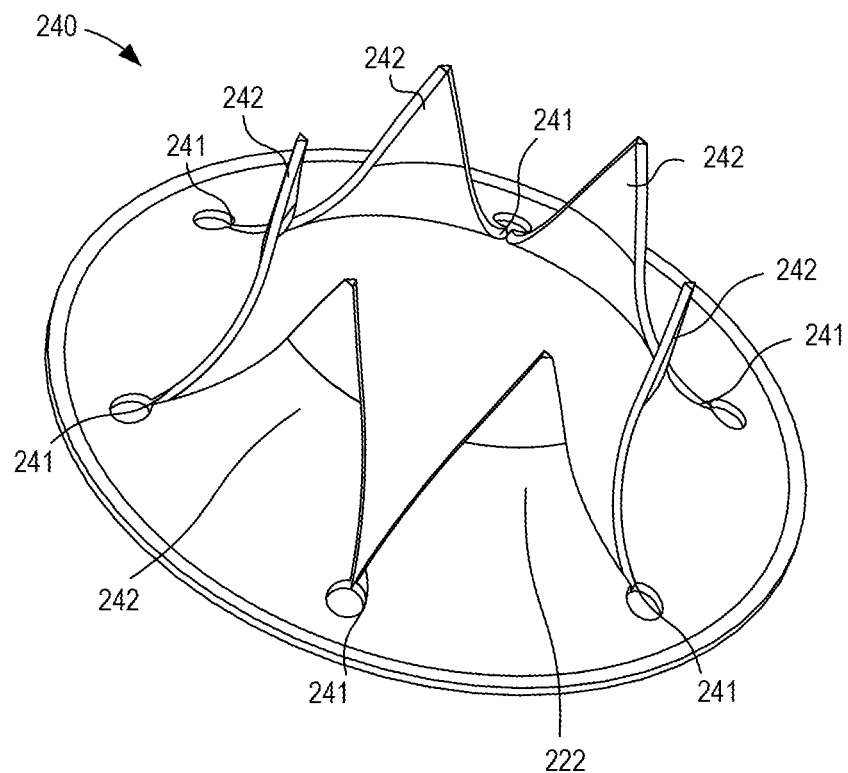
FIG. 7 is a perspective view of the disinfection member of FIG. 4 in a second configuration.

As described above, the disinfection member 240 can be transitioned (e.g., opened or otherwise reconfigured) between the first configuration and the second configuration as the fluid reservoir 210 is moved from the first position toward the second position. In this manner, the surface 243 of the disinfection member 240 can be placed in contact with the surface 212 of the fluid reservoir 210 when the fluid reservoir 210 is placed in the first position and can "wipe" the surface 212 of the fluid reservoir 210 as the fluid reservoir 210 is moved from the first position to the second position. Moreover, as shown in FIG. 7, as the fluid reservoir 210 is advanced in the distal direction beyond the disinfection member 240, the fingers 242 of the disinfection member 240 can deform, bend, and/or otherwise reconfigure to allow the fluid reservoir 210 to pass in a distal direction beyond the disinfection member 240.

Figure 8:
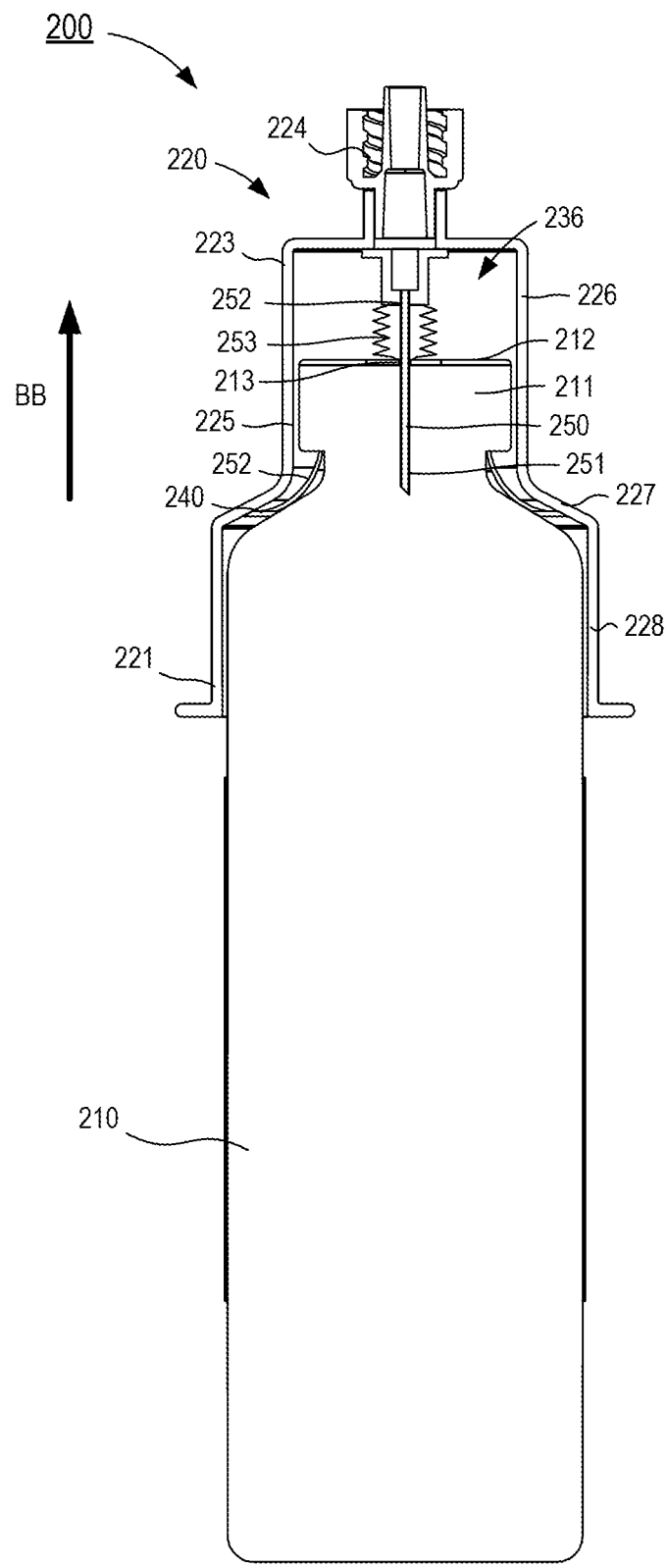
FIG. 8 is a cross-sectional view of the bodily-fluid collection device of FIG. 2 taken along the line $X_1$-$X_1$, in a second configuration.

The user can move the fluid reservoir 210 to the second position to place the puncture member 250 into contact with the surface 212, thereby placing the collection device 200 in a second configuration, as indicated by the arrow BB in FIG. 8. For example, as the fluid reservoir 210 is moved in the distal direction toward the second position, the proximal end portion 251 of the puncture member 250 is placed in contact with the port 213 included in and/or defined by the surface 212. Similarly stated, the proximal end portion 251 of the puncture member 250 can contact the port 213 of the fluid reservoir 210 prior to the fluid reservoir 210 being placed in the second position such that further distal movement of the fluid reservoir 210 (e.g., to or towards the second position) advances the surface 212 of the fluid reservoir 210 beyond the proximal end portion 251 of the puncture member 250. Moreover, the distal movement of the fluid reservoir 210 toward the second position can transition the sheath 253 substantially surrounding the puncture member 250 from its first configuration to its second configuration. For example, as described above, the sheath 253 can be formed from a deformable material that can be configured to bend, fold, compress, deflect, and/or otherwise deform when exposed to a force. Therefore, as the fluid reservoir 210 is advanced in the distal direction toward the second position, the surface 212 exerts a force on the sheath 253 that is sufficient to transition the sheath 253 from its first configuration to its second configuration, as shown in FIG. 8. Thus, the distal end portion 251 of the puncture member 250 can extend beyond the sheath 253 to pierce the port 213 of the fluid reservoir 210 such that a portion of the puncture member 250 is disposed in an inner volume defined by the fluid reservoir 210.

With the puncture member 250 defining a lumen and with the fluid reservoir 210 in the second position, the portion of the puncture member 250 can be disposed within the fluid reservoir 210 such that the lumen defined by the puncture member 250 is in fluid communication with the inner volume of the fluid reservoir 210. Thus, with the fluid flow path defined between the flow of bodily-fluid in the patient and the lumen defined by the puncture member 250 (e.g., via the lumen defining device and the port 224, as described above), the puncture member 250 can place the fluid reservoir 210 in fluid communication with the flow of bodily-fluid in the patient. As described above, the fluid reservoir 210 can define a negative pressure that can exert a suction force in or on the lumen of the puncture member 250 when the puncture member 250 pierces the fluid reservoir 210. In turn, the negative pressure defined by in the inner volume of the fluid reservoir 210 can exert a suction force within, for example, a vein of the patient to urge the bodily-fluid to flow within the fluid flow path to be disposed in the inner volume of the fluid reservoir 210. In some instances, the bodily-fluid can flow within the fluid flow path until a desired volume of bodily-fluid is disposed in the fluid reservoir 210, as described above. With the desired amount of bodily-fluid disposed in the fluid reservoir 210, the fluid reservoir 210 can be moved in the proximal direction to, for example, remove the fluid reservoir 210 from the inner volume 236 of the transfer adapter 220. In some instances, a second fluid reservoir (not shown) can be inserted into the transfer adapter 220 and placed in fluid communication with the flow of bodily-fluid in the patient in substantially the same manner as described above. Thus, any suitable number of fluid reservoirs can be inserted into the transfer adapter 220 such that a piercable surface of each fluid reservoir is disinfected prior to receiving a flow of bodily-fluid. As such, the amount of contaminants and/or microbes transferred to a bodily-fluid sample from, for example, a piercable surface of a fluid reservoir can be reduced and/or substantially eliminated.

As shown in FIG. 8, arrangement of the annular walls 225 of the transfer adapter 220 is associated with the general shape of the fluid reservoir 210. For example, the first portion 226, the second portion 228, and the tapered portion 227 of the annular walls 225 are arranged to substantially correspond to a shape of the fluid reservoir 210 when the fluid reservoir 210 is in the second position. In some embodiments, the smaller diameter of the first portion 226 of the annular walls 225 can, for example, reduce material usage and/or facilitate the handling of the transfer adapter 220. In some embodiments, the arrangement of the first portion 226 and the tapered portion 227 can substantially limit the movement of the fluid reservoir 210 in the distal direction. For example, in some embodiments, when the fluid reservoir 210 is in the second configuration, a surface of the fluid reservoir 210 can be placed in contact with the tapered portion 227 of the transfer adapter 220. In this manner, the tapered portion 227 can substantially limit any addition movement of the fluid reservoir 210 in the distal direction relative to the transfer adapter 210. In some embodiments, limiting the distal movement of the fluid reservoir 210 can substantially prevent and/or limit damage to, for example, the port 213 due to an undesirable force being exerted on the port 213 by a surface of the transfer adapter 220 and/or the puncture member 250.

Although the collection device 200 is described above as being coupled to the lumen defining device such as, for example, a peripheral IV and/or a standard winged butterfly needle, in other embodiments, the collection device 200 can be coupled to any suitable intermediate device. For example, in some embodiments, the collection device 200 can be physically and fluidically coupled to a diversion device and/or mechanism that is, in turn, physically and fluidically coupled to the peripheral IV and/or the standard winged butterfly needle. The diversion device and/or mechanism can be any suitable device such as, for example, those described in U.S. Pat. No. 8,535,241 entitled, "Fluid Diversion Mechanism for Bodily-Fluid Sampling," filed Oct. 12, 2012, the disclosure of which is incorporated herein by reference in its entirety. As such, the user can manipulate the diversion device and/or mechanism to divert a pre-sample volume of bodily-fluid into, for example, a pre-sample reservoir or the like. In some instances, the pre-sample reservoir can be configured to receive and fluidically isolate the pre-sample volume of bodily-fluid, which can contain external contaminants and/or microbes that otherwise can be transferred to the fluid reservoir 210. Once the pre-sample volume is fluidically isolated, the user can manipulate the diversion device and/or mechanism such that a sample volume of bodily-fluid can flow through the diversion device and/or mechanism and the collection device 200 to be disposed in the fluid reservoir 210.

FIGS. 9-12 illustrate a bodily-fluid collection device 300, according to another embodiment. Generally, the bodily-fluid collection device 300 (also referred to herein as "collection device") is configured to disinfect one or more interfaces prior to defining a fluidic coupling to reduce external contaminants residing on the interfaces. Once disinfected, the one or more interfaces can be fluidically coupled to allow a flow of bodily-fluid that is substantially free of external contaminants to flow from a patient or an intermediary transfer device (e.g. a syringe) to a fluid reservoir.

The collection device 300 includes a transfer adapter 320, a disinfection member 340 (see e.g., FIGS. 9 and 10), a puncture member 350 (see e.g., FIGS. 10-12), and a fluid reservoir 310. Some aspects of the collection device 300 can be similar in form and function as corresponding aspects of the collection device 200, described above with reference to FIGS. 2-8. For example, the disinfection member 340 can be substantially similar in form and function as the disinfection member 240 described above. In this manner, the disinfection member 340 includes a set of fingers 342 that can deform to transition the disinfection member 340 between a first configuration and a second configuration in substantially the same manner as described above. The puncture member 350 can be substantially similar in form and function as the puncture member 250 described above. In this manner, the puncture member 350 can include a proximal end portion 351 and a distal end portion 352 and can pierce a surface of the fluid reservoir 310, as described above with reference to the puncture member 250 (see e.g., FIG. 6). Moreover, the puncture member 350 can be at least temporarily disposed within a sheath 353 that can be substantially similar to the sheath 253 described above. The sheath 353 can be transitioned between a first configuration, in which the sheath 353 substantially surrounds the puncture member 350, and a second configuration, in which a portion of the puncture member 350 extends in a proximal direction beyond a surface of the sheath 353, as described above with reference to the sheath 253 (see e.g., FIGS. 6 and 8). The fluid reservoir 310 can be substantially similar in form and function as the fluid reservoir 210 described above. In this manner, the fluid reservoir 310 can include a distal end portion 311 having a surface 312 that defines a port 313, as described above with reference to the fluid reservoir 210 (see e.g., FIG. 5). Thus, aspects of the collection device 300 that are substantially similar to the corresponding aspects of the collection device 200 are not described in further detail herein.

Figure 9:
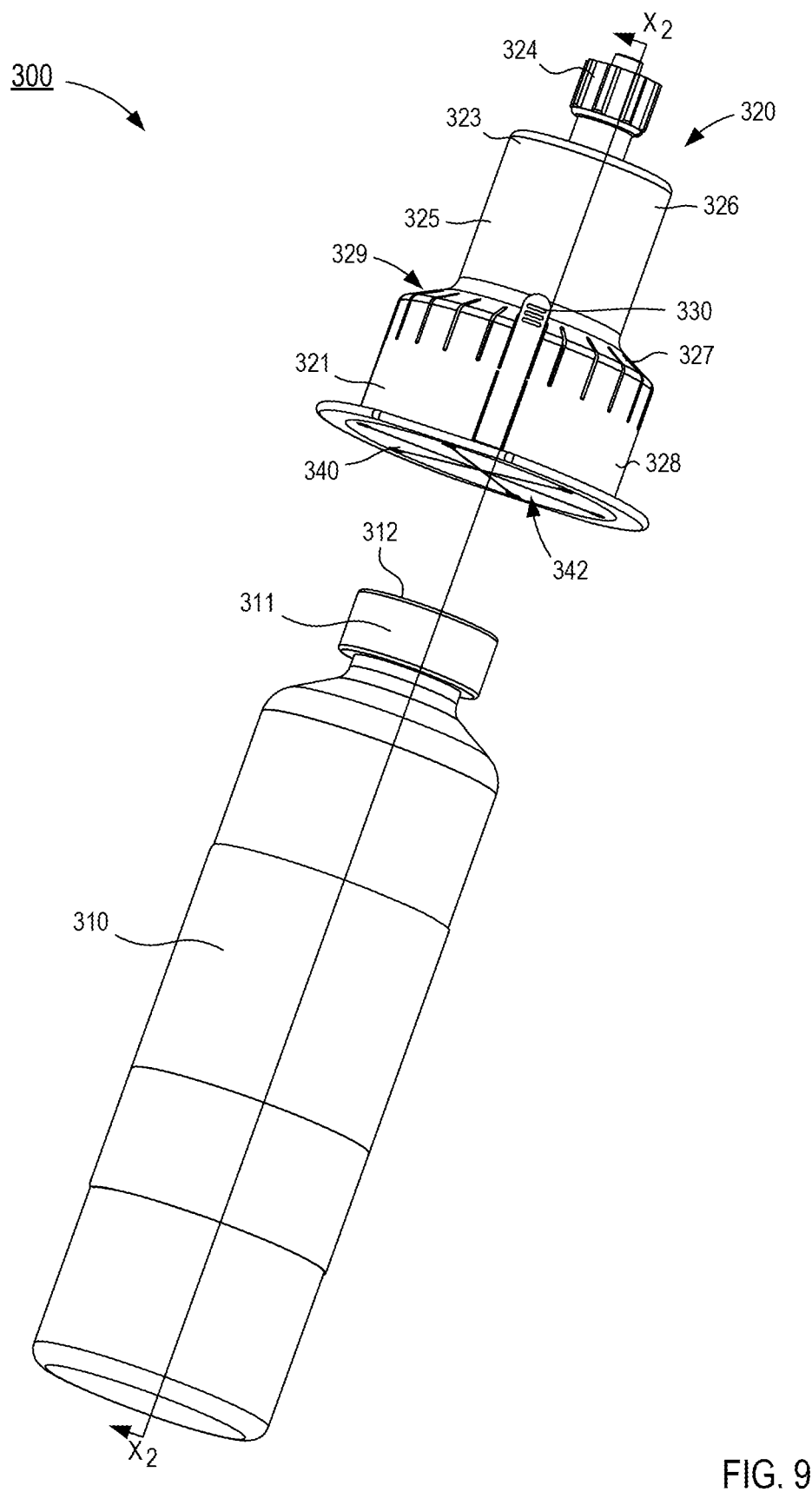
FIG. 9 is a perspective view of a bodily-fluid collection device, according to another embodiment.
Figure 10:
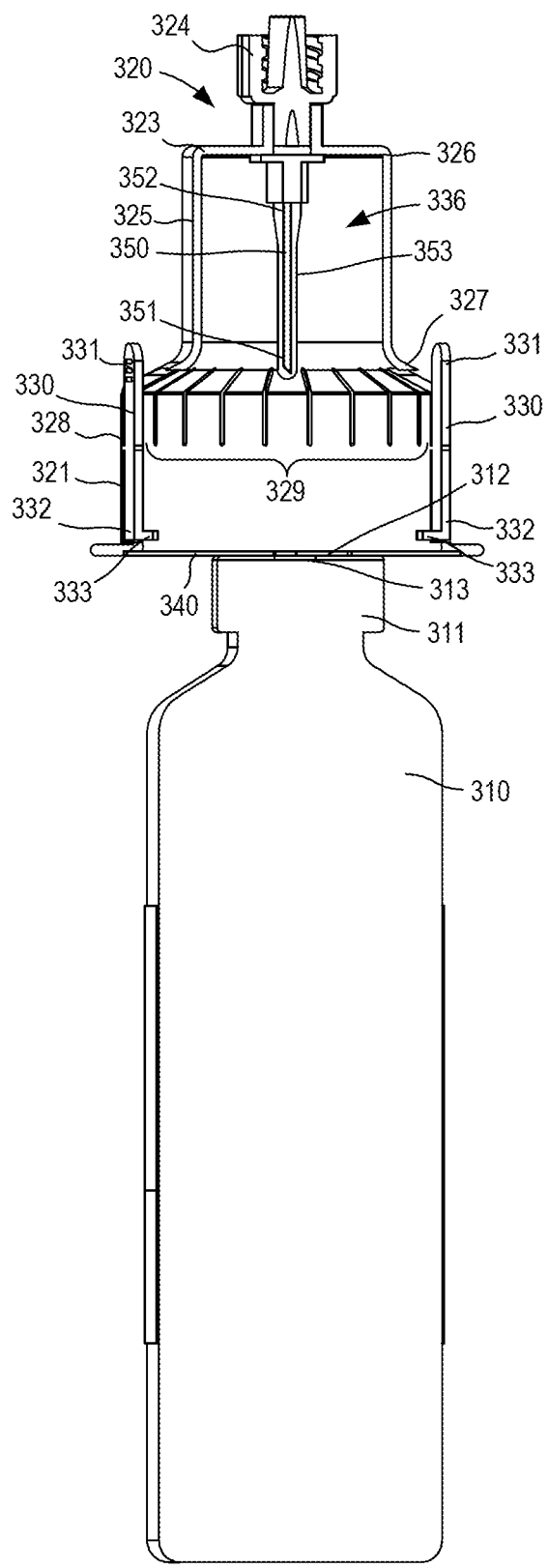
FIG. 10 is a cross-sectional view of the bodily-fluid collection device of FIG. 9 taken along the line $X_2$-$X_2$, in a first configuration.

As shown in FIGS. 9 and 10, the transfer adapter 320 has a proximal end portion 321 and a distal end portion 323, and defines an inner volume 336 therebetween. The transfer adapter 320 can be any suitable shape, size, or configuration. For example, the transfer adapter 320 can have a set of annular walls 325 that define at least a portion of the inner volume 336. The annular walls 325 of the transfer adapter 320 house at least a portion of the disinfection member 340 and the puncture member 350. In other words, the disinfection member and the puncture member 350 are each at least partially disposed within the inner volume 336 defined by the transfer adapter 320. Moreover, at least a portion of the fluid reservoir 310 can be selectively disposed within the inner volume 336, as described in further detail herein.

As described above with reference to the transfer adapter 220 of FIGS. 2-8, the annular walls 325 of the transfer adapter 320 can include a first cylindrical portion 326 (also referred to herein as "first portion"), a second cylindrical portion 328 (also referred to herein as "second portion"), and a tapered portion 327 disposed therebetween. The arrangement of the annular walls 325 can be substantially similar to the arrangement of the annular walls 225 of the transfer adapter 220 described above with reference to FIGS. 2 and 3. Accordingly, a diameter a portion of the inner volume 336 (e.g., an inner diameter) defined by the annular walls 325 can be related to a shape of at least a portion of the fluid reservoir 310, as described in further detail herein.

The annular walls 325 also include a set of release members 330 and define a set of vents 329. As shown in FIGS. 9 and 10, the set of vents 329 can extend substantially through the set of annular walls 325 to allow venting of the inner volume 336. Although shown in FIGS. 9 and 10 as being substantially elongated slots, in other embodiments, the annular walls 325 can define a set of vents having any suitable shape or configuration. For example, in some embodiments, the annular walls 325 can define a set of vents that are substantially circular. Moreover, although the set of vents 329 are substantially uniform in shape and/or in spacing, in other embodiments, the annular walls 325 can define a set of vents in any suitable arrangement. For example, in some embodiments, a first subset of vents can be a first size and a second subset of vents can be a second size, different from the first size. In some embodiments, the annular walls 325 can define a set of vents that are defined in a substantially staggered arrangement. As described in further detail herein, the vents 329 can allow a gas (e.g., air, evaporated disinfection agent, etc.) to flow out of and/or into the inner volume 336.

The release members 330 can be monolithically formed with the transfer adapter 320 and can be engaged by a user to transition the release members 330 relative to the annular walls 325 between a first configuration and a second configuration. As shown in FIG. 10, the release members 330 include a first end portion 331 and a second end portion 332. The first end portion 331 can be engaged by a user to transition the release members between the first configuration and the second configuration. For example, in some instances, a user can exert a force on the first end portion 331 of the release member 330 to move the first end portion 331 in a substantially radial direction toward the inner volume 336. The arrangement of the release members 330 can be such that as the first end portion 331 is moved in the substantially radial direction toward the inner volume 336, the second end portion 332 is moved in a substantially radial direction that away from the inner volume 336 (e.g., the second end portion 332 is moved in a direction substantially opposite to the direction of the first end portion 331), as described in further detail herein. The second end portion 332 of the release members 330 includes a tab 333 that can be placed in contact with a surface of the fluid reservoir 310 to selectively limit movement of the fluid reservoir 310 in the distal direction when the release members 330 are in the first configuration, as described in further detail herein. Moreover, when the release members 330 are in the second configuration and the fluid reservoir 310 is disposed in the inner volume 336, the tabs 333 can be placed in a position away from (e.g., not in contact with) the fluid reservoir 310, as described in further detail herein.

Although the transfer adapter 320 is shown in FIGS. 9 and 10 as including a set of two release members 330, in other embodiments, a transfer adapter can include any number of release members 330. For example, in some embodiments, a transfer adapter can include a single release member that can be manipulated in a similar manner as described above. In other embodiments, a transfer adapter can include three or more release members that can be manipulated in a similar manner as described above. Although the release members 330 are described above as being transitioned in a substantially radial direction between a first configuration and a second configuration, in other embodiments, a transfer adapter can include one of more release members that can be moved and/or transitioned between a first configuration and a second configuration in, for example, a substantially axial direction relative to a centerline axis defined by the transfer adapter 320.

Although the release members 330 are described above as being transitioned as a result of an applied force by a user, in other embodiments, one or more release members can be transitioned between a first configuration and a second configuration as a result of any suitable actuation. For example, one or more release members can be transitioned between its first configuration and its second configuration as a result of an electrical signal (e.g., an electrical actuation). In other embodiments, a user can indirectly exert a force that is operable in transitioning one or more release members between the first configuration and the second configuration. For example, in some embodiments, the user can exert a force on, for example, the fluid reservoir 310 to place a surface of the fluid reservoir 310 in contact with, for example, a tab disposed at an end portion of one or more release member. In such embodiments, the force exerted by the surface of the fluid reservoir 310 on the tab of each release member can be sufficient to transition the one or more release members from the first configuration to the second configuration.

The proximal end portion 321 of the transfer adapter 320 can be substantially open (see e.g., FIGS. 11 and 12) to movably receive at least a portion of the fluid reservoir 310. Said another way, at least a portion of the fluid reservoir 310 can be inserted through an opening defined by the proximal end portion 321 of the transfer adapter 320 to movably dispose the portion of the fluid reservoir 310 within the inner volume 336. As described in further detail herein, the fluid reservoir 310 can be inserted through the proximal end portion 321 of the transfer adapter 320 and can be placed in a first position (e.g., a proximal position) and a second position (e.g., a distal position) within the inner volume 336.

The distal end portion 323 of the transfer adapter 320 includes a port 324 that can be physically and fluidically coupled to any suitable lumen defining device such as a catheter, cannula, needle, trocar, or the like. For example, in some embodiments, the port 324 can be a Luer Lok® that can be physically and fluidically coupled to a peripheral intravenous (IV) needle and/or the like, as described with reference to the port 224 of the transfer adapter 220. In addition, the port 324 can be in fluid communication with the puncture member 350 disposed within the inner volume 336. Therefore, when the port 324 is fluidically coupled to the lumen defining device, the puncture member 350 is placed in fluid communication with the lumen defining device, as described above with reference to the port 224 and the puncture member 250, respectively.

As shown in FIGS. 9 and 10, the disinfection member 340 is at least partially disposed within the inner volume 336 of the transfer adapter 320. More particularly, in some embodiments, the disinfection member 340 can be coupled to an inner surface of the annular walls 325 and can be disposed in a position relative to the transfer adapter 320 such that a proximal surface of the disinfection member 340 is substantially coplanar with a proximal surface of the transfer adapter 320 (e.g., substantially flush or even). In some embodiments, the disinfection member 340 can define a friction fit with the inner surface of the annular walls 325 to substantially retain the disinfection member 340 in a substantially fixed position within the inner volume 336. In some embodiments, the disinfection member 340 can be coupled to the inner surface via an adhesive or the like. As described in further detail herein, when the fluid reservoir 310 is placed in its first position, a surface of the disinfection member 340 (e.g., the proximal surface) is placed in contact with a surface of the fluid reservoir 310 to substantially disinfect the surface.

Although not shown in FIGS. 9-12, the collection device 300 can include a seal or the like that can be removably coupled to, for example, a proximal surface of the transfer adapter 320. The seal can be any suitable configuration. For example, in some embodiments, the seal can be substantially similar to, the seal 238 described above with reference to FIG. 2. The arrangement of the disinfection member 340 and the proximal end portion 321 of the transfer adapter 320 can be such that when the seal is coupled to the transfer adapter 320, the seal substantially covers the proximal surface of the disinfection member 340. In some instances, the seal can fluidically isolate the proximal surface of the disinfection member 340 to maintain a relative humidity that is sufficient to substantially prevent evaporation of a disinfection agent disposed on or in the disinfection member 340, as described above.

In use, a user (e.g., a doctor, nurse, technician, physician, phlebotomist, etc.) can manipulate the collection device 300 to couple the port 324 to a lumen defining device such as, for example, a peripheral IV, as described above. The lumen defining device can be placed in communication with a bodily-fluid in a patient such that a fluid flow path is defined between a flow of the bodily-fluid within the patient and the lumen defined by the puncture member 350 (e.g., via the port 324). In some instances, with the port 324 coupled to the lumen defining device, the user can manipulate the collection device 300 remove a seal or the like from the transfer adapter 320, as described above with reference to the seal 238.

As shown in FIG. 10, the user can place the collection device 300 in a first configuration by moving the fluid reservoir 310 in a distal direction relative to the transfer adapter 320 to place the fluid reservoir 310 in contact with the disinfection member 340 (e.g., the first position of the fluid reservoir 310). In this manner, the disinfection member 340 can contact the surface 312 of the fluid reservoir 310 to substantially disinfect the surface 312. In some embodiments, the user can maintain the fluid reservoir 310 in the first position for a predetermined time period to allow the disinfection agent to disinfect the surface 312 of the fluid reservoir 310. Similarly stated, the user can place the fluid reservoir 310 in the first position and can hold the fluid reservoir 310 substantially in the first position to allow the disinfection member 340 sufficient time (as described by disinfection agent manufacturer instructions) to disinfect the surface 312 of the fluid reservoir 310. In other embodiments, the fluid reservoir 310 need not be held in the first position for the disinfection member 340 to disinfect the surface 312 of the fluid reservoir 310. For example, in some embodiments, the user can move the fluid reservoir 310 in the distal direction and in a substantially continuous manner to place the fluid reservoir 310 in the first position and then the second position.

Figure 11:
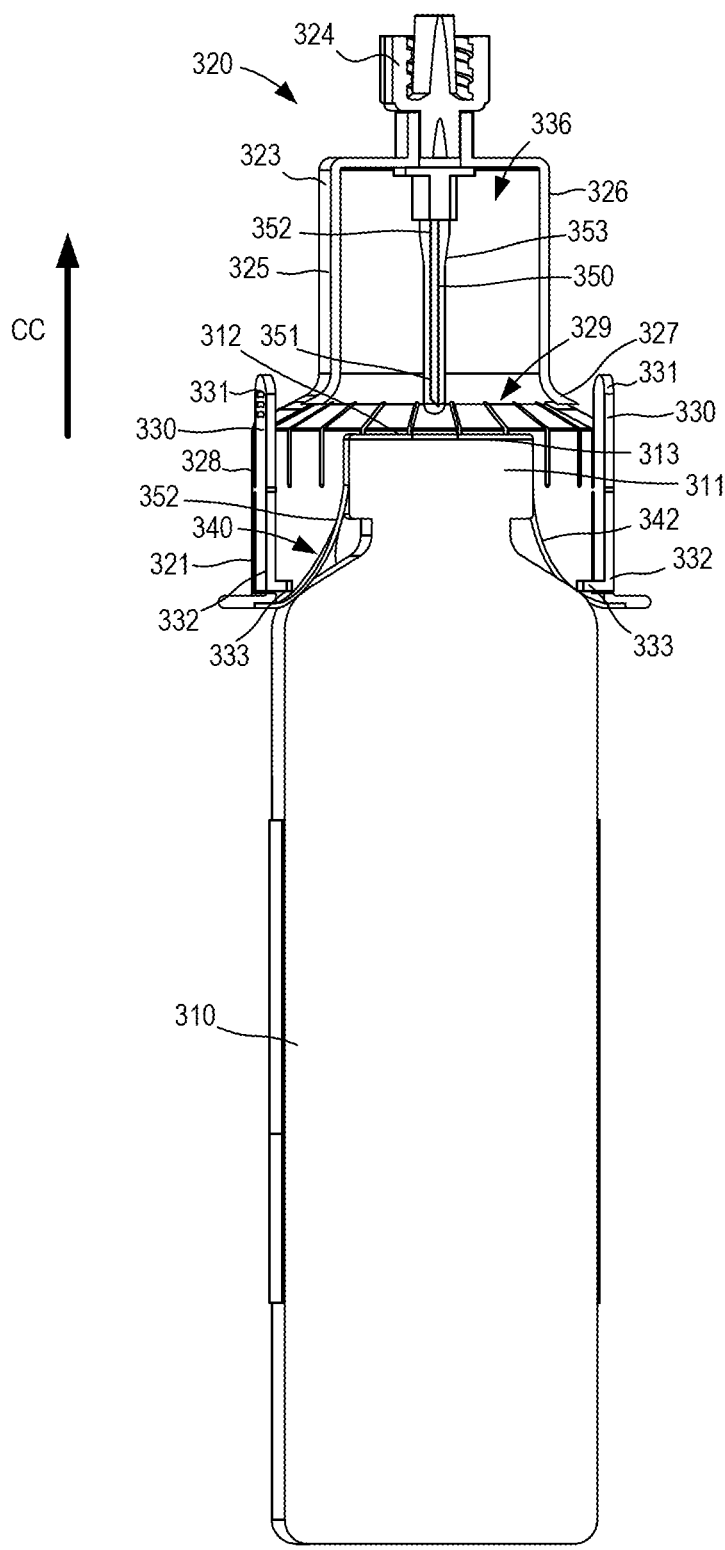
FIG. 11 is a cross-sectional side view of the bodily-fluid collection device of FIG. 9 taken along the line $X_2$-$X_2$, in a second configuration.

The disinfection member 340 can be transitioned (e.g., opened or otherwise reconfigured) between the first configuration and the second configuration as the fluid reservoir 310 is moved from the first position toward the second position, as described above with reference to the disinfection member 240. Moreover, as shown in FIG. 11, as the fluid reservoir 310 is advanced in the distal direction beyond the disinfection member 340, the fingers 342 of the disinfection member 340 can deform, bend, and/or otherwise reconfigure to allow the fluid reservoir 310 to pass in a distal direction beyond the disinfection member 340. The fluid reservoir 310 can be advanced in a distal direction relative to the disinfection member 340 to place the collection device 300 in a second configuration, as indicated by the arrow CC in FIG. 11. For example, the user can exert a force of the fluid reservoir 310 that moves the fluid reservoir 310 in the distal direction to place a surface of the fluid reservoir 310 in contact with the tab 333 of the release members 330. Therefore, with the release members 330 in the first configuration, the tabs 333 can substantially limit further distal movement of the fluid reservoir 310, as described above.

In some embodiments, the collection device 300 can be retained in the second configuration for a predetermined time to, for example, allow a disinfection agent to evaporate from the surface 312 of the fluid reservoir 310. For example, in some embodiments, the distal end portion 311 of the fluid reservoir 310 can be positioned within the inner volume 336 to place the surface 312 of the fluid reservoir 310 in fluid communication with a volume outside of the transfer adapter 320 via the set of vents 329. In this manner, the disinfection agent that was transferred to the surface 312 of the fluid reservoir 310 from the disinfection member 340 can be allowed to evaporate. For example, in some instances, the vents 329 can allow an air flow into the inner volume 336 of the transfer adapter 320 that is operable in evaporating the disinfection agent disposed on the surface. Thus, the disinfection agent can substantially disinfect the surface 312 of the fluid reservoir 310 and then can evaporate from the surface 312 prior to the fluid reservoir 310 being placed in the second position.

Figure 12:
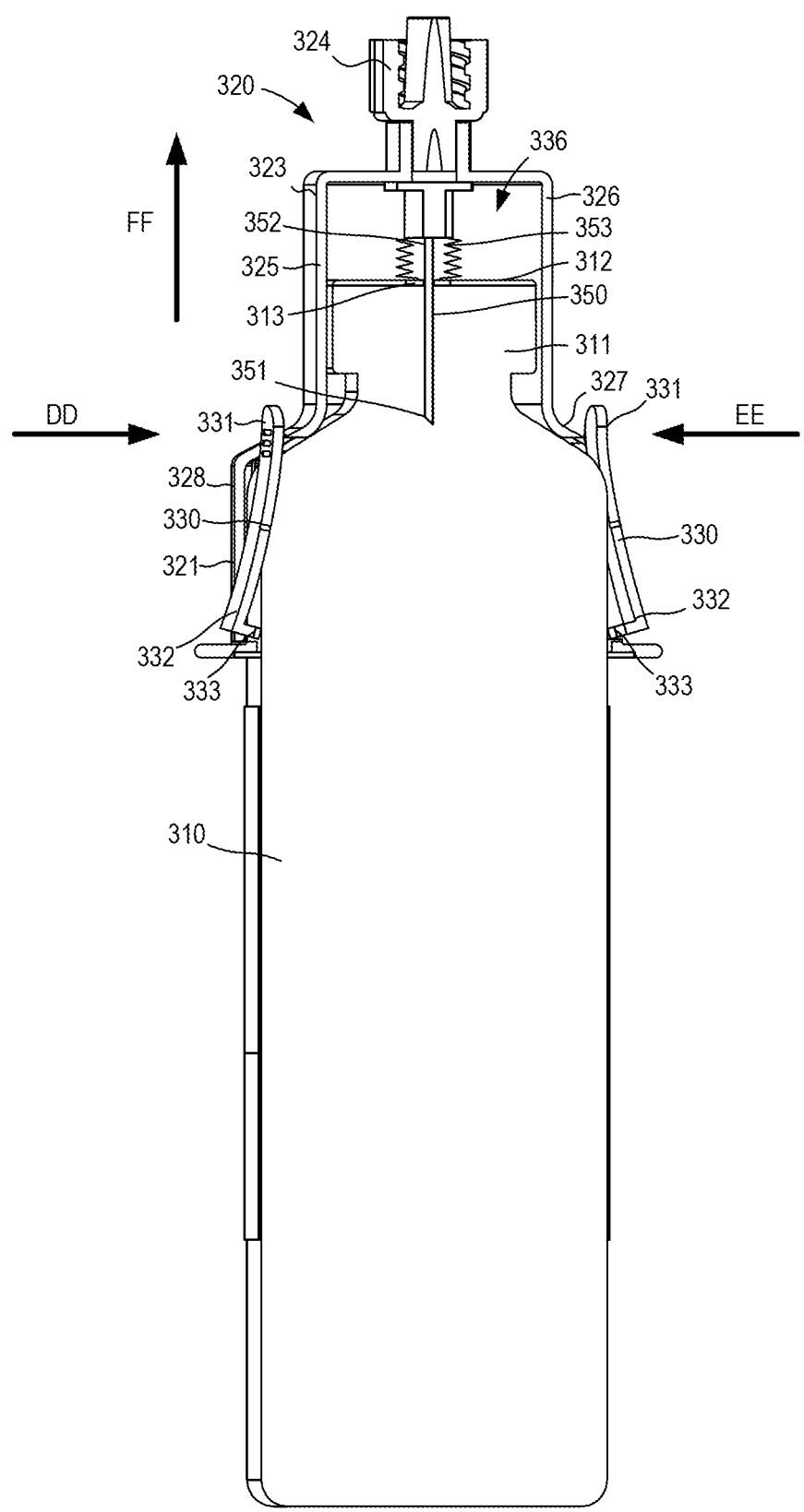
FIG. 12 is a cross-sectional view of the bodily-fluid collection device of FIG. 9 taken along the line $X_2$-$X_2$, in a third configuration.
Figure 13:
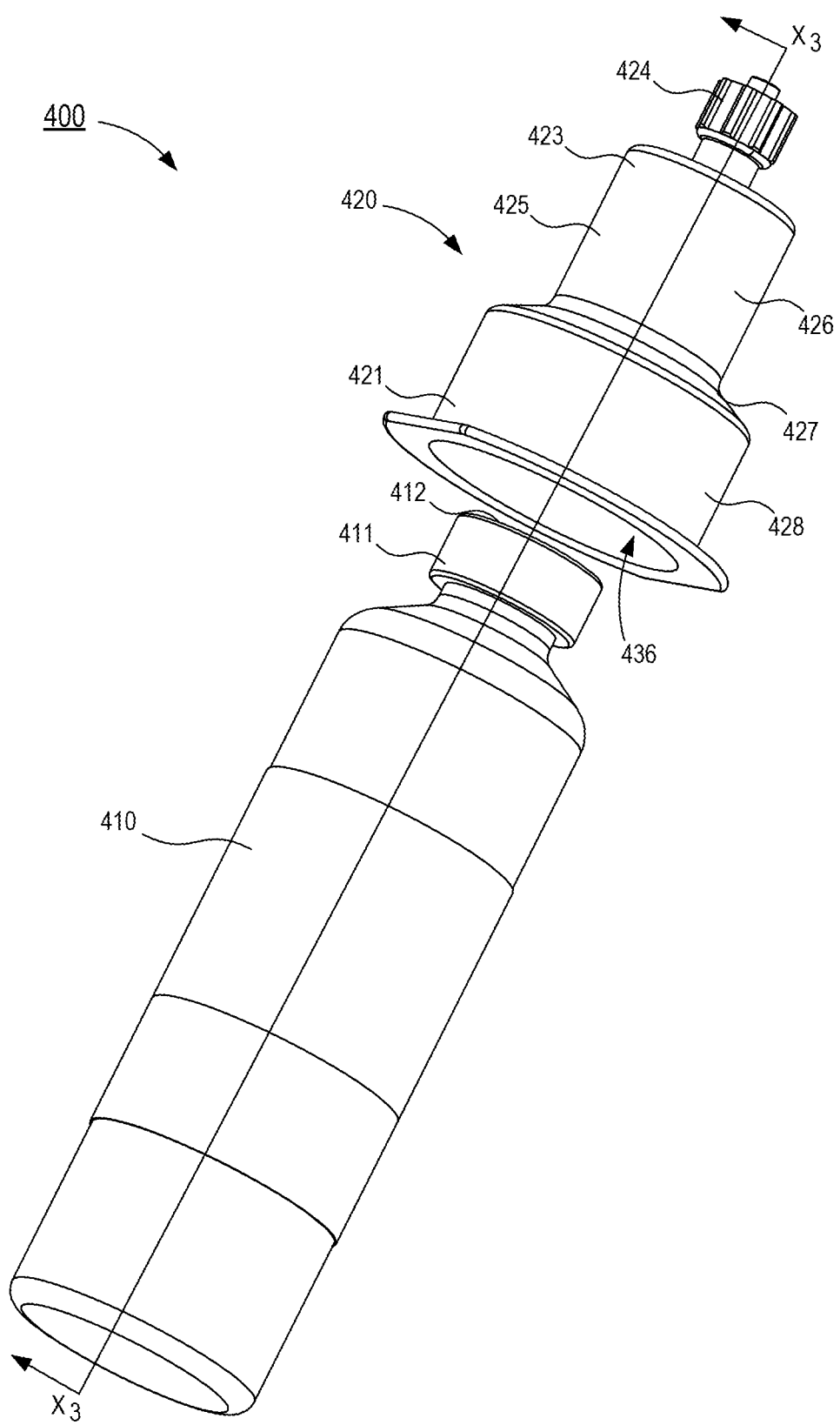
FIG. 13 is a perspective view of a bodily-fluid collection device, according to another embodiment.

With the disinfection agent substantially evaporated from the surface 312 of the fluid reservoir 310, the user can exert a force on the first end portion 331 of the release members 330 to transition the release members 330 from the first configuration to the second configuration, as indicated by the arrows DD and EE in FIG. 12. In this manner, second end portion 332 of each release member 330 can move in a substantially opposite direction of the corresponding first end portion 331. Said another way, if the first end portion 331 of one of the release members 330 is moved in the DD direction, the second end portion 332 of that release member 330 is moved substantially in the EE direction. Conversely, in the first end portion of one of the release members 330 is moved in the EE direction, the second end portion of that release member 330 is moved substantially in the DD direction, as shown in FIG. 12.

With the release members 330 in the second configuration, the user can move the fluid reservoir 310 to the second position to place the puncture member 350 into contact with the surface 312, thereby placing the collection device 300 in a third configuration, as indicated by the arrow FF in FIG. 12. For example, as the fluid reservoir 310 is moved in the distal direction toward the second position, the proximal end portion 351 of the puncture member 350 is placed in contact with the port 313 (e.g., pierces the port 313) included in and/or defined by the surface 312, as described in detail above with reference to FIG. 8. Moreover, the distal movement of the fluid reservoir 310 toward the second position can transition the sheath 353 substantially surrounding the puncture member 350 from its first configuration to its second configuration, as described above. Thus, the distal end portion 351 of the puncture member 350 can extend beyond the sheath 353 to pierce the port 313 of the fluid reservoir 310 such that a portion of the puncture member 350 is disposed in an inner volume defined by the fluid reservoir 310, as shown in FIG. 12.

With the puncture member 350 defining a lumen and with the fluid reservoir 310 in the second position, the portion of the puncture member 350 can be disposed within the fluid reservoir 310 such that the lumen defined by the puncture member 350 is in fluid communication with the inner volume of the fluid reservoir 310. Thus, with the fluid flow path defined between the flow of bodily-fluid in the patient and the lumen defined by the puncture member 350 (e.g., via the lumen defining device and the port 324, as described above), the puncture member 350 can place the fluid reservoir 310 in fluid communication with the flow of bodily-fluid in the patient. As described above, the fluid reservoir 310 can define a negative pressure that can exert a suction force in or on the lumen of the puncture member 350 when the puncture member 350 pierces the fluid reservoir 310 and, in turn, the negative pressure can exert a suction force within, for example, a vein of the patient to urge the bodily-fluid to flow within the fluid flow path to be disposed in the inner volume of the fluid reservoir 310. In some instances, the bodily-fluid can flow within the fluid flow path until a desired volume of bodily-fluid is disposed in the fluid reservoir 310, as described above. With the desired amount of bodily-fluid disposed in the fluid reservoir 310, the fluid reservoir 310 can be moved in the proximal direction to, for example, remove the fluid reservoir 310 from the inner volume 336 of the transfer adapter 320. In some instances, a second fluid reservoir (not shown) can be inserted into the transfer adapter 320 and placed in fluid communication with the flow of bodily-fluid in the patient in substantially the same manner as described above. Thus, any suitable number of fluid reservoirs can be inserted into the transfer adapter 320 such that a piercable surface of each fluid reservoir is disinfected prior to receiving a flow of bodily-fluid. As such, the amount of contaminants and/or microbes transferred to a bodily-fluid sample from, for example, a piercable surface of a fluid reservoir can be reduced and/or substantially eliminated. Moreover, by allowing the disinfection agent on the surface 312 of the fluid reservoir 310 to substantially evaporate prior to the puncture member 350 piercing the surface 310, the likelihood of the disinfection agent being transferred to the flow of the bodily-fluid and/or to the inner volume of the fluid reservoir 310 can be reduced and/or substantially eliminated.

Although the collection device 200 (FIGS. 2-8) and the collection device 300 (FIGS. 9-12) are shown above as including the disinfection members 240 and 340, respectively, that are each arranged as a diaphragm that can be transitioned from the first (e.g., closed) configuration to the second (e.g., open) configuration, in other embodiments, a collection device can include any suitable disinfection member. For example, FIGS. 13-17 illustrate a bodily-fluid collection device 400 (also referred to herein as "collection device") according to another embodiment. The collection device 400 includes a transfer adapter 420, a disinfection member 440 (see e.g., FIGS. 14 and 15), a puncture member 450 (see e.g., FIGS. 16 and 17), and a fluid reservoir 410. Some aspects of the collection device 400 can be similar in form and function as corresponding aspects of the collection device 200, described above with reference to FIGS. 2-8. For example, the transfer adapter 420 can be substantially similar in form and function as the transfer adapter 220 described above. Thus, aspects of the transfer adapter 420 are described below to identify parts and/or portions, however, similar aspects are not described in further detail herein.

The transfer adapter 420 can have a proximal end portion 421 and a distal end portion 423, and can define an inner volume 436, as described above. The transfer adapter 420 can include a set of annular walls 425 having a first portion 426, a second portion 428, and a tapered portion 427, as described with above with reference to the annular walls 225 of the transfer adapter 220. The distal end portion 423 can include a port 424 that can be substantially similar to the port 224 included in the transfer adapter 220. The proximal end portion 421 can be substantially open and configured to movably receive the fluid reservoir 410, as described above. Moreover, at least a portion of the disinfection member 440 and at least a portion of the puncture member 450 can be disposed within the inner volume 436.

The puncture member 450 can be substantially similar in form and function as the puncture member 250, described above with reference to FIGS. 3-8. Thus, aspects of the puncture member 450 are described below to identify parts and/or portions, however, similar aspects are not described in further detail herein. The puncture member 450 can include a proximal end portion 451 and a distal end portion 452. The distal end portion 452 can be coupled to the port 424 of the transfer adapter 420 (e.g., physically and fluidically coupled), and the proximal end portion 451 can be selectively placed in contact with a surface of the fluid reservoir 410, as described above with reference to the puncture member 250. Moreover, the puncture member 450 can be at least temporarily disposed within a sheath 453 that can be substantially similar to the sheath 253 described above. The sheath 453 can be transitioned between a first configuration, in which the sheath 453 substantially surrounds the puncture member 450, and a second configuration, in which a portion of the puncture member 450 extends in a proximal direction beyond a surface of the sheath 453, as described above with reference to the sheath 253 (see e.g., FIGS. 6 and 8).

The fluid reservoir 410 can be substantially similar in form and function as the fluid reservoir 210, described above with reference to FIG. 5. Thus, aspects of the fluid reservoir 410 are described below to identify parts and/or portions, however, similar aspects are not described in further detail herein. The fluid reservoir 410 can include a distal end portion 411 having a surface 412 that defines a port 413, as described above with reference to the fluid reservoir 210 (see e.g., FIG. 5). As described in further detail herein, the fluid reservoir 410 can be inserted into the inner volume 436 of the transfer adapter 420 and can be moved to a first position and a second position relative to the transfer adapter 420.

Figure 14:
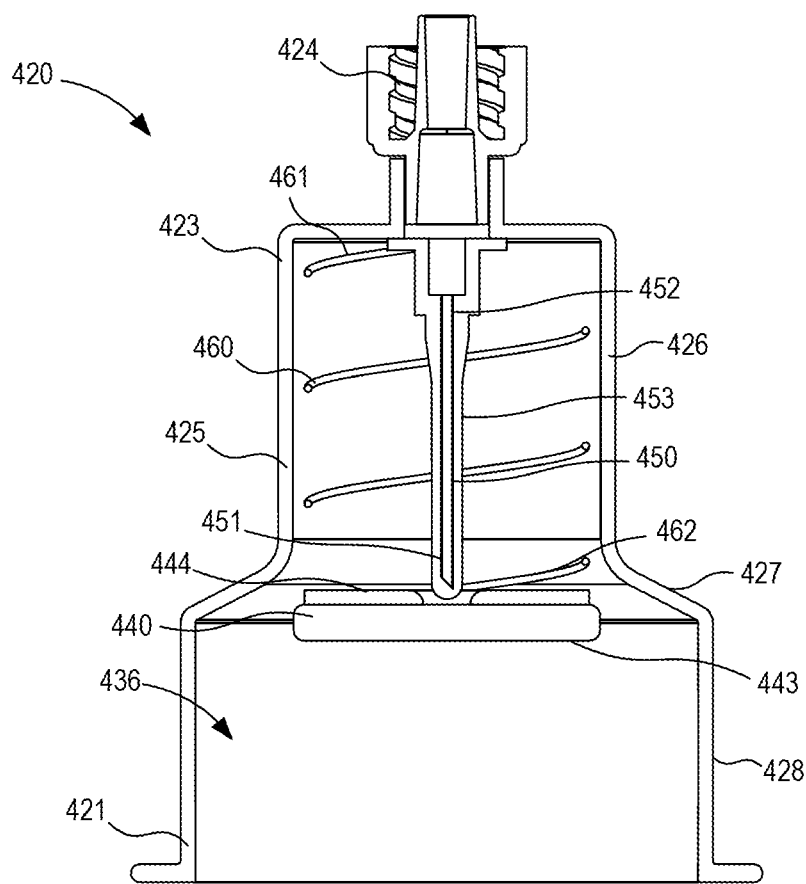
FIG. 14 is a cross-sectional view of a transfer adapter included in the bodily-fluid collection device of FIG. 13 taken along the line $X_3$-$X_3$.
Figure 15:
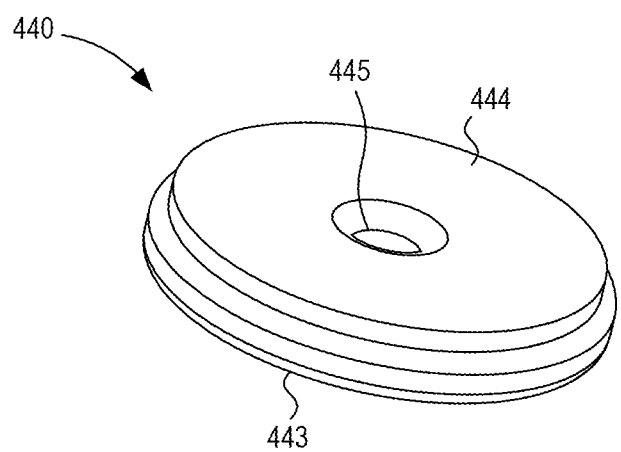
FIG. 15 is a perspective view of a disinfection member included in the transfer adapter of FIG. 14.

As shown in FIGS. 14 and 15, the disinfection member 440 is movably disposed within the inner volume 436 of the transfer adapter 420 between a first position (e.g., a proximal position (FIG. 16)) and a second position (e.g., a distal position (FIG. 17)). The disinfection member 440 can be, for example, a pad, a swab, a sponge, and/or the like that can include a disinfecting agent. The disinfection member 440 includes a first surface 443 and a second surface 444, opposite the first surface 443. In some embodiments, at least the first surface 443 of the disinfection member 440 can be impregnated with a disinfecting agent such as, those described above. In some embodiments, the disinfection member 440 can include and/or can define a portion that is substantially porous, for example, to act as a substrate for the disinfection agent. As described in further detail herein, when the fluid reservoir 410 is placed in its first position within the inner volume 436, the disinfection member 440 is placed in contact with the surface 412 of the fluid reservoir 410 to substantially disinfect the surface 412.

The second surface 444 of the disinfection member 440 includes a port 445 or the like that can selectively receive a portion of the puncture member 450. For example, in some embodiments, the port 445 can be a self-closing and/or self-healing port that can be transitioned between a first (e.g., closed) configuration and a second (e.g., open) configuration. By way of example, in some instances, the puncture member 450 can pierce the port 445 to place the port 445 in its second configuration and, upon removing the puncture member 450 the port 445 can automatically transition to its first configuration (e.g., the closed configuration).

As shown in FIG. 14, a bias member 460 can be disposed in the inner volume 436 of the transfer adapter 420. More particularly, the bias member 460 has a first end portion 461 that can be coupled to an inner surface (e.g., a distal surface) of the transfer adapter 420, and a second end portion 462 that can be in contact with and/or coupled to the second surface 444 of the disinfection member 440. Similarly stated, the bias member 460 can be suspended from the inner surface of the transfer adapter 420 and can be coupled to the disinfection member 440 to suspend the disinfection member 440 in the inner volume 436. The bias member 460 can be, for example, a spring or the like that can be transitioned between a first (e.g., extended) configuration and a second (e.g., compressed) configuration, as described in further detail herein.

Although not shown in FIGS. 13-17, the collection device 400 can include a seal or the like that can be removably coupled to, for example, a proximal surface of the transfer adapter 420. The seal can be any suitable configuration. For example, in some embodiments, the seal can be substantially similar to the seal 238 described above with reference to FIG. 2. In this manner, the seal can fluidically isolate the inner volume 436 to substantially maintain the sterility of the inner volume 436 and/or the puncture member 450 and disinfection member 440 disposed therein. Moreover, by fluidically isolating the inner volume 436, the seal can maintain a relative humidity within the inner volume 436 that is sufficient to substantially prevent evaporation of a disinfection agent disposed therein, as described above.

In use, a user (e.g., a doctor, nurse, technician, physician, phlebotomist, etc.) can manipulate the collection device 400 to couple the port 424 to a lumen defining device such as, for example, a peripheral IV, as described above. The lumen defining device can be placed in communication with a bodily-fluid in a patient such that a fluid flow path is defined between a flow of the bodily-fluid within the patient and the lumen defined by the puncture member 450 (e.g., via the port 424). In some instances, with the port 424 coupled to the lumen defining device, the user can manipulate the collection device 400 remove a seal or the like from the transfer adapter 420, as described above with reference to the seal 238.

Figure 16:
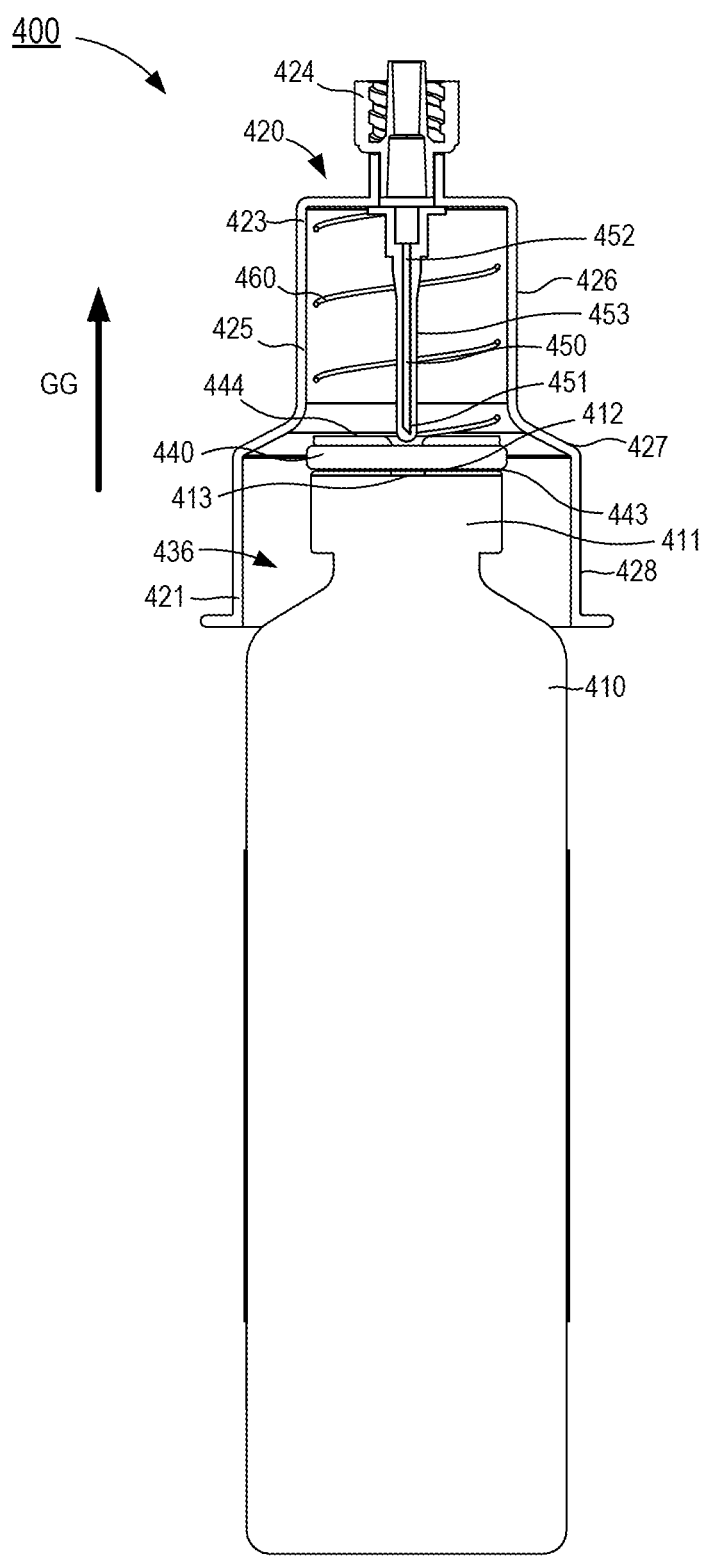
FIG. 16 is a cross-sectional side view of the bodily-fluid collection device of FIG. 13 taken along the line $X_3$-$X_3$, in a first configuration.

The user can move the fluid reservoir 410 in a distal direction relative to the transfer adapter 420 to place the fluid reservoir 410 in the first position within the inner volume 436, thereby placing the collection device 400 in a first configuration, as indicated by the arrow GG in FIG. 16. In this manner, the first surface 443 of the disinfection member 440 can contact the surface 412 of the fluid reservoir 410 to substantially disinfect the surface 412. In some embodiments, the disinfection member 440 can be configured to, for example, compress when placed in contact with the surface 412 of the fluid reservoir 410. In such embodiments, by compressing the disinfection member 440, a disinfecting agent suspended in, for example, a porous substrate of the disinfection member 440 can be expelled (e.g., squeezed) from the disinfection member 440 and deposited, at least in part, on the surface 412 of the fluid reservoir 410.

In some embodiments, the user can maintain the fluid reservoir 410 in the first position for a predetermined time period to allow the disinfection agent to disinfect the surface 412 of the fluid reservoir 410. Similarly stated, the user can place the fluid reservoir 410 in the first position and can hold the fluid reservoir 410 substantially in the first position to allow the disinfection member 440 to disinfect the surface 412 of the fluid reservoir 410. In other embodiments, the fluid reservoir 410 need not be held in the first position for the disinfection member 440 to disinfect the surface 412 of the fluid reservoir 410. For example, in some embodiments, the user can move the fluid reservoir 410 in the distal direction and in a substantially continuous manner to place the fluid reservoir 410 in the first position and then the second position.

Figure 17:
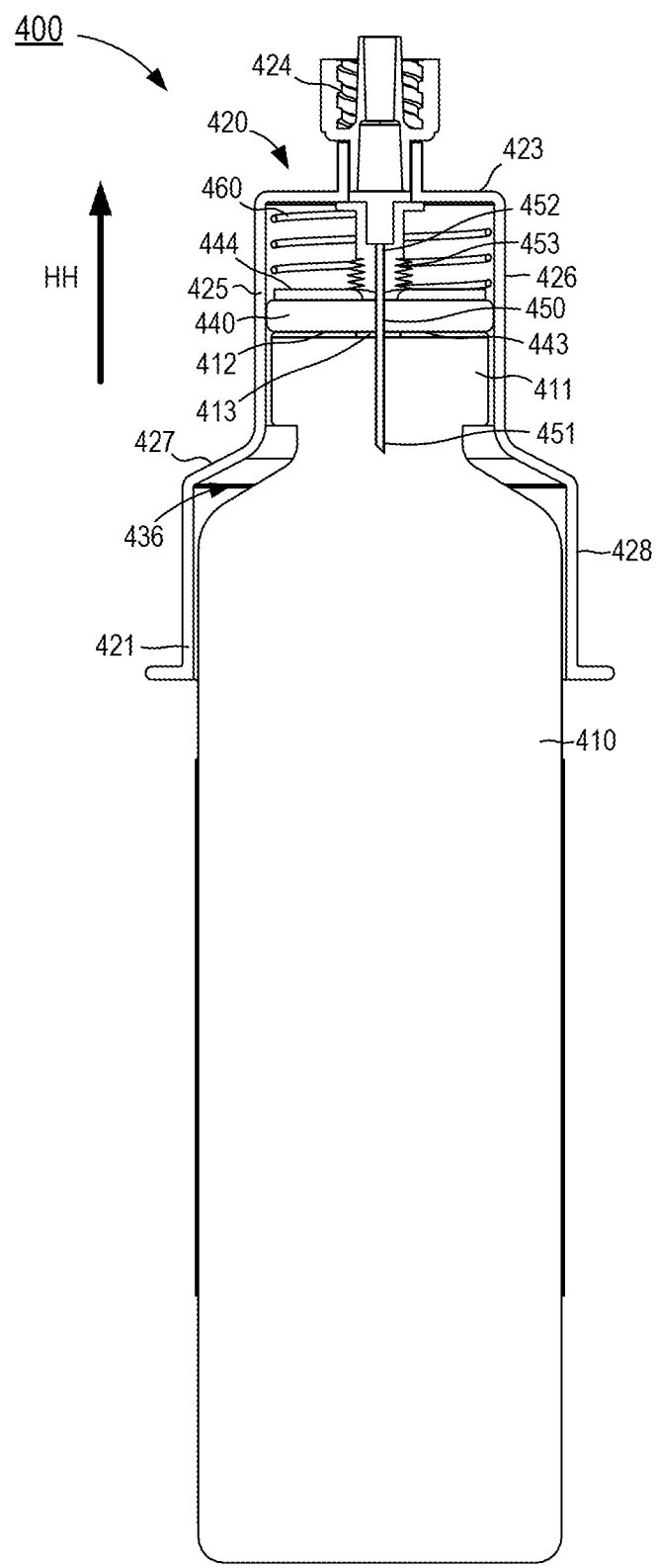
FIG. 17 is a cross-sectional view of the bodily-fluid collection device of FIG. 13 taken along the line $X_3$-$X_3$, in a second configuration.

With the disinfection member 440 in contact with the surface 412 of the fluid reservoir 410, the user can move the fluid reservoir 410 in the distal direction to place the collection device 400 in a second configuration, as indicated by the arrow HH in FIG. 17. Expanding further, the disinfection member 440 can be maintained in contact with the surface 412 of the fluid reservoir 410 as the fluid reservoir 410 is moved towards the second position. In other words, the distal movement of the fluid reservoir 410 moves the disinfection member 440 in the distal direction. In this manner, a force exerted by the user to move the fluid reservoir 410 in the distal direction is sufficient to transition the bias member 460 from its first configuration to its second configuration, as shown in FIG. 17. For example, the force exerted by the user can be sufficient to overcome a reaction force exerted by the bias member 460 that would otherwise maintain the bias member 460 in the first configuration. Thus, the fluid reservoir 410 can be placed in the second position.

As shown in FIG. 17, with the fluid reservoir 410 in the second position, the proximal end portion 451 of the puncture member 450 is placed in contact with the port 413 (e.g., pierces the port 413) included in and/or defined by the surface 412, as described in detail above with reference to FIG. 8. Moreover, the distal movement of the fluid reservoir 410 toward the second position can transition the sheath 453 substantially surrounding the puncture member 450 from its first configuration to its second configuration, as described above. Thus, the proximal end portion 451 of the puncture member 450 can extend beyond the sheath 453 to pierce the port 413 of the fluid reservoir 410 such that a portion of the puncture member 450 is disposed in an inner volume defined by the fluid reservoir 410, as shown in FIG. 17.

With the puncture member 450 defining a lumen and with the fluid reservoir 410 in the second position, the portion of the puncture member 450 can be disposed within the fluid reservoir 410 such that the lumen defined by the puncture member 450 is in fluid communication with the inner volume of the fluid reservoir 410. Thus, with the fluid flow path defined between the flow of bodily-fluid in the patient and the lumen defined by the puncture member 450 (e.g., via the lumen defining device and the port 424, as described above), the puncture member 450 can place the fluid reservoir 410 in fluid communication with the flow of bodily-fluid in the patient. As described above, the fluid reservoir 410 can define a negative pressure that can exert a suction force in or on the lumen of the puncture member 450 when the puncture member 450 pierces the fluid reservoir 410 and, in turn, the negative pressure can exert a suction force within, for example, a vein of the patient to urge the bodily-fluid to flow within the fluid flow path to be disposed in the inner volume of the fluid reservoir 410. In some instances, the bodily-fluid can flow within the fluid flow path until a desired volume of bodily-fluid is disposed in the fluid reservoir 410, as described above. With the desired amount of bodily-fluid disposed in the fluid reservoir 410, the fluid reservoir 410 can be moved in the proximal direction to, for example, remove the fluid reservoir 410 from the inner volume 436 of the transfer adapter 420. In some instances, a second fluid reservoir (not shown) can be inserted into the transfer adapter 420 and placed in fluid communication with the flow of bodily-fluid in the patient in substantially the same manner as described above. Thus, any suitable number of fluid reservoirs can be inserted into the transfer adapter 420 such that a piercable surface of each fluid reservoir is disinfected prior to receiving a flow of bodily-fluid. As such, the amount of contaminants and/or microbes transferred to a bodily-fluid sample from, for example, a piercable surface of a fluid reservoir can be reduced and/or substantially eliminated. Moreover, by allowing the disinfection agent on the surface 412 of the fluid reservoir 410 to substantially evaporate prior to the puncture member 450 piercing the surface 410, the likelihood of the disinfection agent being transferred to the flow of the bodily-fluid and/or to the inner volume of the fluid reservoir 410 can be reduced and/or substantially eliminated.

Although the collection devices 200 (FIGS. 2-8), 300 (FIGS. 9-12), and 400 (FIGS. 13-17) are shown above as including the fluid reservoirs 210, 310, and 410, that are moved in a substantially linear direction (e.g., axial direction) between the first position and the second position, in other embodiments, a collection device can include a fluid reservoir that is moved in a substantially nonlinear direction between a first position and a second position relative to a transfer adapter. For example, FIGS. 18-23 illustrate a bodily-fluid collection device 500 (also referred to herein as "collection device") according to another embodiment. The collection device 500 includes a transfer adapter 520, a disinfection member 540 (see e.g., FIGS. 19 and 21), a puncture member 550 (see e.g., FIGS. 19, 22, and 23), and a fluid reservoir 510.

Some aspects of the collection device 500 can be similar in form and function as corresponding aspects of the collection device 200, described above with reference to FIGS. 2-8. For example, the puncture member 550 can be substantially similar in form and function as the puncture member 250, described above with reference to FIGS. 3-8. Thus, aspects of the puncture member 550 are described below to identify parts and/or portions, however, similar aspects are not described in further detail herein. The puncture member 550 can include a proximal end portion 551 and a distal end portion 552 (see e.g., FIG. 19). The distal end portion 552 can be coupled to a portion of the transfer adapter 520, as described in further detail herein. The proximal end portion 551 can be selectively placed in contact with a surface of the fluid reservoir 510, as described above with reference to the puncture member 250. Moreover, the puncture member 550 can be at least temporarily disposed within a sheath 553 (FIG. 19) that can be substantially similar to the sheath 253 described above. The sheath 553 can be transitioned between a first configuration, in which the sheath 553 substantially surrounds the puncture member 550, and a second configuration, in which a portion of the puncture member 550 extends in a proximal direction beyond a surface of the sheath 553, as described above with reference to the sheath 253 (see e.g., FIGS. 6 and 8).

The fluid reservoir 510 can be substantially similar in form and function as the fluid reservoir 210, described above with reference to FIG. 5. Thus, aspects of the fluid reservoir 510 are described below to identify parts and/or portions, however, similar aspects are not described in further detail herein. The fluid reservoir 510 can include a distal end portion 511 having a surface 512 that defines a port 513, as described above with reference to the fluid reservoir 210 (see e.g., FIG. 5). As described in further detail herein, the fluid reservoir 510 can be inserted into the inner volume 536 of the transfer adapter 520 and can be moved to a first position and a second position relative to the transfer adapter 520.

Figure 18:
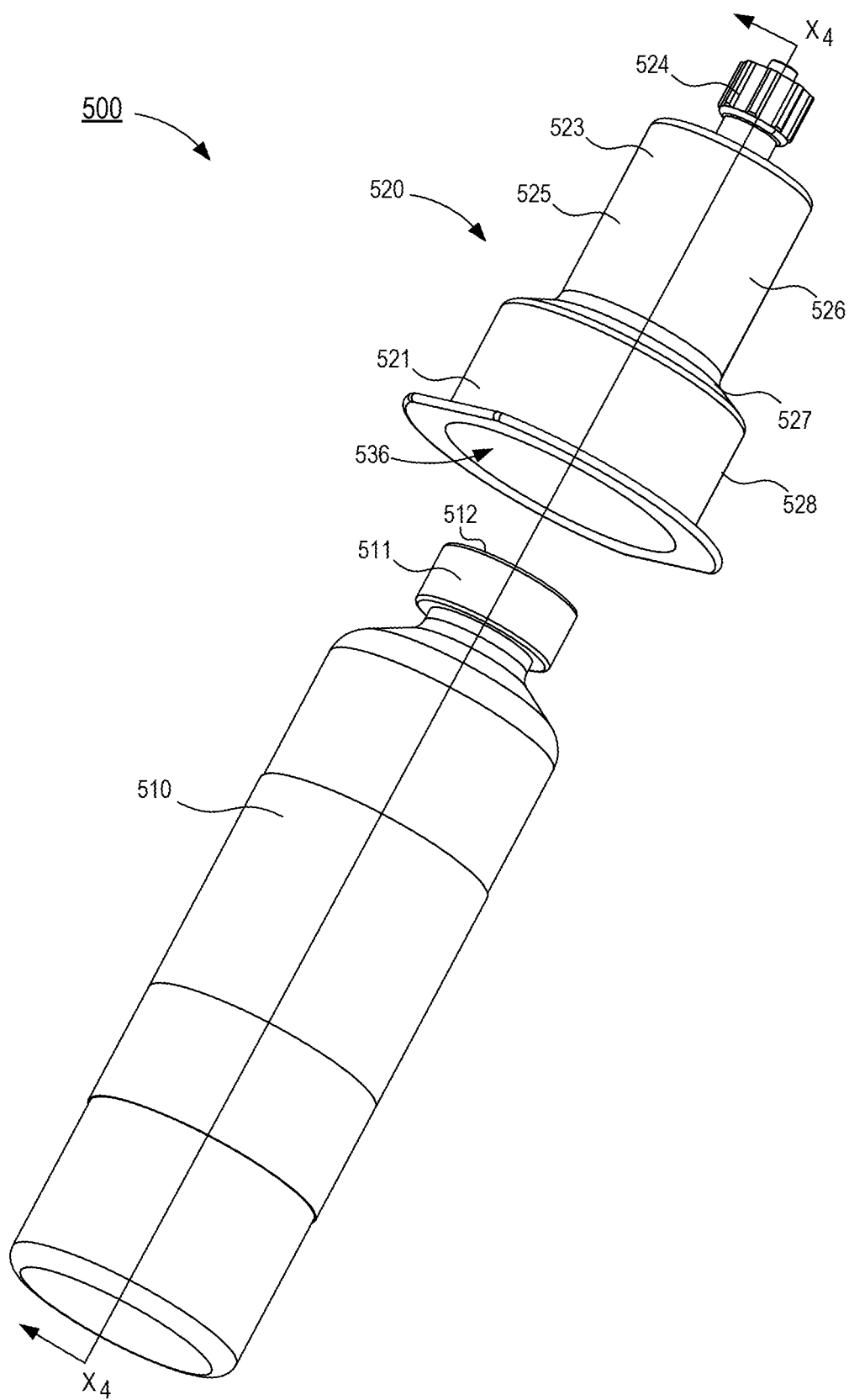
FIG. 18 is a perspective view of a bodily-fluid collection device, according to another embodiment.
Figure 19:
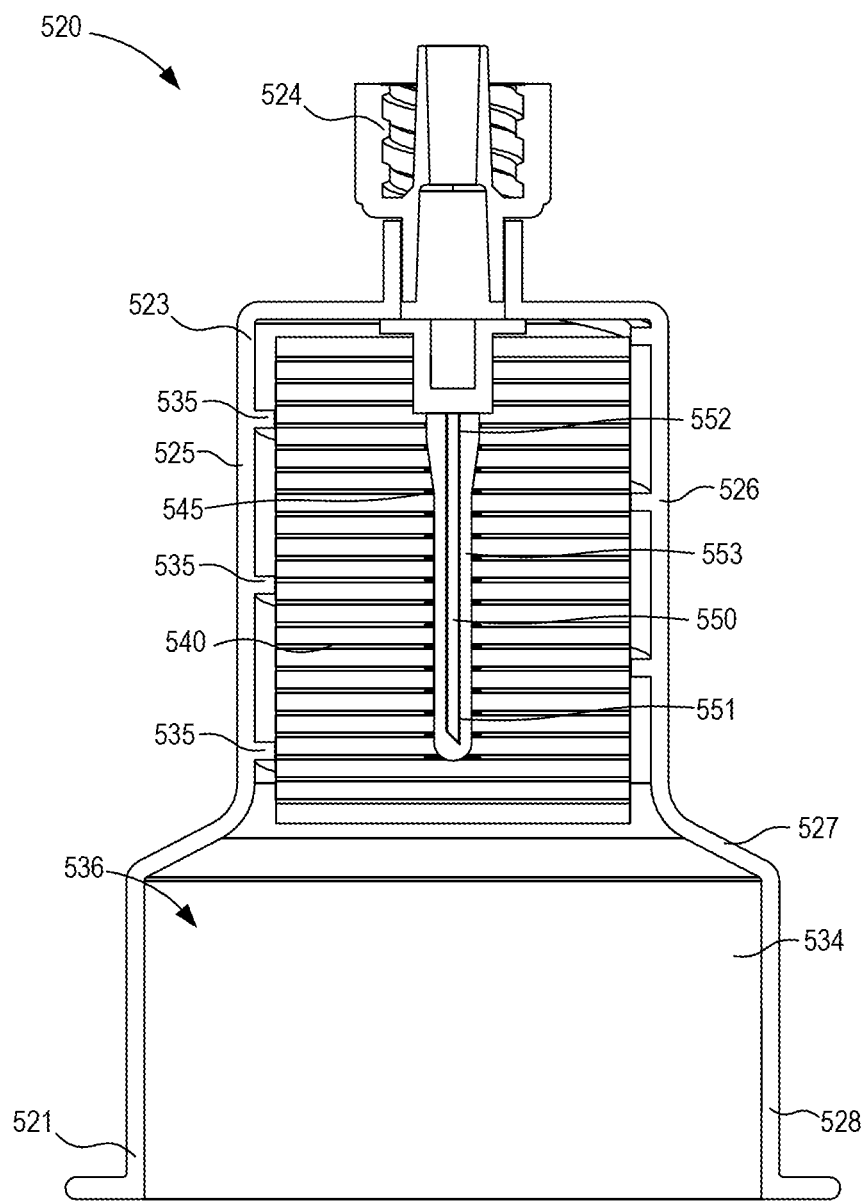
FIG. 19 is a cross-sectional view of a transfer adapter included in the bodily-fluid collection device of FIG. 18 taken along the line $X_4$-$X_4$.
Figure 20:
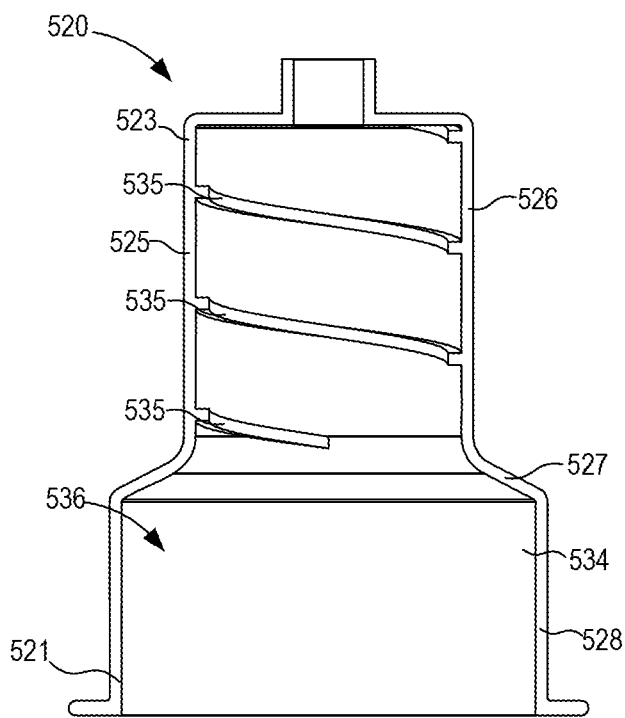
FIG. 20 is a cross-sectional view of a portion of the transfer adapter of FIG. 19 taken along the line $X_4$-$X_4$ in FIG. 18.

As shown in FIGS. 18-20, the transfer adapter 520 has a proximal end portion 521 and a distal end portion 523, and defines an inner volume 536 therebetween. The proximal end portion 521 of the transfer adapter 520 can be substantially open (see e.g., FIGS. 18 and 19) to movably receive at least a portion of the fluid reservoir 510. Said another way, at least a portion of the fluid reservoir 510 can be inserted through an opening defined by the proximal end portion 521 of the transfer adapter 520 to movably dispose the portion of the fluid reservoir 510 within the inner volume 536. The distal end portion 523 of the transfer adapter 520 includes a port 524 that can be physically and fluidically coupled to any suitable lumen defining device such as a catheter, cannula, needle, trocar, or the like. For example, in some embodiments, the port 524 can be a Luer Lok® that can be physically and fluidically coupled to a peripheral intravenous (IV) needle and/or the like, as described with reference to the port 224 of the transfer adapter 220. In addition, the port 524 can be in fluid communication with the puncture member 550 disposed within the inner volume 536, as described above with reference to the port 224 and the puncture member 250, respectively. Therefore, when the port 524 is fluidically coupled to the lumen defining device, the puncture member 550 is placed in fluid communication with the lumen defining device, as described above with reference to the port 224 and the puncture member 250, respectively.

The transfer adapter 520 can be any suitable shape, size, or configuration. For example, the transfer adapter 520 can have a set of annular walls 525 that define at least a portion of the inner volume 536. The annular walls 525 of the transfer adapter 520 house at least a portion of the disinfection member 540 and the puncture member 550. In other words, the disinfection member and the puncture member 550 are each at least partially disposed within the inner volume 536 defined by the transfer adapter 520. Moreover, at least a portion of the fluid reservoir 510 can be selectively disposed within the inner volume 536, as described in further detail herein.

As described above with reference to the transfer adapter 220 of FIGS. 2-8, the annular walls 525 of the transfer adapter 520 can include a first cylindrical portion 526 (also referred to herein as "first portion"), a second cylindrical portion 528 (also referred to herein as "second portion"), and a tapered portion 527 disposed therebetween. The arrangement of the annular walls 525 can be substantially similar to the arrangement of the annular walls 225 of the transfer adapter 220 described above with reference to FIGS. 2 and 5. Accordingly, a diameter a portion of the inner volume 536 (e.g., an inner diameter) defined by the annular walls 525 can be related to a shape of at least a portion of the fluid reservoir 510, as described in further detail herein.

As shown in FIG. 20, the annular walls 525 include an inner surface 534 that include and/or define a set of threads 535. The threads 535 can be, for example, one or more protrusions that extend from the inner surface 534 to substantially circumscribe the first portion 526 of the annular walls 525. More particularly, the threads 535 can extend in a substantially helical manner from a first end portion disposed adjacent to the tapered portion 527 of the annular walls 525 to a second end portion adjacent to a distal end portion of the first portion 526 of the annular walls 525. As shown, the threads 520 are spaced apart a substantially uniform distance. In this manner, the distal end portion 511 of the fluid reservoir 510 can be inserted into the space between the first end portion of the threads 535 and the adjacent thread 535 and can be rotated such that the distal end portion 511 of the fluid reservoir 510 is advanced along the threads 535. In this manner, the fluid reservoir 510 can be rotated to move the fluid reservoir 510 in the distal direction between the first position and the second position, as described in further detail herein.

As shown in FIG. 19, the disinfection member 540 is movably disposed within the inner volume 536 of the transfer adapter 520. More particularly, the disinfection member 540 can be disposed in the inner volume 536 and can be transitioned between a first configuration (see e.g., FIG. 22) and a second configuration (see e.g., FIG. 23). In some embodiments, the disinfection member 540 can have a diameter that is related to a diameter of at least a portion of the inner volume 536. For example, as shown in FIG. 19, the disinfection member 540 can be disposed along the first portion 526 of the annular walls 525. In this manner, the disinfection member 540 can have a diameter that is sufficiently large to define a friction fit with at least a portion of the inner surface 534 such that the relative position of the disinfection member 540 is retained until an external force is applied to the disinfection member 540 that is sufficient to overcome the friction fit, as described in further detail herein.

Figure 21:
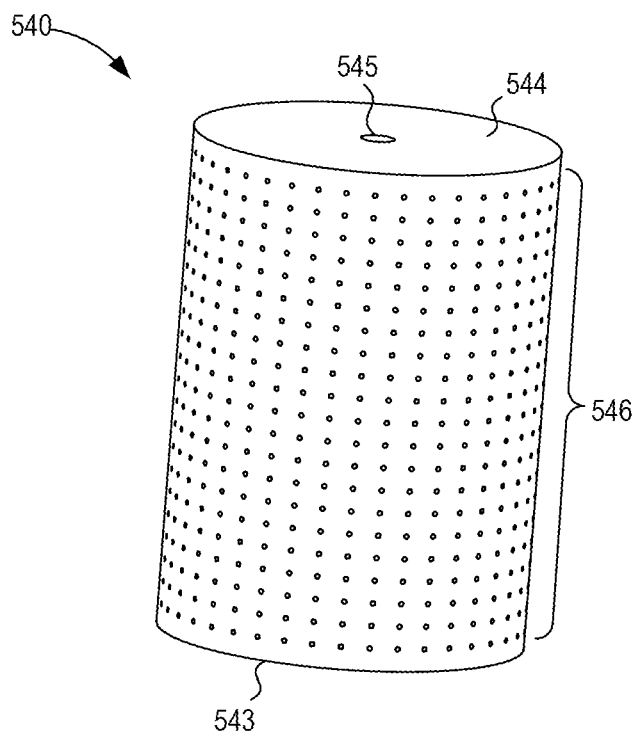
FIG. 21 is a perspective view of a disinfection member included in the transfer adapter of FIG. 19.

The disinfection member 540 can be, for example, a pad, a swab, a sponge, and/or the like that can include a disinfecting agent. The disinfection member 540 includes a first surface 543 and a second surface 544, opposite the first surface 543. In some embodiments, the disinfection member 540 can include and/or can define a portion that is substantially porous. For example, as shown in FIG. 21, the disinfection member 540 can define a set of holes 546 that extend substantially through the disinfection member 540. In this manner, the disinfection member 540 can act as a substrate that can suspend the disinfection agent. As described in further detail herein, when the fluid reservoir 510 is placed in its first position within the inner volume 536, the first surface 543 of the disinfection member 540 is placed in contact with the surface 512 of the fluid reservoir 510 to substantially disinfect the surface 512. Moreover, the second surface 544 of the disinfection member 540 can be in contact with a distal end of the inner surface 534 such that, when the fluid reservoir 510 is moved to the second position, the disinfection member 540 is compressed, thereby transitioning the disinfection member 540 from its first configuration to its second configuration, as described in further detail herein.

Although not shown in FIGS. 18-23, the collection device 500 can include a seal or the like that can be removably coupled to, for example, a proximal surface of the transfer adapter 520. The seal can be any suitable configuration. For example, in some embodiments, the seal can be substantially similar to the seal 238 described above with reference to FIG. 2. In this manner, the seal can fluidically isolate the inner volume 536 to substantially maintain the sterility of the inner volume 536 and/or the puncture member 550 and disinfection member 540 disposed therein. Moreover, by fluidically isolating the inner volume 536, the seal can maintain a relative humidity within the inner volume 536 that is sufficient to substantially prevent evaporation of a disinfection agent disposed therein, as described above.

In use, a user (e.g., a doctor, nurse, technician, physician, phlebotomist, etc.) can manipulate the collection device 500 to couple the port 524 to a lumen defining device such as, for example, a peripheral IV, as described above. The lumen defining device can be placed in communication with a bodily-fluid in a patient such that a fluid flow path is defined between a flow of the bodily-fluid within the patient and the lumen defined by the puncture member 550 (e.g., via the port 524). In some instances, with the port 524 coupled to the lumen defining device, the user can manipulate the collection device 500 remove a seal or the like from the transfer adapter 520, as described above with reference to the seal 238.

Figure 22:
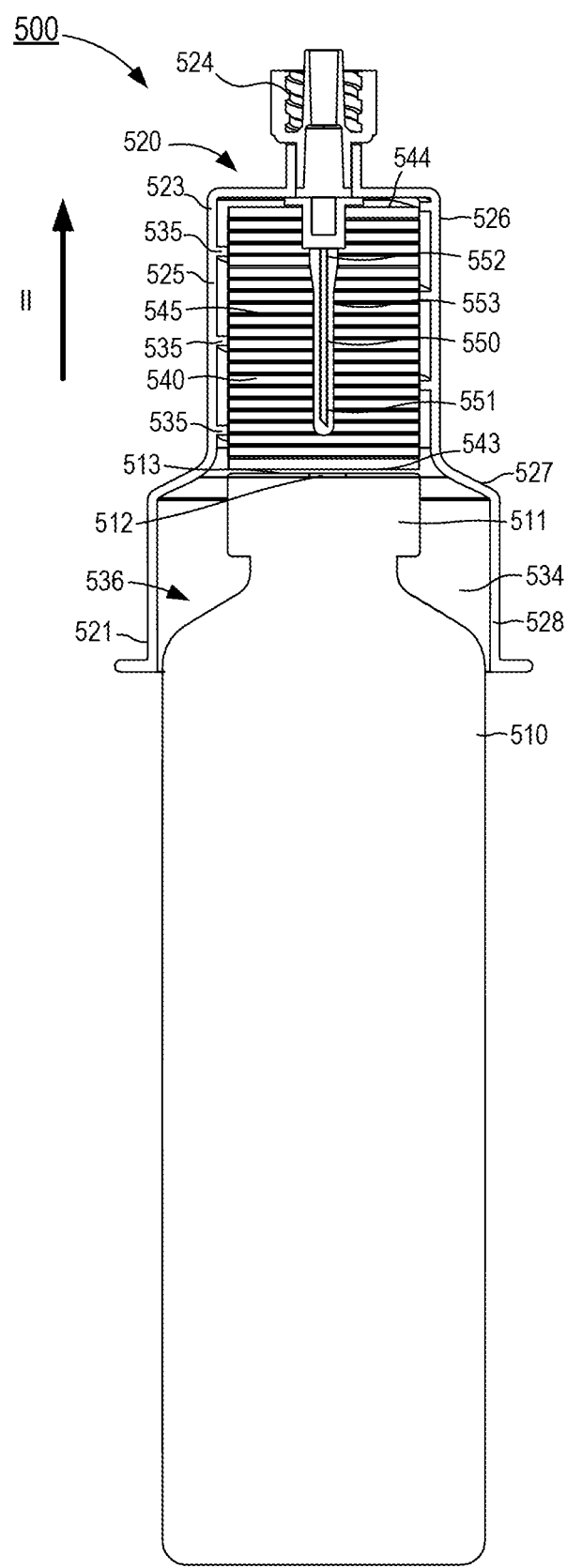
FIG. 22 is a cross-sectional side view of the bodily-fluid collection device of FIG. 18 taken along the line $X_4$-$X_4$, in a first configuration.

The user can move the fluid reservoir 510 in a distal direction relative to the transfer adapter 520 to place the fluid reservoir 510 in the first position within the inner volume 536, thereby placing the collection device 500 in a first configuration, as indicated by the arrow II in FIG. 22. In this manner, the first surface 543 of the disinfection member 540 can contact the surface 512 of the fluid reservoir 510 to substantially disinfect the surface 512. In some embodiments, the disinfection member 540 can be configured to at least partially compress when placed in contact with the surface 512 of the fluid reservoir 510. In such embodiments, by at least partially compressing the disinfection member 540, a disinfecting agent suspended therein can be expelled (e.g., squeezed) from the disinfection member 540 and deposited, at least in part, on the surface 512 of the fluid reservoir 510.

In some embodiments, the user can maintain the fluid reservoir 510 in the first position for a predetermined time period to allow the disinfection agent to disinfect the surface 512 of the fluid reservoir 510. Similarly stated, the user can place the fluid reservoir 510 in the first position and can hold the fluid reservoir 510 substantially in the first position to allow the disinfection member 540 to disinfect the surface 512 of the fluid reservoir 510. In other embodiments, the fluid reservoir 510 need not be held in the first position for the disinfection member 540 to disinfect the surface 512 of the fluid reservoir 510. For example, in some embodiments, the user can move the fluid reservoir 510 in the distal direction and in a substantially continuous manner to place the fluid reservoir 510 in the first position and then the second position.

Figure 23:
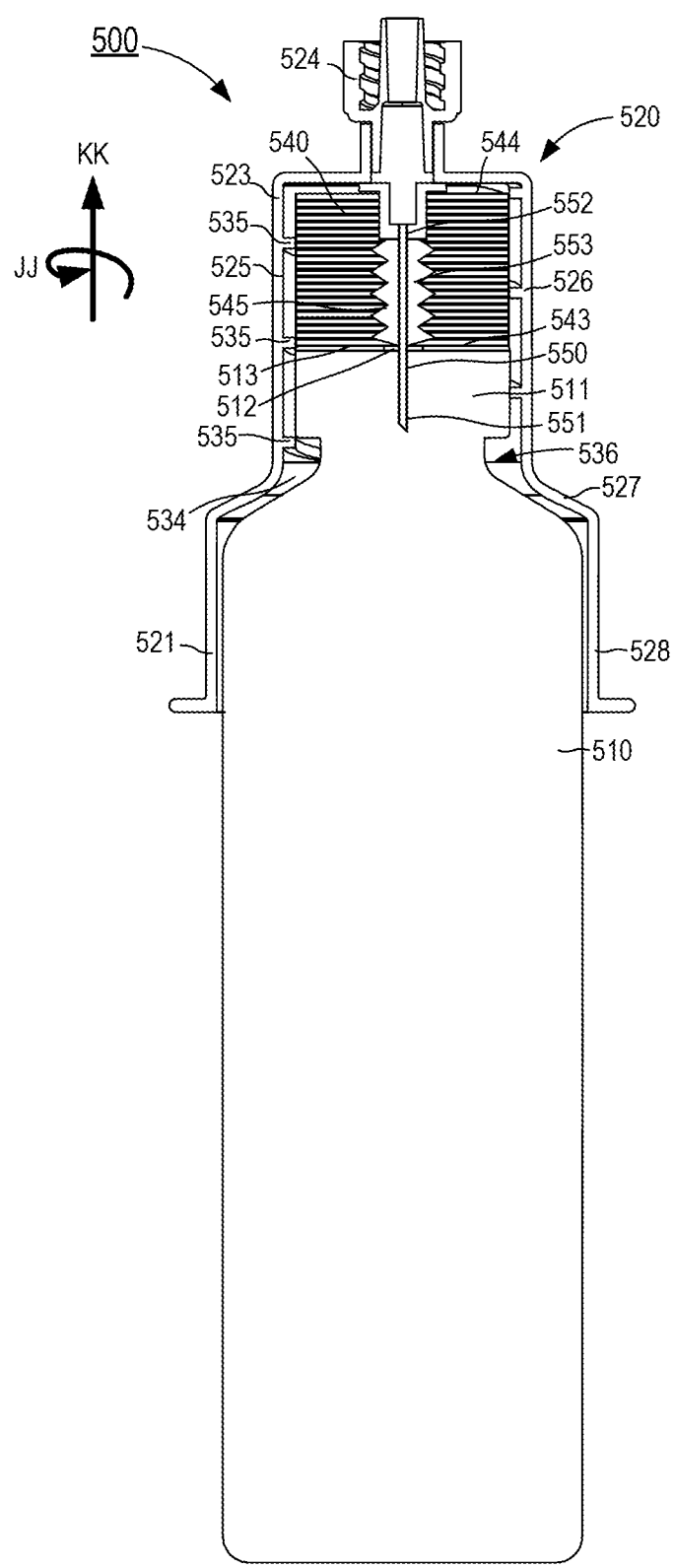
FIG. 23 is a cross-sectional view of the bodily-fluid collection device of FIG. 18 taken along the line $X_4$-$X_4$, in a second configuration.
Figure 24:
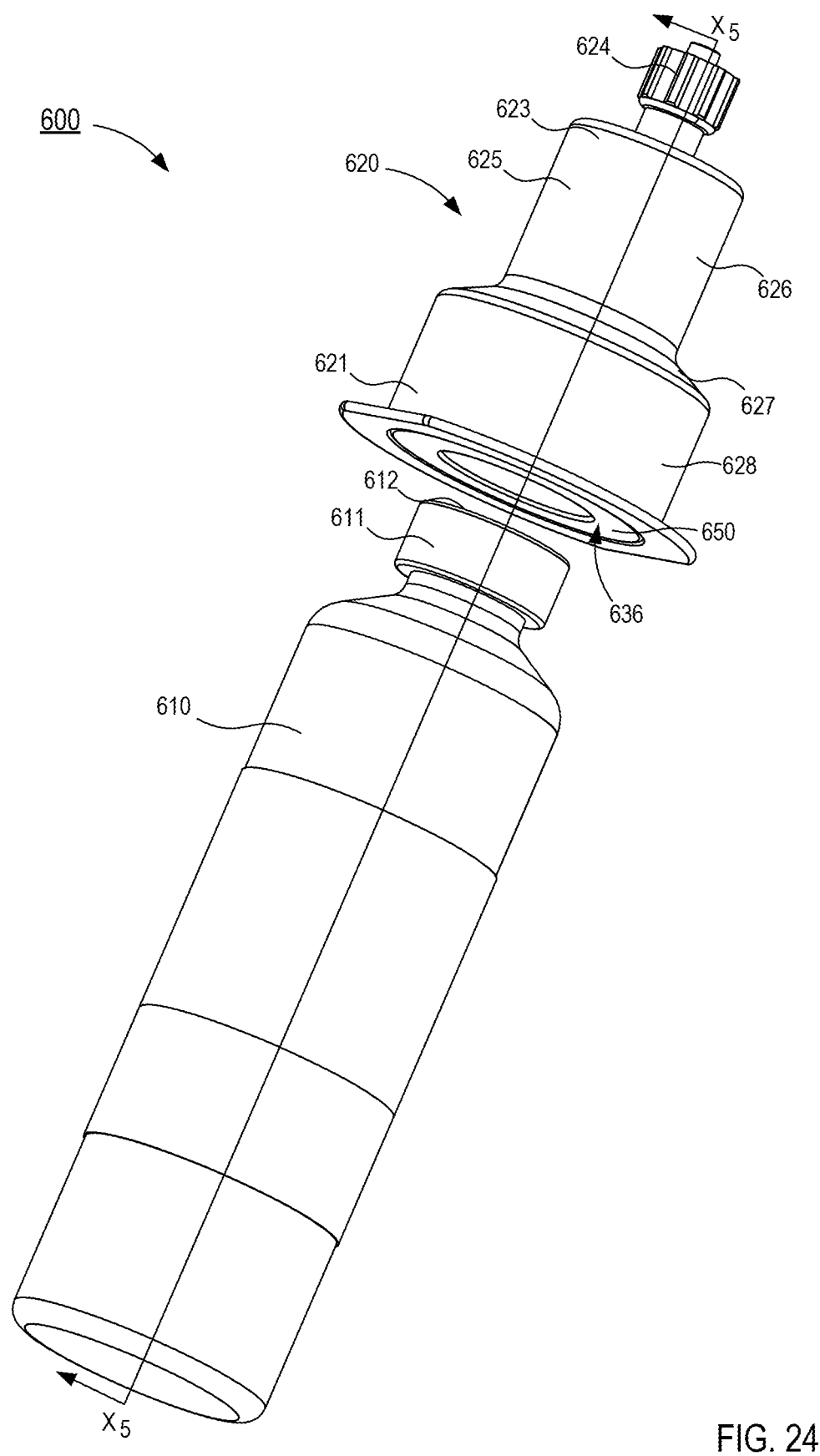
FIG. 24 is a perspective view of a bodily-fluid collection device, according to another embodiment.

With the disinfection member 540 in contact with the surface 512 of the fluid reservoir 510, the user can rotate the fluid reservoir 510 to place the distal end portion 511 in contact with the threads 535 included in and/or defined by the inner surface 534, as indicated by the arrow JJ in FIG. 23. In this manner, the rotation of the fluid reservoir 510 can advance the distal end portion 511 along a surface of the threads and, as such, the fluid reservoir 510 can be moved in the distal direction, as indicated by the arrow KK in FIG. 23. Expanding further, the disinfection member 540 can be maintained in contact with the surface 512 of the fluid reservoir 510 as the fluid reservoir 510 is moved towards the second position. In other words, the distal movement of the fluid reservoir 510 can compress the disinfection member 540 to transition the disinfection member 540 from its first configuration to its second configuration, as shown in FIG. 23.

As shown in FIG. 23, with the fluid reservoir 510 in the second position, the proximal end portion 551 of the puncture member 550 is placed in contact with the port 513 (e.g., pierces the port 513) included in and/or defined by the surface 512, as described in detail above with reference to FIG. 8. Moreover, the distal movement of the fluid reservoir 510 toward the second position can transition the sheath 553 substantially surrounding the puncture member 550 from its first configuration to its second configuration, as described above. Thus, the proximal end portion 551 of the puncture member 550 can extend beyond the sheath 553 to pierce the port 513 of the fluid reservoir 510 such that a portion of the puncture member 550 is disposed in an inner volume defined by the fluid reservoir 510, as shown in FIG. 23. Although not shown in FIGS. 22 and 23, in some embodiments, the proximal end portion 551 of the puncture member 550 can pierce the port 513 prior to the fluid reservoir 510 being placed in the second position. For example, in some embodiments, the user can rotate the fluid reservoir 510 by a quarter of a rotation to place the proximal end portion 551 of the puncture member 550 in contact with the port 513 (e.g., to cause the puncture member 550 to pierce the port 513). In some embodiments, fluid reservoir 510 can be placed in the second position by rotating the fluid reservoir 510 by two or more substantially full rotations. In this manner, the puncture member 550 can be disposed within the fluid reservoir 510 and a lumen defined by the puncture member 550 can be in fluid communication with the inner volume of the fluid reservoir 510. As described above, the number of rotations can be at least partially based on an amount of time and/or contact characteristics (e.g. scrubbing or wiping of surface 512) associated with the disinfecting agent achieving the desired effect of substantially eliminating contaminants and/or other microbes external to the patient's bodily-fluid source.

With the fluid flow path defined between the flow of bodily-fluid in the patient and the lumen defined by the puncture member 550 (e.g., via the lumen defining device and the port 524, as described above), the puncture member 550 can place the fluid reservoir 510 in fluid communication with the flow of bodily-fluid in the patient. As described above, the fluid reservoir 510 can define a negative pressure that can exert a suction force in or on the lumen of the puncture member 550 when the puncture member 550 pierces the fluid reservoir 510 and, in turn, the negative pressure can exert a suction force within, for example, a vein of the patient to urge the bodily-fluid to flow within the fluid flow path to be disposed in the inner volume of the fluid reservoir 510. In some instances, the bodily-fluid can flow within the fluid flow path until a desired volume of bodily-fluid is disposed in the fluid reservoir 510, as described above. With the desired amount of bodily-fluid disposed in the fluid reservoir 510, the fluid reservoir 510 can be rotated in a direction substantially opposite the JJ direction to move the fluid reservoir 510 in the proximal direction relative to the transfer adapter 520, thereby allowing the fluid reservoir 510 to be removed from the transfer adapter 520. In some instances, a second fluid reservoir (not shown in FIG. 5) can be inserted into the transfer adapter 520 and placed in fluid communication with the flow of bodily-fluid in the patient in substantially the same manner as described above. Thus, any suitable number of fluid reservoirs can be inserted into the transfer adapter 520 such that a piercable surface of each fluid reservoir is disinfected prior to receiving a flow of bodily-fluid. As such, the amount of contaminants and/or microbes transferred to a bodily-fluid sample from, for example, a piercable surface of a fluid reservoir can be reduced and/or substantially eliminated. Moreover, by allowing the disinfection agent on the surface 512 of the fluid reservoir 510 to substantially evaporate prior to the puncture member 550 piercing the surface 510, the likelihood of the disinfection agent being transferred to the flow of the bodily-fluid and/or to the inner volume of the fluid reservoir 510 can be reduced and/or substantially eliminated.

Although the collection devices 200 (FIGS. 2-8), 300 (FIGS. 9-12), 400 (FIGS. 13-17), and 500 (FIGS. 18-23) are shown above as including the disinfection members 240, 340, 440, and 540, respectively, that are each disposed within the transfer adapters 220, 320, 420, and 520, respectively, while disinfecting a fluid reservoir, in other embodiments, a collection device can include a disinfection member that can be temporarily disposed within a transfer adapter. For example, FIGS. 24-30 illustrate a bodily-fluid collection device 600 (also referred to herein as "collection device") according to another embodiment. The collection device 600 includes a transfer adapter 620, a set of disinfection members 640 (see e.g., FIG. 24), a puncture member 650 (see e.g., FIG. 6), and a fluid reservoir 610.

Some aspects of the collection device 600 can be similar in form and function as corresponding aspects of the collection device 200, described above with reference to FIGS. 2-8. For example, the transfer adapter 620 can be substantially similar in form and function as the transfer adapter 220 described above. Thus, aspects of the transfer adapter 620 are described below to identify parts and/or portions, however, similar aspects are not described in further detail herein. The transfer adapter 620 has a proximal end portion 621 and a distal end portion 623, and defines an inner volume 636. As described above, at least a portion of the puncture member 650 can be disposed within the inner volume 636 (see e.g., FIG. 25). Moreover, at least a portion of each disinfection member 640 can be temporarily disposed within the inner volume 636, as described in further detail herein. The transfer adapter 620 can include a set of annular walls 625 having a first portion 626, a second portion 628, and a tapered portion 627, as described with above with reference to the annular walls 225 of the transfer adapter 220. The proximal end portion 621 can be substantially open and configured to movably receive the fluid reservoir 610. The distal end portion 623 can include a port 624 that can be substantially similar to the port 224 included in the transfer adapter 220.

The puncture member 650 can be substantially similar in form and function as the puncture member 250, described above with reference to FIGS. 3-8. Thus, aspects of the puncture member 650 are described below to identify parts and/or portions, however, similar aspects are not described in further detail herein. The puncture member 650 can include a proximal end portion 651 and a distal end portion 652 (see e.g., FIG. 25). The distal end portion 652 can be coupled to the port 624 of the transfer adapter 620 (e.g., physically and fluidically coupled), and the proximal end portion 651 can be selectively placed in contact with a surface of the fluid reservoir 610, as described above with reference to the puncture member 250. Moreover, the puncture member 650 can be at least temporarily disposed within a sheath 653 that can be substantially similar to the sheath 253 described above. The sheath 653 can be transitioned between a first configuration, in which the sheath 653 substantially surrounds the puncture member 650, and a second configuration, in which a portion of the puncture member 650 extends in a proximal direction beyond a surface of the sheath 653, as described above with reference to the sheath 253 (see e.g., FIGS. 6 and 8).

The fluid reservoir 610 can be substantially similar in form and function as the fluid reservoir 210, described above with reference to FIG. 5. Thus, aspects of the fluid reservoir 610 are described below to identify parts and/or portions, however, similar aspects are not described in further detail herein. The fluid reservoir 610 can include a distal end portion 611 having a surface 612 that defines a port 613, as described above with reference to the fluid reservoir 210 (see e.g., FIG. 5). The fluid reservoir 610 can be inserted into the inner volume 636 of the transfer adapter 620 and can be moved to a first position and a second position relative to the transfer adapter 620, as described in further detail herein.

Figure 25:
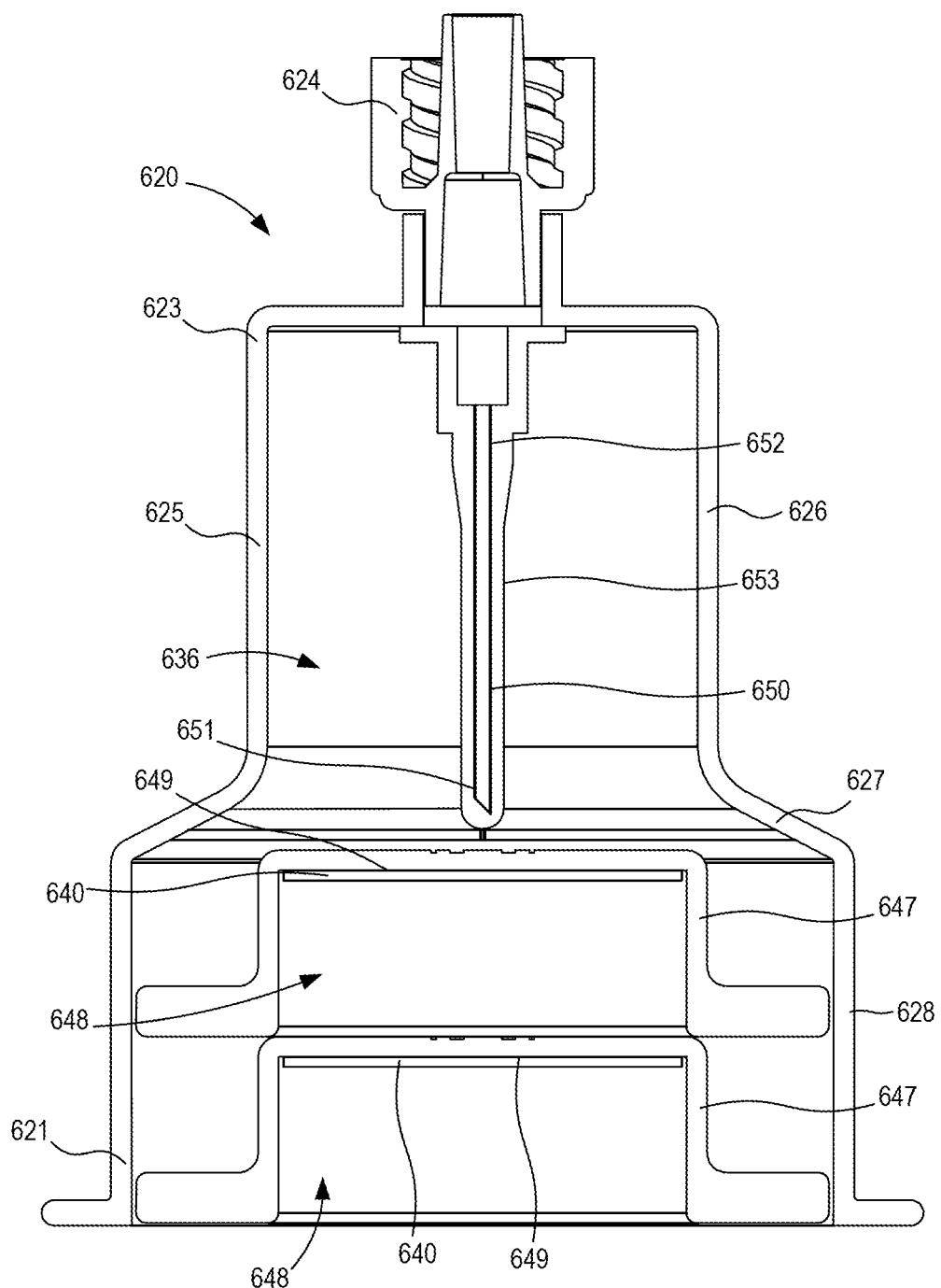
FIG. 25 is a cross-sectional view of a transfer adapter included in the bodily-fluid collection device of FIG. 24 taken along the line $X_5$-$X_5$.
Figure 26:
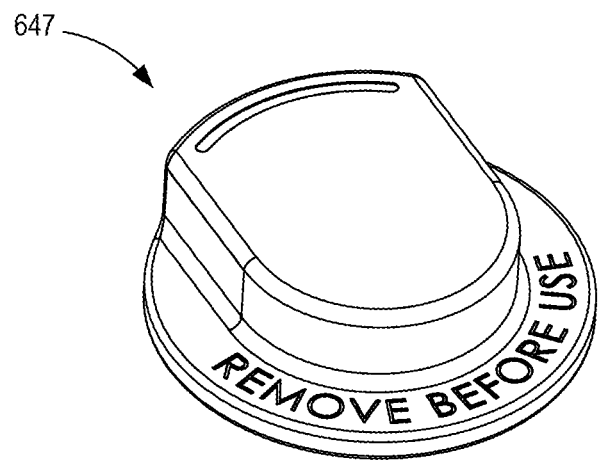
FIGS. 26 and 27 are a top perspective view and a bottom perspective view, respectively, of a disinfection member included in the transfer adapter of FIG. 25.
Figure 27:
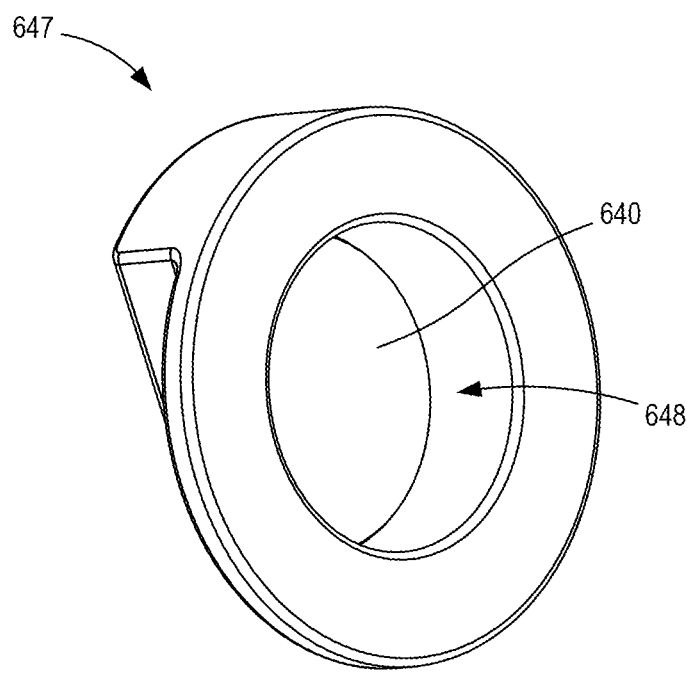

As shown in FIGS. 25-27, the disinfection members 640 can each be disposed within an inner volume 648 defined by a cap 647. More particularly, the disinfection members 640 can be coupled to a distal surface 649 that defines at least a portion of the inner volume 648 (e.g., via an adhesive, a friction fit, a physical indentation in the wall of the transfer adapter 620, etc.). The caps 647 are each at least temporarily disposed within the inner volume 636 of the transfer adapter 620. In some embodiments, a surface of the caps 647 can define a friction fit with an inner surface of the transfer adapter 620 to at least temporarily retain each caps 647 (and therefore, each disinfection member 640) within the inner volume 636 of the transfer adapter 620. Although shown in FIG. 25 as including a set of two caps 647, in other embodiments, the transfer adapter 620 can house more or less than two caps 647. For example, in some embodiments, a single cap 647 (including a disinfection member 640) can be disposed within the inner volume 636. Moreover, although the caps 647 are disposed in a substantially stacked arrangement, in other embodiments, the second portion 628 of the transfer adapter 620 can have a diameter that is sufficient to allow the caps 647 to be disposed in the inner volume 636 in a side-by-side arrangement (e.g., coplanar).

The disinfection member 640 can be, for example, a pad, a swab, a sponge, and/or the like that can include a disinfecting agent. In some embodiments, at least a surface of the disinfection members 640 can be impregnated with a disinfecting agent such as, those described above. In some embodiments, the disinfection members 640 can include and/or can define a portion that is substantially porous, for example, to act as a substrate for the disinfection agent. As described in further detail herein, the fluid reservoir 610 can be inserted into the inner volume 647 defined by the cap 648 to be placed in contact with the disinfection member 640 (e.g., to be placed in the first position within the inner volume 636). In some embodiments, the distal end portion 611 of the fluid reservoir 610 can form a friction fit with an inner surface of the cap 647 defining the inner volume 648. As such, the fluid reservoir 610 can be disposed within the inner volume 648 defined by the cap 647 and moved in a proximal direction to remove the cap 647 from the inner volume 636 defined by the transfer adapter 620, as described in further detail herein.

Although not shown in FIGS. 24-30, can include a seal or the like that can be removably coupled to, for example, a proximal surface of the transfer adapter 620. The seal can be any suitable configuration. For example, in some embodiments, the seal can be substantially similar to the seal 238 described above with reference to FIG. 2. In this manner, the seal can fluidically isolate the inner volume 636 to substantially maintain the sterility of the inner volume 636 and/or the puncture member 650 and disinfection member 640 disposed therein. Moreover, by fluidically isolating the inner volume 636, the seal can maintain a relative humidity within the inner volume 636 that is sufficient to substantially prevent evaporation of a disinfection agent disposed therein, as described above. In other embodiments, the seal can be affixed to each individual cap 647 to maintain the desired level of disinfecting agent saturation of the disinfection members 640.

In use, a user (e.g., a doctor, nurse, technician, physician, phlebotomist, etc.) can manipulate the collection device 600 to couple the port 624 to a lumen defining device such as, for example, a peripheral IV, a standard winged butterfly needle, and/or a syringe as described above. The lumen defining device can be placed in communication with a bodily-fluid in a patient such that a fluid flow path is defined between a flow of the bodily-fluid within the patient and the lumen defined by the puncture member 650 (e.g., via the port 624). In some instances, with the port 624 coupled to the lumen defining device, the user can manipulate the collection device 600 remove a seal or the like from the transfer adapter 620, as described above with reference to the seal 238.

Figure 28:
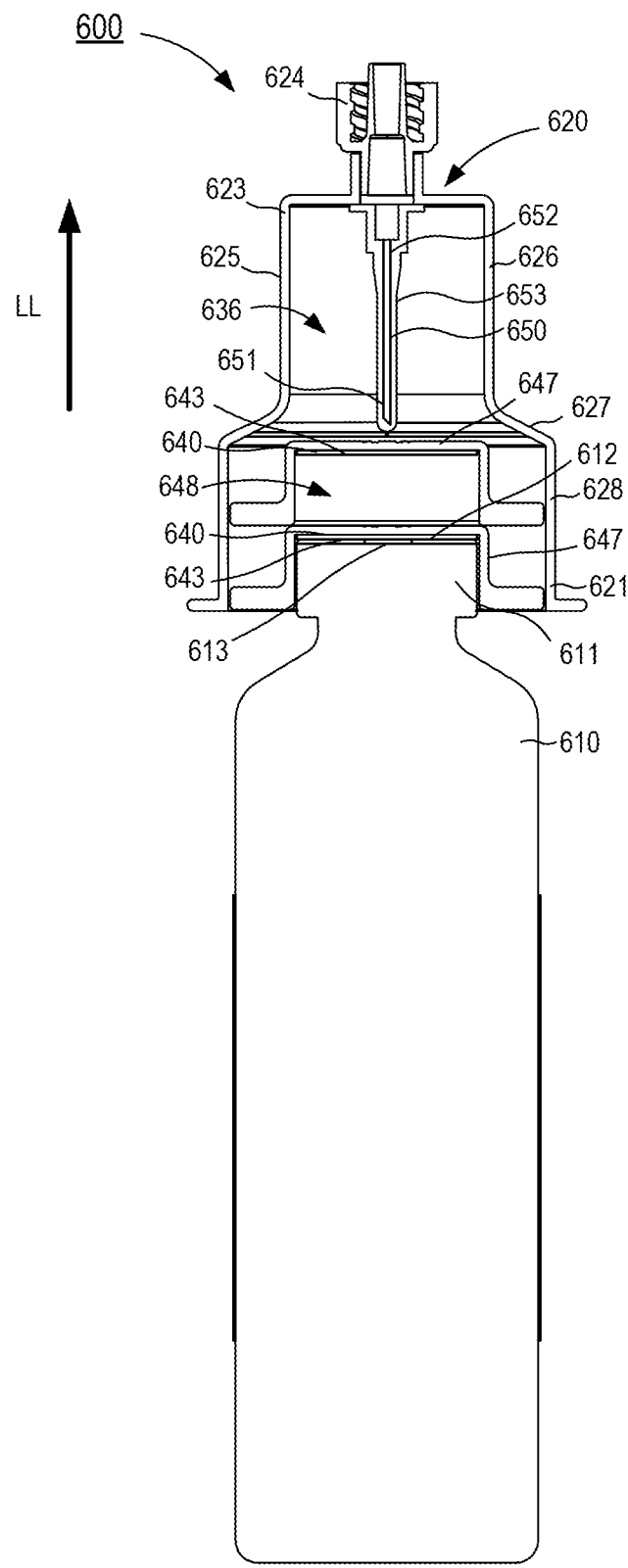
FIG. 28 is a cross-sectional side view of the bodily-fluid collection device of FIG. 24 taken along the line $X_4$-$X_4$, in a first configuration.

The user can move the fluid reservoir 610 in a distal direction relative to the transfer adapter 620 to place the fluid reservoir 610 in the first position within the inner volume 636, thereby placing the collection device 600 in a first configuration, as indicated by the arrow LL in FIG. 28. In this manner, the distal end portion 611 of the fluid reservoir 610 can be inserted into the inner volume 648 defined by the cap 647 (e.g., the cap 647 adjacent to the proximal end portion 621 of the transfer adapter 620 in FIG. 28) to place the surface 612 of the fluid reservoir 610 in contact with the disinfection member 640. Thus, the disinfection member 640 can disinfect the surface 612. In some embodiments, the disinfection member 640 can be configured to, for example, compress when placed in contact with the surface 612 of the fluid reservoir 610. In such embodiments, by compressing the disinfection member 640, a disinfecting agent suspended in, for example, a porous substrate of the disinfection member 640 can be expelled (e.g., squeezed) from the disinfection member 640 and deposited, at least in part, on the surface 612 of the fluid reservoir 610.

Figure 29:
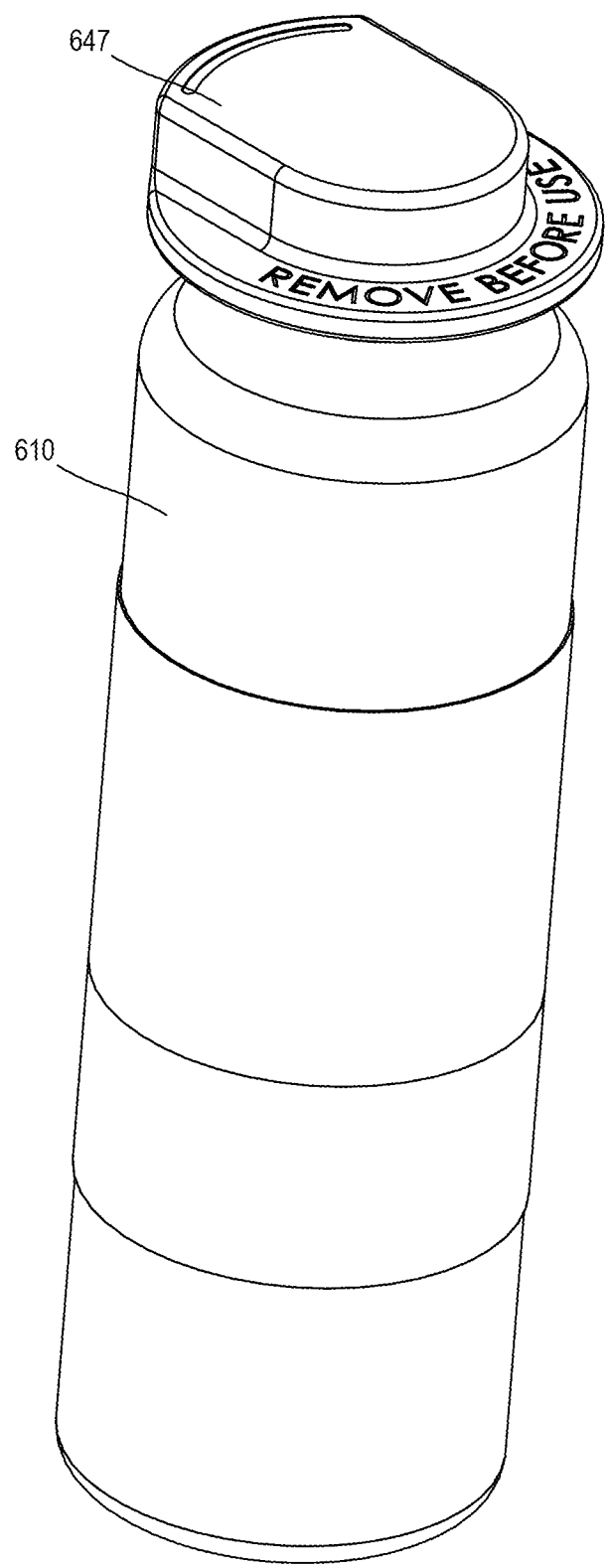
FIG. 29 is a perspective view of the disinfection member of FIG. 26 coupled to a fluid reservoir.

As shown in FIG. 29, with the surface 612 of the fluid reservoir 610 in contact with the disinfection member 640, the fluid reservoir 610 can be moved in a proximal direction to remove the fluid reservoir 610 from the inner volume 636 defined by the transfer adapter 620. Moreover, with the distal end portion 611 of the fluid reservoir 610 defining a friction fit with the inner surface of the cap 647, the cap 647 is also removed, substantially concurrently, from the inner volume 636 defined by the transfer adapter 620. In this manner, the surface 612 of the fluid reservoir 610 can be maintained in contact with the disinfection member 640 for a predetermined or variable time period that is sufficient to substantially disinfect the surface 612. Furthermore, by removing the cap 647 that was in the proximal position within the inner volume 636 of the transfer adapter 620, a second fluid reservoir (not shown in FIGS. 24-30) can be inserted into the inner volume 636 of the transfer adapter 620 and placed in its first position to place a surface of that fluid reservoir in contact with the second disinfection member 640, in a similar manner as described with reference to the fluid reservoir 610. Thus, the second fluid reservoir can be moved in the proximal direction to remove the second fluid reservoir and the second cap 647 (e.g., the cap 647 in the distal position in FIG. 25). In this manner, the disinfection member 640 included in that cap 647 can be maintained in contact with the surface of the second fluid reservoir to substantially disinfect the surface. The positioning of the caps 647 within the inner volume 636 of the transfer adapter 620, for example, can prevent a user from gaining access to the bodily-fluid source via the puncture member 650 until the caps 647 have been removed. The physical obstruction created by the placement of the caps 647 can significantly increase the likelihood that a user would follow the steps intended to disinfect the surface 612 of the fluid reservoir 610 prior to initiating contact with the puncture member 650 to transfer bodily-fluid into the fluid reservoir 610.

Figure 30:
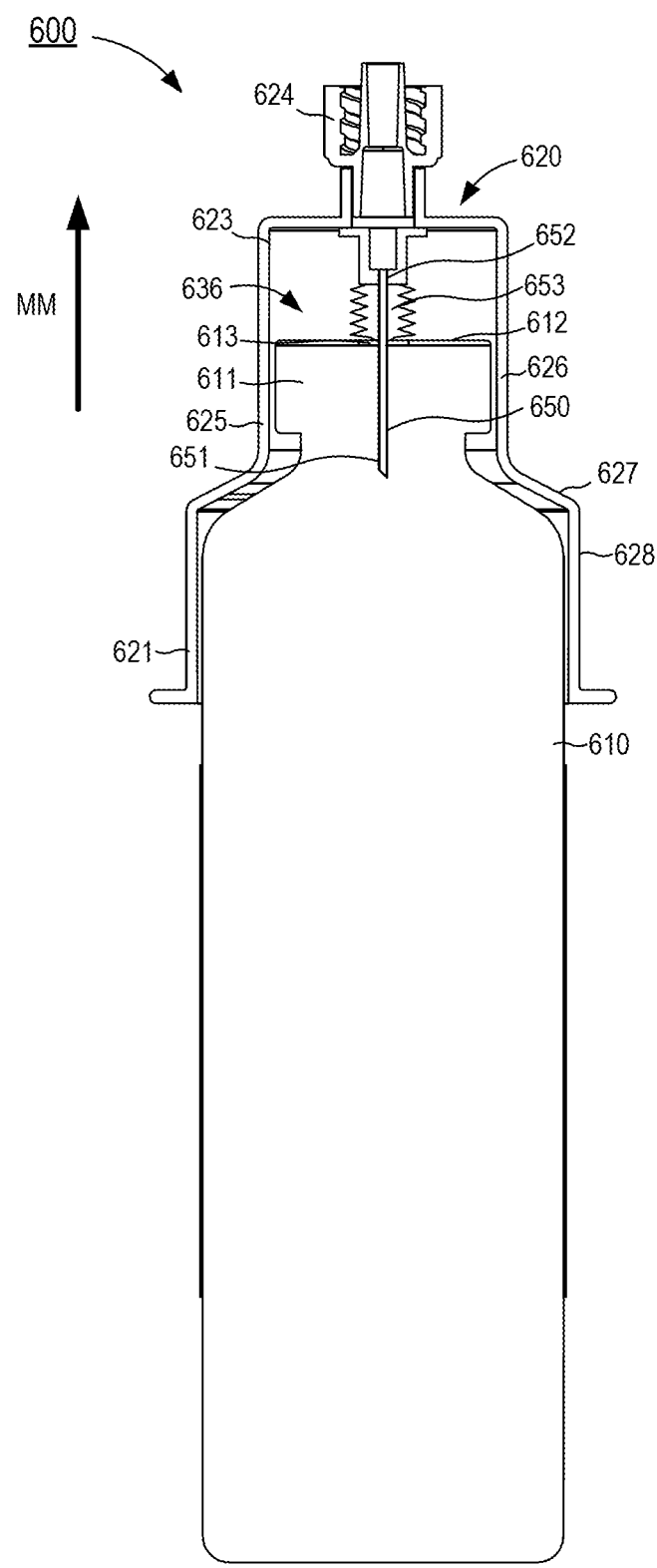
FIG. 30 is a cross-sectional view of the bodily-fluid collection device of FIG. 25 taken along the line $X_5$-$X_5$, in a second configuration.

In some instances, after a predetermined or variable time period of being in contact with the disinfection member 640, the user can remove the distal end portion 611 of the fluid reservoir 610 from the inner volume 648 of the cap 647. As shown in FIG. 30, once removed from the cap 647, the user can insert the fluid reservoir 610 into the inner volume 636 of the transfer adapter 620 to place the fluid reservoir 610 in the second position, as indicated by the arrow MM in FIG. 30. With the fluid reservoir 610 in the second position, the proximal end portion 651 of the puncture member 650 is placed in contact with the port 613 (e.g., pierces the port 613) included in and/or defined by the surface 612, as described in detail above with reference to FIG. 8. Moreover, the distal movement of the fluid reservoir 610 toward the second position can transition the sheath 653 substantially surrounding the puncture member 650 from its first configuration to its second configuration, as described above. Thus, the proximal end portion 651 of the puncture member 650 can extend beyond the sheath 653 to pierce the port 613 of the fluid reservoir 610 such that a portion of the puncture member 650 is disposed in an inner volume defined by the fluid reservoir 610, as shown in FIG. 30.

With the puncture member 650 defining a lumen and with the fluid reservoir 610 in the second position, the portion of the puncture member 650 can be disposed within the fluid reservoir 610 such that the lumen defined by the puncture member 650 is in fluid communication with the inner volume of the fluid reservoir 610. Thus, with the fluid flow path defined between the flow of bodily-fluid in the patient and the lumen defined by the puncture member 650 (e.g., via the lumen defining device and the port 624, as described above), the puncture member 650 can place the fluid reservoir 610 in fluid communication with the flow of bodily-fluid in the patient. As described above, the fluid reservoir 610 can define a negative pressure that can exert a suction force in or on the lumen of the puncture member 650 when the puncture member 650 pierces the fluid reservoir 610 and, in turn, the negative pressure can exert a suction force within, for example, a vein of the patient to urge the bodily-fluid to flow within the fluid flow path to be disposed in the inner volume of the fluid reservoir 610. In some instances, the bodily-fluid can flow within the fluid flow path until a desired volume of bodily-fluid is disposed in the fluid reservoir 610, as described above. With the desired amount of bodily-fluid disposed in the fluid reservoir 610, the fluid reservoir 610 can be moved in the proximal direction to, for example, remove the fluid reservoir 610 from the inner volume 636 of the transfer adapter 620.

In some instances, the user can remove the second fluid reservoir from the inner volume 648 of the cap 647 in which it is disposed. Thus, with the fluid reservoir 610 removed from the inner volume 636 and with the second fluid reservoir removed from the associated cap 647, the second fluid reservoir can be inserted into the transfer adapter 620 and placed in fluid communication with the flow of bodily-fluid in the patient in substantially the same manner as described above. As such, the amount of contaminants and/or microbes transferred to a bodily-fluid sample from, for example, the piercable surface of the fluid reservoir 610 and/or the second fluid reservoir (not shown) can be reduced and/or substantially eliminated.

Figure 31:
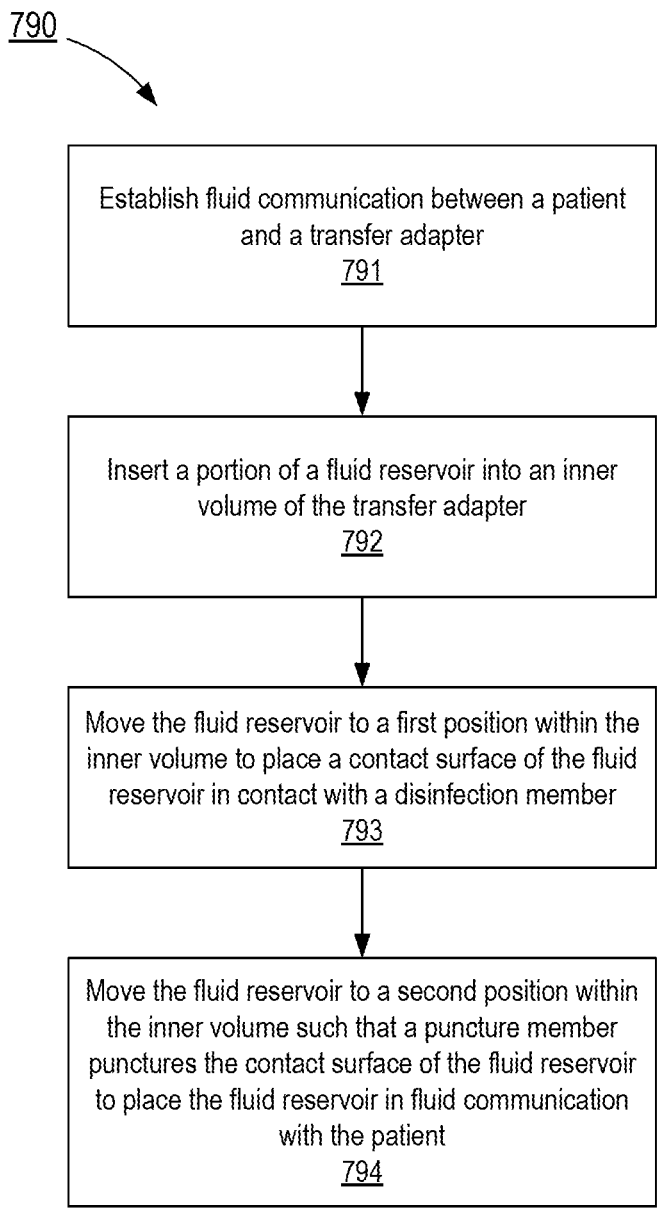
FIG. 31 is a flowchart illustrating a method of procuring a bodily-fluid sample from a patient with reduced contamination from externally residing microbes according to an embodiment.

FIG. 31 is a flowchart illustrating a method 790 of procuring a bodily-fluid sample from a patient with reduced contamination from externally residing microbes according to an embodiment. In some embodiments, the method 790 includes establishing fluid communication between a patient and a transfer adapter, at 791. The transfer adapter can be any suitable device or mechanism described herein. For example, in some embodiments, the transfer adapter can be substantially similar to transfer adapter 200 described above with reference to FIGS. 2-8. In this manner, the transfer adapter can include a proximal end portion and a distal end portion, and can define an inner volume within which a disinfection member and a puncture member are disposed. The distal end portion of the transfer adapter can include a port that is configured to be placed in fluid communication with the patient. The puncture member is configured to be fluidically coupled to the port to be placed in fluid communication with the patient, as described above with reference to the transfer adapter 220 and the puncture member 250. The disinfection member can be substantially similar to any of the disinfection members described herein. In this manner, the disinfection member can be configured to substantially disinfect a surface of a fluid reservoir when placed in contact therewith.

A portion of a fluid reservoir is inserted in the inner volume of the transfer adapter, at 792. For example, in some embodiments, the proximal end portion of the transfer adapter can be substantially open and configured to movably receive the portion of the fluid reservoir. In some embodiments, the transfer adapter can be coupled to a seal or the like that can be configured to fluidically isolate at least a portion of the inner volume of the transfer adapter. In such embodiments, the seal can be removed prior to inserting the fluid reservoir into the inner volume of the transfer adapter. In other embodiments, the seal can include, for example, a frangible portion that can be deformed and/or otherwise reconfigured to allow the fluid reservoir to be inserted into the inner volume.

The fluid reservoir is moved to a first position within the inner volume to place a contact surface of the fluid reservoir in contact with the disinfection member, at 793. For example, the contact surface can be a distal surface of the fluid reservoir that can include and/or define a port. In some embodiments, the fluid reservoir can be moved in a distal direction relative to the transfer adapter to place the contact surface in the contact with the disinfection member. In this manner, the disinfection member can substantially disinfect the contact surface. In some embodiments, the disinfection member can include a surface that is disposed at, near, and/or substantially coplanar with a proximal surface of the transfer adapter. As such, the first position of the fluid reservoir can be associated with the insertion of the portion of the fluid reservoir into the inner volume in which the contact surface of the fluid reservoir is placed in contact with the disinfection member in a substantially concurrent process.

The fluid reservoir is moved to a second position within the inner volume such that the puncture member punctures the contact surface of the fluid reservoir to place the fluid reservoir in fluid communication with the patient, at 794. For example, in some embodiments, the fluid reservoir can be moved in the distal direction to the second position and the puncture member can pierce the port included in the contact surface to place the puncture member in fluid communication with an inner volume of the fluid reservoir. In some embodiments, as the fluid reservoir is moved from the first position to the second position, the fluid reservoir can transition the disinfection member from a first configuration to a second configuration. For example, in some embodiments, the disinfection member can be transitioned from a substantially closed configuration to a substantially open position to allow the fluid reservoir to pass therethrough. In other embodiments, the fluid reservoir can transition the disinfection member from a substantially non-compressed configuration to a substantially compressed configuration when moved to the second position. In such embodiments, the disinfection member can be maintained in contact with the contact surface of the fluid reservoir. In other embodiments, the contact surface need not remain in contact with the disinfection member. In such embodiments, at least a portion of the transfer adapter can be vented to allow a disinfection agent to evaporate from the contact surface, as described above with reference to the transfer adapter 320. In some embodiments, the puncture member can be disposed within a sheath. In such embodiments, as the fluid reservoir is moved to the second position, the sheath can be transitioned from a first configuration in which proximal end portion of the puncture member is disposed within the sheath to a second configuration in which the proximal end portion extends beyond a surface of the sheath to puncture the contact surface of the fluid reservoir.

With the fluid reservoir in fluid communication with the patient (e.g., via at least the puncture member and the port), the fluid reservoir can receive a flow of bodily-fluid from the patient. In some embodiments, the fluid reservoir can define, for example, a negative pressure that can draw the bodily-fluid into the fluid reservoir. Moreover, by placing the contact surface of the fluid reservoir in contact with the disinfection member, contaminants such as microbes or the like residing on the contact surface of the fluid reservoir are substantially killed and/or removed prior the contact surface being punctured by the puncture member. Thus, the bodily-fluid sample contained in the fluid reservoir can be substantially free from externally residing microbes that could otherwise be transferred from the contact surface to the bodily-fluid sample during procurement.

Figure 32:
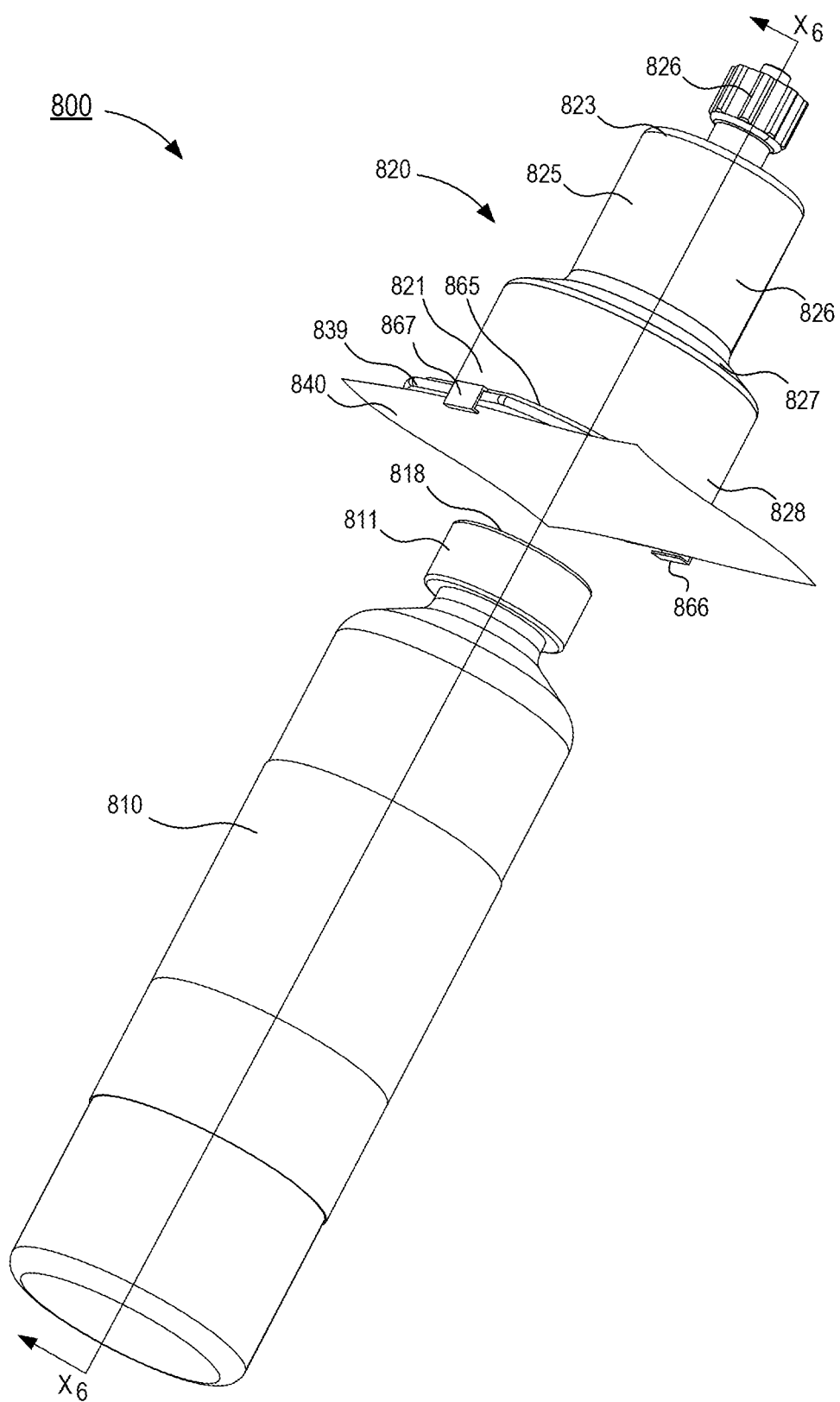
FIG. 32 is a perspective view of a bodily-fluid collection device, according to another embodiment.
Figure 33:
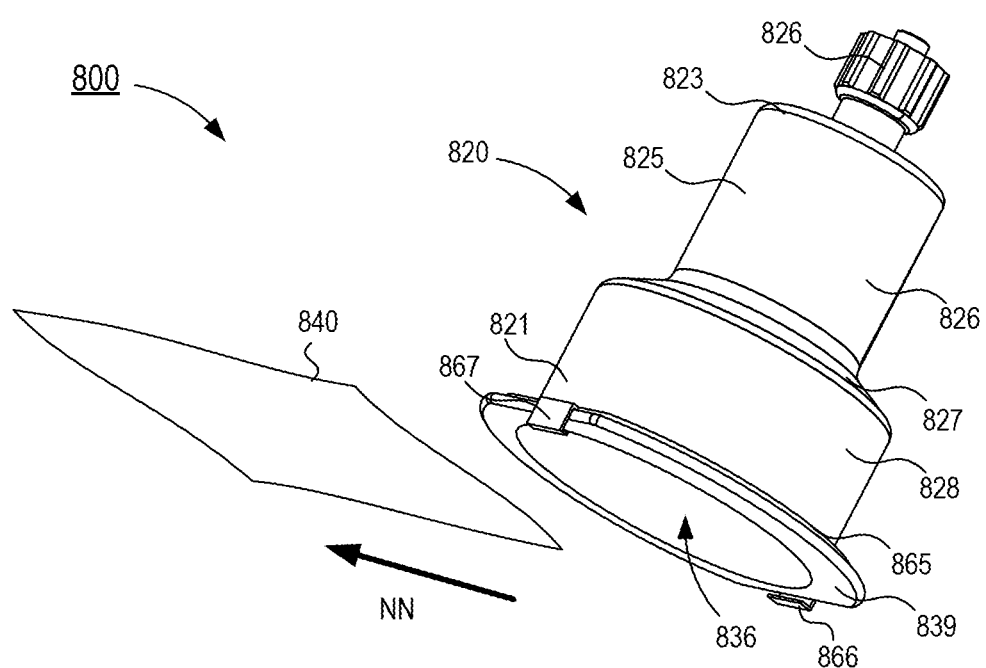
FIG. 33 is a perspective view of a transfer adapter included in the bodily-fluid collection device of FIG. 32.
Figure 34:
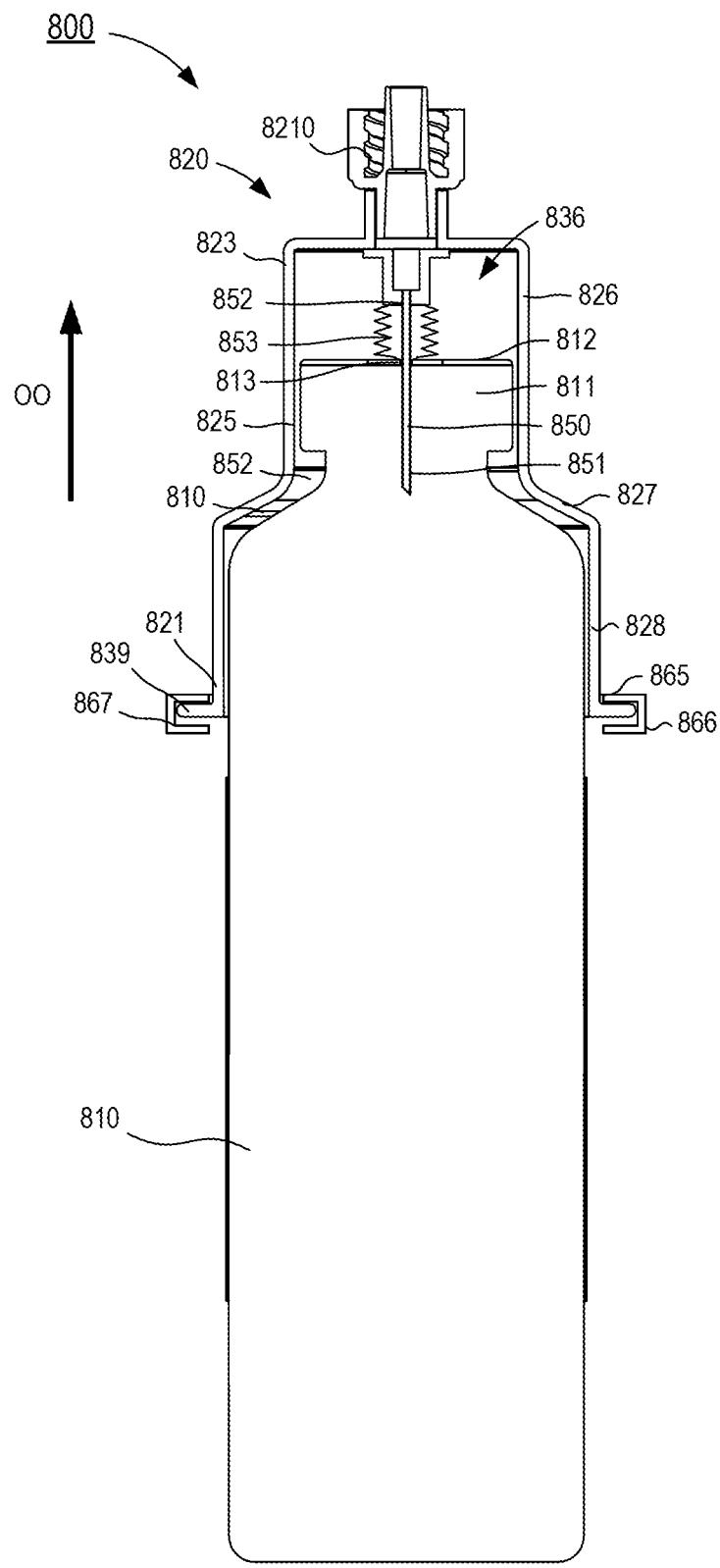
FIG. 34 is a cross-sectional view of the bodily-fluid collection device of FIG. 32 taken along the line $X_6$-$X_6$.

As described above with reference to FIGS. 24-30, in some embodiments, a transfer adapter can be at least temporarily coupled to a disinfection member, which can be removed from the transfer adapter and applied to a fluid reservoir prior to use. For example, FIGS. 32-34 illustrate a perspective view of a bodily-fluid collection device 800, according to another embodiment. As shown in FIG. 32, the bodily-fluid collection device 800 includes a transfer adapter 820, a disinfection member 840, a puncture member 850 (see e.g., FIG. 34), and a fluid reservoir 810. Some aspects of the collection device 800 can be similar in form and/or function as corresponding aspects of the collection device 200, described above with reference to FIGS. 2-8. For example, the transfer adapter 620 can be substantially similar in form and/or function as the transfer adapter 220 and/or any of the transfer adapters 320, 420, 520, and/or 620 described above. Thus, such aspects of the transfer adapter 820 are described below to identify parts and/or portions, however, similar aspects are not described in further detail herein.

The fluid reservoir 810 can be substantially similar in form and function as the fluid reservoir 210, described above with reference to FIG. 5. Thus, aspects of the fluid reservoir 810 are described below to identify parts and/or portions, however, similar aspects are not described in further detail herein. The fluid reservoir 810 includes a distal end portion 811 having a surface 812 that defines a port 813 (as described above). The fluid reservoir 810 is configured to be inserted into the inner volume 836 of the transfer adapter 820 and into fluid communication with the puncture member 850 after, for example, the disinfection member 840 is applied to the surface 812, as described in further detail herein.

The transfer adapter 820 has a proximal end portion 821 and a distal end portion 823, and defines an inner volume 836. As described above with reference to the transfer adapter 220, the transfer adapter 820 includes a set of annular walls 825 having a first portion 826, a second portion 828, and a tapered portion 827. The proximal end portion 821 includes a proximal flange 839 and can be substantially open to movably receive the fluid reservoir 810, as shown in FIGS. 33-34. The distal end portion 823 includes a port 824 that can be substantially similar to the port 224 included in the transfer adapter 220.

As described above with reference to the transfer adapter 220, at least a portion of the puncture member 850 can be disposed within the inner volume 836 (see e.g., FIG. 34). The puncture member 850 can be substantially similar in form and function as the puncture member 250, described above with reference to FIGS. 3-8. Thus, aspects of the puncture member 850 are described below to identify parts and/or portions, however, similar aspects are not described in further detail herein. The puncture member 850 includes a proximal end portion 851 and a distal end portion 852 (see e.g., FIG. 34). The distal end portion 852 is coupled to the port 824 of the transfer adapter 820 (e.g., physically and fluidically coupled), and the proximal end portion 851 can be selectively placed in contact with a surface of the fluid reservoir 810, as described above with reference to the puncture member 250. Moreover, the puncture member 850 can be at least temporarily disposed within a sheath 853 (e.g., similar to the sheath 253 described above) configured to be transitioned between a first configuration, in which the sheath 853 substantially surrounds the puncture member 850, and a second configuration, in which a portion of the puncture member 850 extends in a proximal direction beyond a surface of the sheath 853 (see FIG. 34).

The disinfection member 840 can be any suitable disinfection member configured to substantially sterilize and/or disinfect the surface 812 of the fluid reservoir 810 prior to inserting the distal end portion 811 of the fluid reservoir 810 into the inner volume 836. For example, in this embodiment, the disinfection member 840 can be a wipe such as a cloth, a pad, a sponge, a swab, and/or any suitable substantially saturated absorbent material. Although not shown in FIGS. 32-34, the disinfection member 840 can be disposed within a package, pouch, wrapper, and/or any other suitable non-fluidically permeable covering. As such, the package or the like can maintain the disinfection member 840 in a moist and substantially sterile environment.

The disinfection member 840 can be at least temporarily coupled to the transfer adapter 820. Specifically, in this embodiment, the transfer adapter 820 includes a retention member 865 having a first engagement member 866 and a second engagement member 867, as shown in FIGS. 32-34. The retention member 865 can be and/or can otherwise form an annular ring or the like that is disposed about a portion of the transfer adapter 820. For example, in some embodiments, the retention member 865 can be disposed about the proximal end portion 821 adjacent to and/or otherwise in contact with the proximal flange 839 or the like of the transfer adapter 820. The first engagement member 866 and the second engagement member 867 can be substantially similar and be disposed on substantially opposite sides of the retention member 865. The engagement members 866 and 867 can be any suitable shape, size, and/or configuration. For example, in this embodiment, the engagement members 866 and 867 each form a substantially U-shaped tab, clip, protrusion, extension, etc. Moreover, as shown in FIGS. 32-34, the arrangement of the retention member 865 relative to the transfer adapter 820 is such that a first portion of the engagement members 866 and 867 are disposed on a first side (e.g., a distal side) of the proximal flange 839 and a second portion of the engagement member 866 and 867 are disposed on a second side of the proximal flange 839 (e.g., a proximal side).

As shown in FIG. 32, the engagement members 866 and 867 are configured to engage and/or contact the disinfection member 840 to retain the disinfection member in a substantially fixed position relative to the transfer adapter 820 prior to use. For example, as shown, the disinfection member 840 can be disposed between the second portion of the engagement members 866 and 867, which are disposed on the proximal side of the proximal flange 839, and a proximal surface of the transfer adapter 820. As such, when the disinfection member 840 is disposed between the engagement members 866 and 867 and the proximal surface of the transfer adapter 820, the disinfection member 840 substantially obstructs the open proximal end portion of the transfer adapter 840. In other words, the disinfection member 840 (e.g., disposed within its package or the like) substantially obstructs the inner volume 836 of the transfer adapter 820 from a volume proximal to the disinfection member 840. Thus, to insert a portion of the fluid reservoir 810 into the inner volume 836, for example, a user can remove the disinfection member 840 from the retention member 865, thereby exposing the inner volume 836 of the transfer adapter. Such an arrangement, in some instances, can force a user to comply with a disinfection protocol and/or at least remind the user to disinfect the fluid reservoir 810 prior to inserting the fluid reservoir 810 into the transfer adapter 820.

In use, a user (e.g., a doctor, nurse, technician, physician, phlebotomist, etc.) can manipulate the collection device 800 to couple the port 824 to a lumen defining device such as, for example, a peripheral IV, a standard winged butterfly needle, and/or a syringe as described above. The lumen defining device can be placed in communication with a bodily-fluid in a patient such that a fluid flow path is defined between a flow of the bodily-fluid within the patient and the lumen defined by the puncture member 850 (e.g., via the port 824). With the transfer adapter 820 coupled to the lumen defining the device, the user can manipulate the disinfection member 840 to remove the disinfection member 840 from engagement and/or contact with the retention member 865, as indicated by the arrow NN in FIG. 33. Once removed from the retention member 865, the user can remove the disinfection member 840 from its package or the like (not shown). For example, in some embodiments, the user can tear open the package or the like to remove the disinfection member 840. The user can then apply, wipe, and/or otherwise place the disinfection member 840 in contact with at least the surface 812 of the fluid reservoir 810, thereby substantially sterilizing those surfaces (e.g., at least the surface 812). Although described as being performed after coupling the transfer adapter 820 to the lumen defining device, in other instances, the user can disinfect the fluid reservoir using the disinfection member 840 prior to coupling the transfer adapter 820 to the lumen defining device. Moreover, in some embodiments, with the port 824 coupled to the lumen defining device, the user can manipulate the collection device 800 to remove a seal or the like from the transfer adapter 820, as described above with reference to the seal 238.

After substantially disinfecting at least the surface 812 of the fluid reservoir 810, the user can move the fluid reservoir 810 relative to the transfer adapter 820 such that the puncture member 850 engages (e.g., pierces) the port 813 defined by the surface 812 of the fluid reservoir 810, as indicated by the arrow OO in FIG. 34. Thus, the proximal end portion 851 of the puncture member 850 can extend beyond the sheath 853 to pierce the port 813 of the fluid reservoir 810 such that a portion of the puncture member 850 is disposed in an inner volume defined by the fluid reservoir 810, as shown in FIG. 34. In this manner, a lumen defined by the puncture member 850 can place the lumen defining device (and thus, a lumen of the patient) in fluid communication with the inner volume of the fluid reservoir 810. As described above, the fluid reservoir 810 can define a negative pressure that can exert a suction force in or on the lumen of the puncture member 850 when the puncture member 850 pierces the fluid reservoir 810 and, in turn, the negative pressure can exert a suction force within, for example, a vein of the patient to urge the bodily-fluid to flow within the fluid flow path to be disposed in the inner volume of the fluid reservoir 810. In some instances, the bodily-fluid can flow within the fluid flow path until a desired volume of bodily-fluid is disposed in the fluid reservoir 810, as described above. With the desired amount of bodily-fluid disposed in the fluid reservoir 810, the fluid reservoir 810 can be moved in the proximal direction to, for example, remove the fluid reservoir 810 from the inner volume 836 of the transfer adapter 820.

Any of the embodiments described here and/or portions thereof can be, for example, packaged, shipped, and/or sold independently, and/or in combination with any other suitable device for obtaining bodily-fluid samples. For example, FIGS. 35-38 illustrate a kit 970, which can include at least a package 971 configured to contain at least a transfer adapter 920 and a set of disinfection members 940. In some embodiments, the transfer adapter 920 can be any of the transfer adapters 220, 320, 420, 520, 620, and/or 820. As such, the transfer adapter 920 can define an inner volume (not shown in FIGS. 35-38) within which a puncture member (e.g., the puncture member 250 and/or the like) is disposed. Similarly, the transfer device 920 can includes and/or can be otherwise coupled to any of the disinfection members 240, 340, 440, 540, 640, and/or 840 (e.g., in addition to the disinfection members 940 shown in FIG. 35). Moreover, as shown, the kit 970 can include, for example, a bodily-fluid diversion device 980, which is coupled to a port of the transfer adapter 920. In other embodiments, the bodily-fluid diversion device 980 can be disposed within the package 971 and not coupled to transfer adapter 920. In some embodiments, the bodily-fluid diversion device 980 can be any of those described in U.S. Pat. No. 8,535,241, incorporated by reference above. In still other embodiments, the kit 970 need not include the bodily-fluid diversion device 980.

Figure 35:
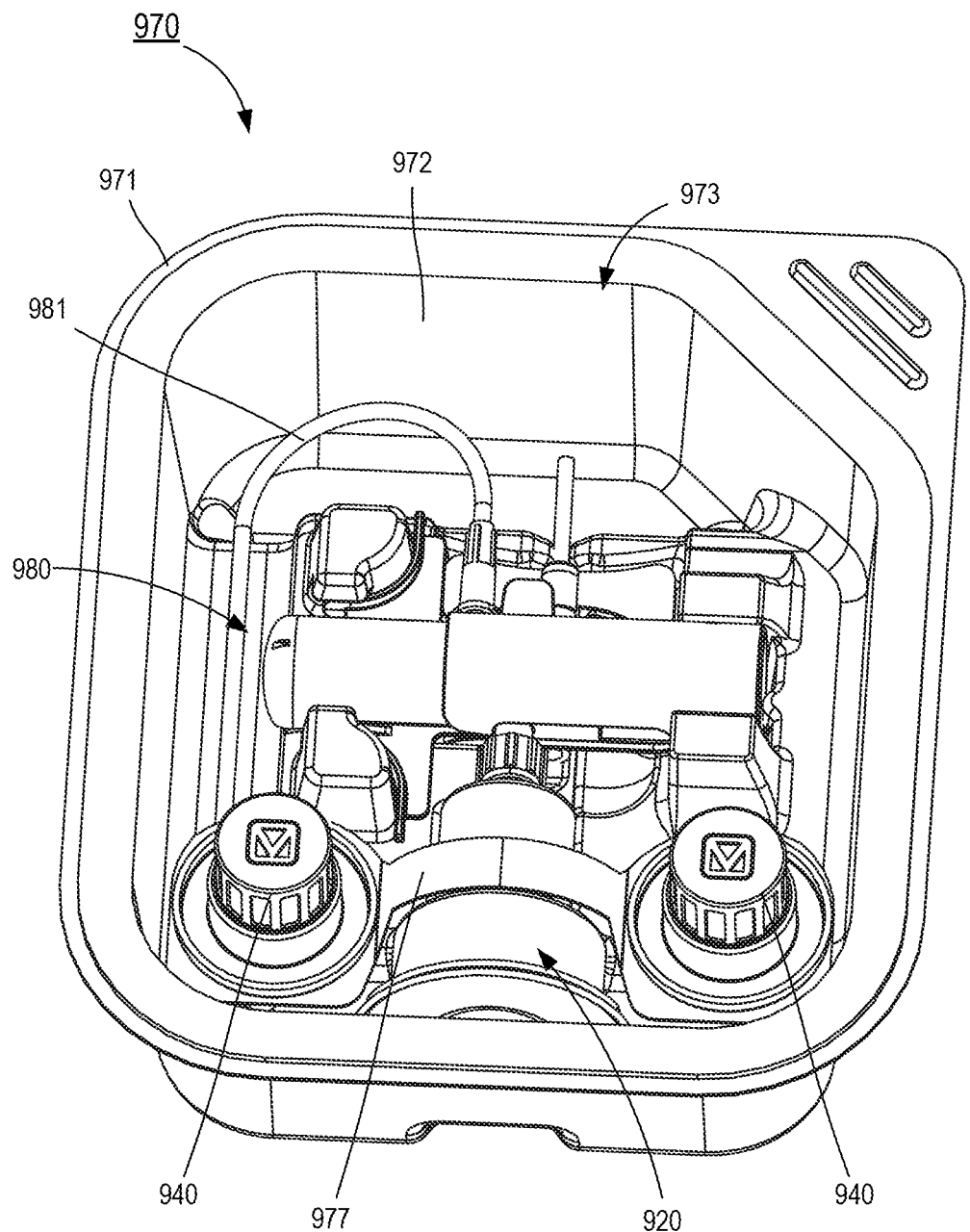
FIG. 35 is a perspective view of a kit including a bodily fluid collection device in a first configuration, according to an embodiment.
Figure 36:
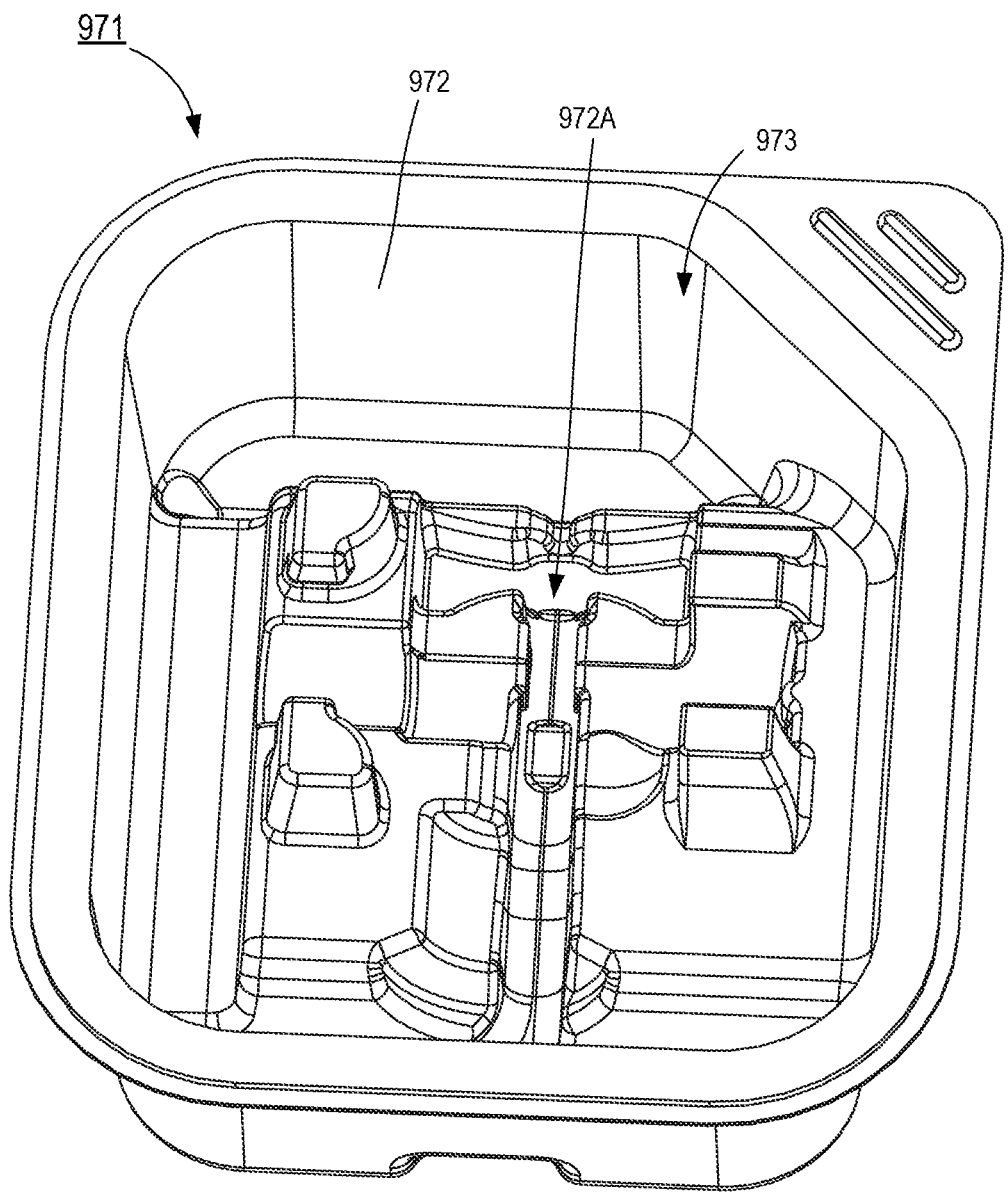
FIG. 36 is a perspective view of a package included in the kit of FIG. 35 and configured to at least temporarily contain the bodily fluid collection device shown in FIG. 35.
Figure 37:
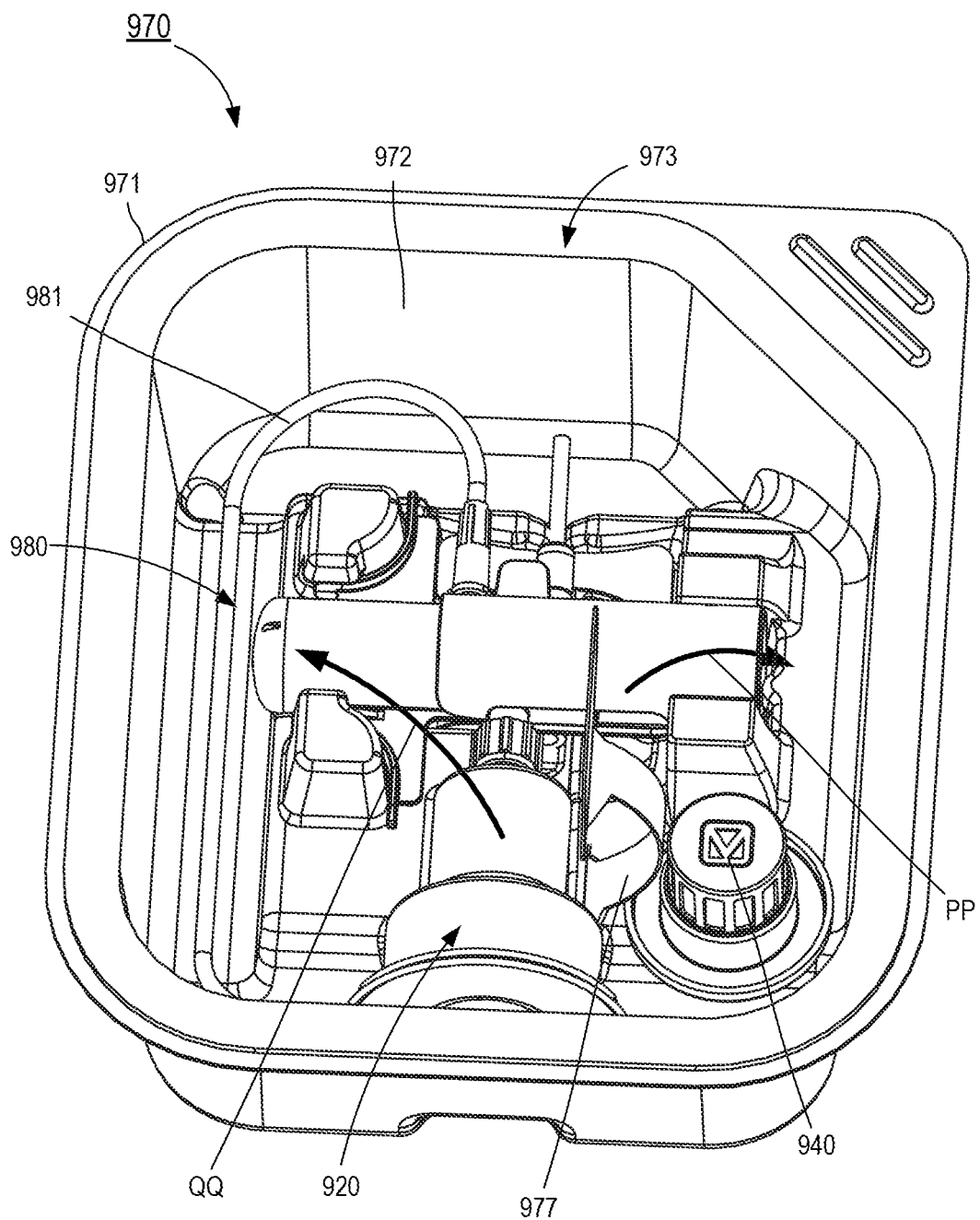
FIG. 37 is a perspective view of the kit of FIG. 35 in a second configuration.

As shown in FIGS. 35-37, the package 971 can be any suitable shape, size, and/or configuration. Specifically, in this embodiment, the package 971 includes an inner surface 972 and defines an inner volume 973. Although not shown in FIGS. 35-38, the package 971 can also include a substantially non-permeable cover and/or seal configured to fluidically isolate the inner volume 973 from a volume outside of the package 971 prior to opening of the package 971 and/or otherwise removing the cover and/or seal. Moreover, the arrangement of the kit 970 is such that the transfer adapter 920, the disinfection members 940 and the bodily-fluid diversion device 980 are disposed within the inner volume 973 of the package 971. Thus, the cover and/or the seal, for example, can engage a surface of the package 971 to define a substantially fluid tight and/or substantially hermetic seal therebetween. In some embodiments, the kit 970 can be sterilized and/or the like prior to fluidically isolating the inner volume 973 of the package 971 (e.g., the kit 970 can be disposed in an ethylene oxide environment or the like).

As shown in FIG. 36, the inner surface 972 of the package 971 can have and/or can define a contour portion 972A configured to matingly receive a portion of the transfer adapter 920, the disinfection members 940, and/or the bodily-fluid diversion device 980. In some embodiments, the portions of the transfer adapter 920, the disinfection members 940, and/or the bodily-fluid diversion device 980 can form a friction fit or the like with the contour 972A portion of the inner surface 972 such that the transfer adapter 920, the disinfection members 940, and/or the bodily-fluid diversion device 980 are maintained in a substantially fixed position relative to the package 971 (see e.g., FIG. 35).

As shown in FIGS. 35 and 37, the package 971 can include a retainer 977 or the like configured to selectively maintain at least the transfer adapter 920 in contact with and/or otherwise adjacent to the contour portion 972A of the inner surface 972. For example, in some embodiments, the retainer 977 can be a relatively flexible strap or the like that can be transitioned between a first configuration, in which the retainer 977 maintains the transfer adapter 920 in contact with the contour portion 972A, and a second configuration, in which the retainer 977 allows at least the transfer adapter 920 to be removed from the package 971. More specifically, as shown in FIG. 35, the kit 970 includes two disinfection members 940, which are at least temporarily maintained in contact with the inner surface 972 and disposed on opposite sides of the transfer adapter 920 when the transfer adapter 920 is in contact with the contour portion 972A of the inner surface 972. As such, opposite end portions of the retainer 977 can be disposed between disinfection members 940 and the inner surface 972 of the package 971, thereby coupling the retainer 977 to the inner surface 972. Therefore, the retainer 977 can form a band and/or strap between the disinfection members 940 that is operable in retaining at least the transfer adapter 920 in contact with and/or adjacent to the contour portion 972A of the inner surface 972. In some instances, this arrangement can force a user to comply with a disinfection protocol and/or at least remind the user to disinfect the fluid reservoir 910 prior to inserting the fluid reservoir 910 into the transfer adapter 920, as described above.

The disinfection members 940 can be, for example, a pad, a swab, a sponge, and/or the like that can include a disinfecting agent. In some embodiments, at least a surface of the disinfection members 940 can be impregnated with a disinfecting agent such as, those described above. In some embodiments, the disinfection members 940 can include and/or can define a portion that is substantially porous, for example, to act as a substrate for the disinfection agent. Moreover, the disinfection members 940 can include a cap or outer portion configured to provide structural integrity and/or strength. Although not shown, the cap and/or outer portion can define an inner volume within which the disinfection member 940 is disposed, as described in further detail herein.

Figure 38:
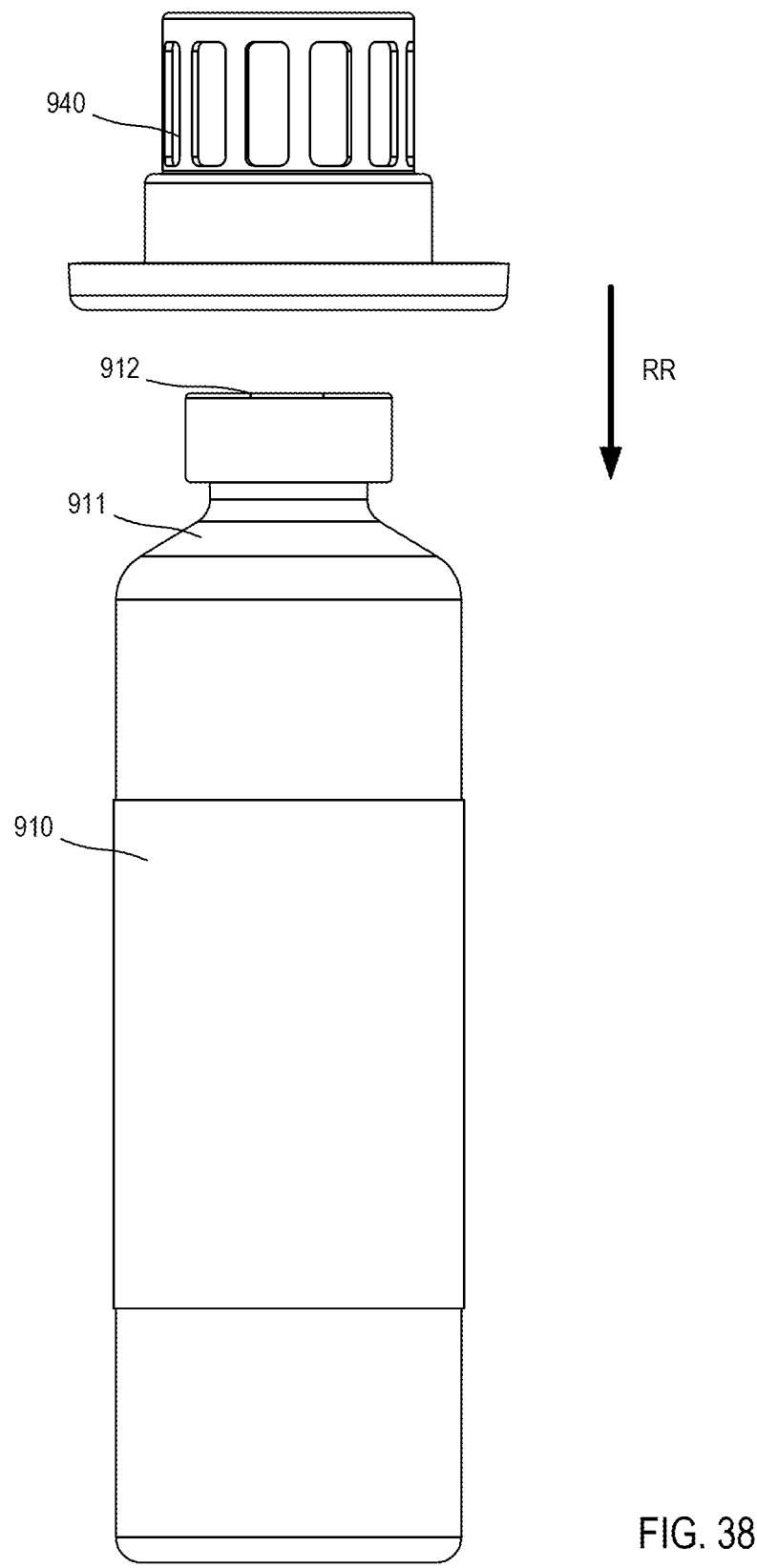
FIG. 38 is a front view of a disinfection member included in the kit of FIG. 35 and configured to couple to a fluid reservoir.

In user, a user can manipulate the package 971 by removing the cover and/or seal from the package 971 (not shown in FIGS. 35-38). Once removed, at least one of the disinfection members 940 can be removed from engagement (either directly or indirectly) with the inner surface 972. As shown in FIG. 38, the disinfection member 940 can be placed in contact with, for example, a distal end portion 911 of a fluid reservoir 910, as indicated by the arrow RR. In this manner, the disinfection member 940 can contact a distal surface 912 of the fluid reservoir 910 to substantially disinfect and/or sterilize the distal surface 912, as described above with reference to the disinfection members 240, 340, 440, 540, 640, and/or 840.

With at least one of the disinfection members 940 removed from the package 971, the retainer 977 can be transitioned from its first configuration (FIG. 35) to its second configuration, as indicated by the arrow PP in FIG. 37. For example, in some embodiments, the retainer 977 can be a relatively flexible strap or the like that can be moved, bent, deformed, and/or otherwise repositioned relative to at least the transfer adapter 920. Thus, at least the transfer adapter 920 can be removed for the inner volume 973 of the package 971, as indicated by the arrow QQ in FIG. 37. In some embodiments, the transfer adapter 920 can be coupled to the bodily-fluid diversion device 980 such that when the retainer 977 is in the second configuration, removal of the transfer adapter 920 also removes the bodily-fluid diversion device 980. As such, a lumen defining device 981 (e.g., a sterile flexible tubing, a catheter, and/or the like) can be placed in fluid communication with a lumen of a patient (e.g., via a peripheral intravenous line, via an indwelling cannula, and/or via venipuncture).

With the transfer adapter 920 in fluid communication with the patient via the bodily-fluid collection device 980 and the lumen defining device 981, and with the disinfection member 940 having substantially disinfected the distal surface 912 of the fluid reservoir 910, the user can move the fluid reservoir 910 relative to the transfer adapter 920 such that the puncture member (not shown) pierces the distal surface 912 of the fluid reservoir 910, as described in detail above. In this manner, a lumen defined by the puncture member 950 can place the bodily-fluid diversion device 980 and the lumen defining device 981 in selective fluid communication with the inner volume of the fluid reservoir 910. Thus, the user can manipulate the bodily-fluid diversion device 980, as described in U.S. Pat. No. 8,535,241 incorporated by reference above, to withdraw a volume of bodily-fluid that is substantially free from microbes such as dermally residing microbes.

Any of the embodiments described herein can include components that are manufactured, packaged, and sold independently or collectively. For example, in some instances, any of the embodiments described herein can be manufactured, assembled, and packaged collectively during a manufacturing process. In such instances, one or more disinfection members, such as those described herein, can be positioned within a collection device during a manufacturing process (e.g., during assembly), which be performed, for example, in a substantially sterile environment. Moreover, the position of the disinfection member can be such that during use, a clinician is substantially prevented from collecting and/or transferring a bodily-fluid sample into a fluid reservoir(s) without engaging the disinfection member to at least substantially sterilize a connection between the collection device and the fluid reservoir.

For example, in such embodiments, the disinfection member can substantially sterilize a surface of the fluid reservoir that is subsequently pierced by a puncture member of the collection device, as described in detail above with reference to specific embodiments. By ensuring that substantially no external contaminants and/or biological matter (e.g., skin cells, tumor cells, organ tissue, etc.) external to the target bodily-fluid source are captured in the sample vessel, diagnostic results can improve with increased consistency. With accurate diagnostic results, clinicians can derive an accurate treatment/action plan, thereby reducing the likelihood of misdiagnosing a patient, prescribing unnecessary treatment, holding the patient in a clinical and/or hospital setting for an undue period of time, and/or the like, which in turn, can substantially reduce a risk of the patient developing a further ailment (e.g., antibiotic complications, adverse drug reactions, hospital-acquired infection, and/or the like) as well as substantially reduce costs to hospital and/or other healthcare institutions.

Although not shown, any of the embodiments and/or methods described herein can be used in conjunction with and/or otherwise in the methods described in U.S. Patent Publication No. 2014/0155782 entitled, "Sterile Bodily-Fluid Collection Device and Methods," filed Dec. 4, 2013 (the "'782 publication"), the disclosure of which is incorporated herein by reference in its entirety. For example, the embodiments, described here can be used to collect a bodily-fluid sample, which in turn can be used in any of the testing methods, diagnostic methods, and/or analysis methods described in the '782 publication.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Where methods and/or events described above indicate certain events and/or procedures occurring in certain order, the ordering of certain events and/or procedures may be modified. Additionally, certain of the events may be performed concurrently in a parallel process when possible, as well as performed sequentially as described above.

The specific configurations of the various components can also be varied. For example, the size and specific shape of the various components can be different from the embodiments shown, while still providing the functions as described herein. More specifically, the size and shape of the various components can be specifically selected for a desired rate of bodily-fluid flow into a fluid reservoir. Similarly, the size and/or specific shape of various components can be specifically selected for a desired fluid reservoir. For example, portions of the embodiments described herein can be modified such that any suitable container, microcontainer, microliter container, vial, microvial, microliter vial, nanovial, sample bottle, culture bottle, etc. can be placed in contact with a disinfection member to sterilize one or more interfaces associated therewith prior to a bodily-fluid being drawn into a volume so defined.

What is claimed:
1. An apparatus, comprising:
   a transfer adapter including a proximal end portion and a distal end portion and defining an inner volume ther- ebetween, the distal end portion including a port configured to be placed in fluid communication with a bodily-fluid of a patient;
a fluid reservoir including a contact surface and configured to be inserted though the proximal end portion of the transfer adapter such that at least a portion of the fluid reservoir is movably disposed within the inner volume between a first position and a second position;
a disinfection member coupled to the transfer adapter and disposed within the inner volume, the disinfection member configured to be placed in contact with the contact surface of the fluid reservoir when the fluid reservoir is in the first position;
a seal removably coupled to a surface of the transfer adapter at the proximal end portion, the seal configured to fluidically isolate the inner volume defined by the transfer adapter, the seal configured to be removed from the surface of the transfer adapter to allow at least the portion of the fluid reservoir to be movably disposed in the inner volume; and
a puncture member disposed within the inner volume of the transfer adapter and fluidically coupled to the port, the puncture member configured to puncture the contact surface of the fluid reservoir to place the puncture member in fluid communication with the fluid reservoir when the seal is removed from the surface of the transfer adapter the fluid reservoir is moved from the first position to the second position.

2. The apparatus of claim 1, wherein at least a portion of the puncture member is disposed within a sheath, the sheath configured to be transitioned between a first configuration wherein the sheath substantially surrounds the puncture member and a second configuration wherein a portion of puncture member is disposed outside of the sheath.

3. The apparatus of claim 1, wherein the disinfection member is configured to substantially disinfect the contact surface of the fluid reservoir.

4. The apparatus of claim 1, wherein the disinfection member is configured to be transitioned between a first configuration and a second configuration when the fluid reservoir is moved from the first position to the second position.

5. The apparatus of claim 1, wherein the disinfection member is at least one of a diaphragm or a porous substrate.

6. The apparatus of claim 1, wherein the transfer adapter includes a surface configured to substantially limit distal movement of the fluid reservoir when the fluid reservoir is moved from the first position to the second position.

7. The apparatus of claim 1, wherein the transfer adapter defines a plurality of vents, the plurality of vents configured to allow a disinfection agent to evaporate from the contact surface of the fluid reservoir prior to the fluid reservoir being placed in the second position.

8. The apparatus of claim 1, wherein the disinfection member is disposed within an inner volume defined by a cap removably disposed within the inner volume defined by the transfer adapter, the fluid reservoir configured to be disposed within the inner volume defined by the cap when placed in the first position.

9. The apparatus of claim 1, wherein the transfer adapter includes a retention member, the retention member configured to at least temporarily couple the disinfection member to the transfer adapter.

10. The apparatus of claim 1, wherein the proximal end portion of the transfer adapter defines an opening in fluid communication with the inner volume, the fluid reservoir configured to be inserted through the opening to dispose at least a portion of the fluid reservoir within the inner volume, the seal is coupled to the surface of the transfer adapter such that the seal at least temporarily obstructs the opening prior to the fluid reservoir being placed in the first position.

11. The apparatus of claim 1, wherein the disinfection member is a sponge that includes a disinfecting agent.

12. A method, comprising:
establishing fluid communication between a patient and a transfer adapter, the transfer adapter defining an inner volume configured to house a puncture member configured to be in fluid communication with the patient, the transfer adapter configured to include a disinfection member disposed within the inner volume of the transfer adapter;
removing a seal temporarily coupled to a surface of the transfer adapter at a proximal end portion thereof, the seal configured to fluidically isolate the inner volume defined by the transfer adapter when coupled to the surface of the transfer adapter;
inserting a portion of a fluid reservoir into the inner volume of the transfer adapter after the removing of the seal;
moving the fluid reservoir to a first position to place a contact surface of the fluid reservoir in contact with the disinfection member disposed in the inner volume; and
moving the fluid reservoir to a second position, a portion of the fluid reservoir disposed within the inner volume when the fluid reservoir is in the second position such that the puncture member punctures the contact surface of the fluid reservoir to place the fluid reservoir in fluid communication with the patient.

13. The method of claim 12, wherein the transfer adapter includes a port, the port configured to be placed in fluid communication with a lumen defining device in fluid communication with the patient, the puncture member configured to be in fluid communication with the port.

14. The method of claim 12, wherein the disinfection member is at least one of a diaphragm or a porous substrate.

15. The method of claim 12, wherein the disinfection member is configured to be transitioned between a first configuration and a second configuration when the fluid reservoir is moved from the first position to the second position.

16. The method of claim 12, further comprising:
venting the inner volume of the transfer adapter prior to the moving of the fluid reservoir to the second position.

17. The method of claim 12, wherein the moving of the fluid reservoir to the second position includes transitioning a sheath from a first configuration in which the puncture member is substantially disposed within the sheath to a second configuration in which a proximal end portion of the puncture member is substantially outside of the sheath.

18. The method of claim 12, wherein the seal coupled to the surface of the transfer adapter at least temporarily obstructs the inner volume of the transfer adapter prior to moving the fluid reservoir to the first position.

19. The method of claim 12, wherein the disinfection member prevents moving the fluid reservoir to the second position prior to moving the fluid reservoir to the first position.

* * * * *